(12) United States Patent
Muller et al.

(10) Patent No.: US 8,906,932 B2
(45) Date of Patent: Dec. 9, 2014

(54) METHODS OF TREATING CANCER USING 3-(5-AMINO-2-METHYL-4-OXO-4HQUINAZOLIN-3-YL)-PIPERIDINE-2,6-DIONE

(75) Inventors: George W. Muller, Rancho Santa Fe, CA (US); Peter H. Schafer, Somerset, NJ (US); Hon-Wah Man, Princeton, NJ (US); Ling-Hua Zhang, Mountain Lakes, NJ (US); Anita Gandhi, Bernardsville, NJ (US); Rajesh Chopra, Summit, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 13/417,088

(22) Filed: Mar. 9, 2012

(65) Prior Publication Data

US 2012/0230983 A1    Sep. 13, 2012

Related U.S. Application Data

(60) Provisional application No. 61/451,995, filed on Mar. 11, 2011, provisional application No. 61/480,272, filed on Apr. 28, 2011.

(51) Int. Cl.
| | | |
|---|---|---|
| *A61K 31/517* | (2006.01) | |
| *A61K 45/06* | (2006.01) | |
| *A61K 31/196* | (2006.01) | |
| *A61K 31/352* | (2006.01) | |
| *A61K 31/4184* | (2006.01) | |
| *A61K 31/475* | (2006.01) | |
| *A61K 31/704* | (2006.01) | |

(52) U.S. Cl.
CPC ............. *A61K 31/517* (2013.01); *A61K 45/06* (2013.01); *A61K 31/196* (2013.01); *A61K 31/352* (2013.01); *A61K 31/4184* (2013.01); *A61K 31/475* (2013.01); *A61K 31/704* (2013.01)
USPC ..................................... 514/266.22

(58) Field of Classification Search
None
See application file for complete search history.

(56) References Cited

U.S. PATENT DOCUMENTS

2012/0322073 A1 * 12/2012 Lopez-Girona et al. ..... 435/6.12

FOREIGN PATENT DOCUMENTS

| WO | WO 2008039489 A2 * | 4/2008 | ........... C07D 401/04 |
| WO | WO 2008139169 A1 * | 11/2008 | ............... C12Q 1/68 |

OTHER PUBLICATIONS

"Mutations of multiple genes cause deregulation of NF-kB in diffuse large B-cell lymphoma" by Compagno et al., Nature 459, 717-21 (2009).*

* cited by examiner

*Primary Examiner* — Theodore R West
(74) *Attorney, Agent, or Firm* — Jones Day

(57) ABSTRACT

Provided herein are methods of treating, preventing and/or managing cancers, which comprise administering to a patient 3-(5-amino-2-methyl-4-oxo-4H-quinazolin-3-yl)-piperidine-2,6-dione, or an enantiomer or a mixture of enantiomers thereof, or a pharmaceutically acceptable salt, solvate, hydrate, co-crystal, clathrate, or polymorph thereof.

27 Claims, 24 Drawing Sheets

Figure 1A:
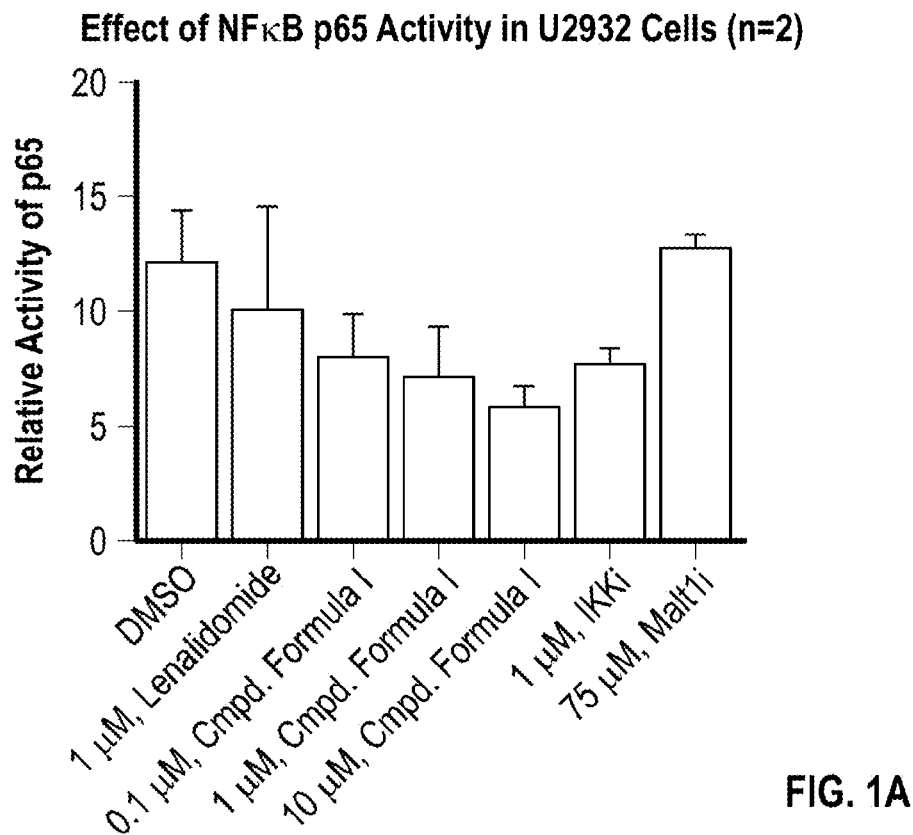
Figure 1B:
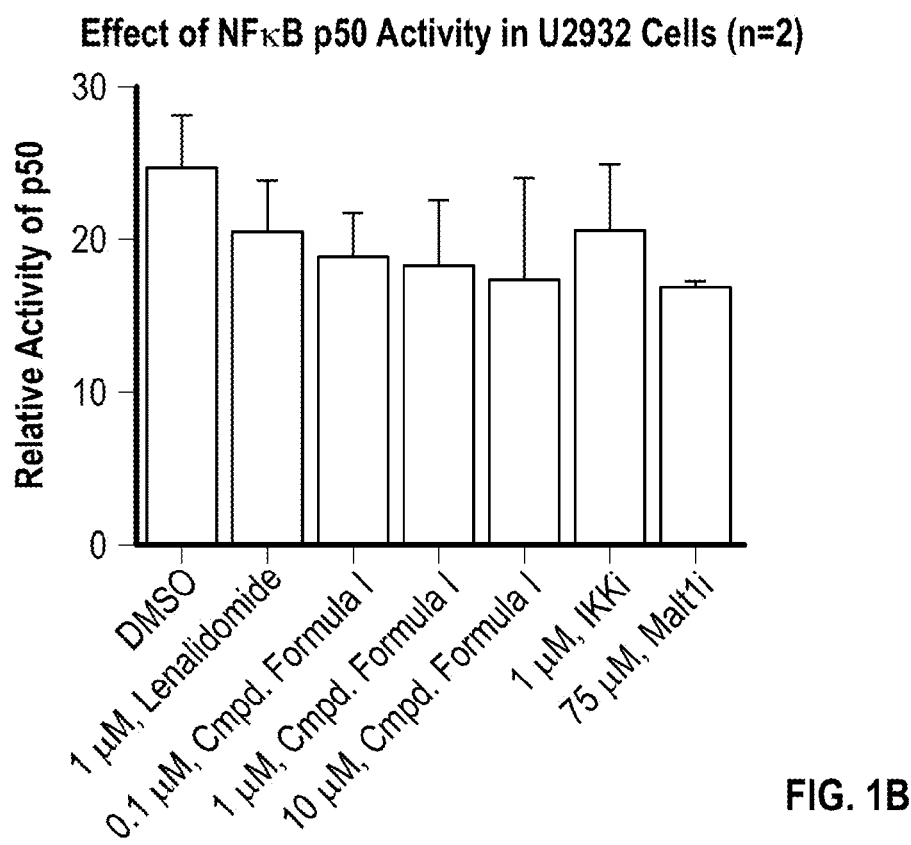
Figure 1C:
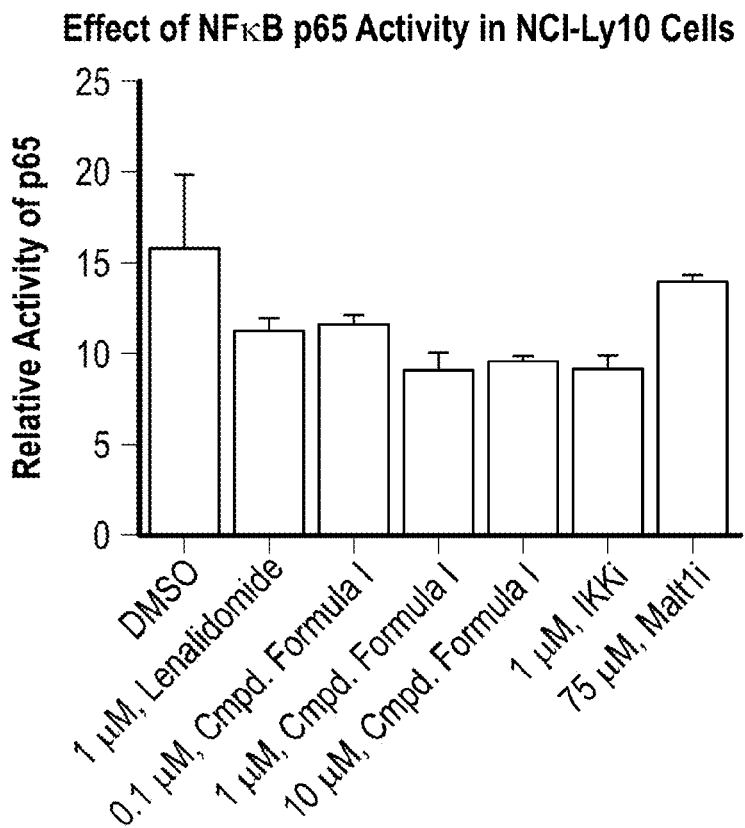
Figure 1D:
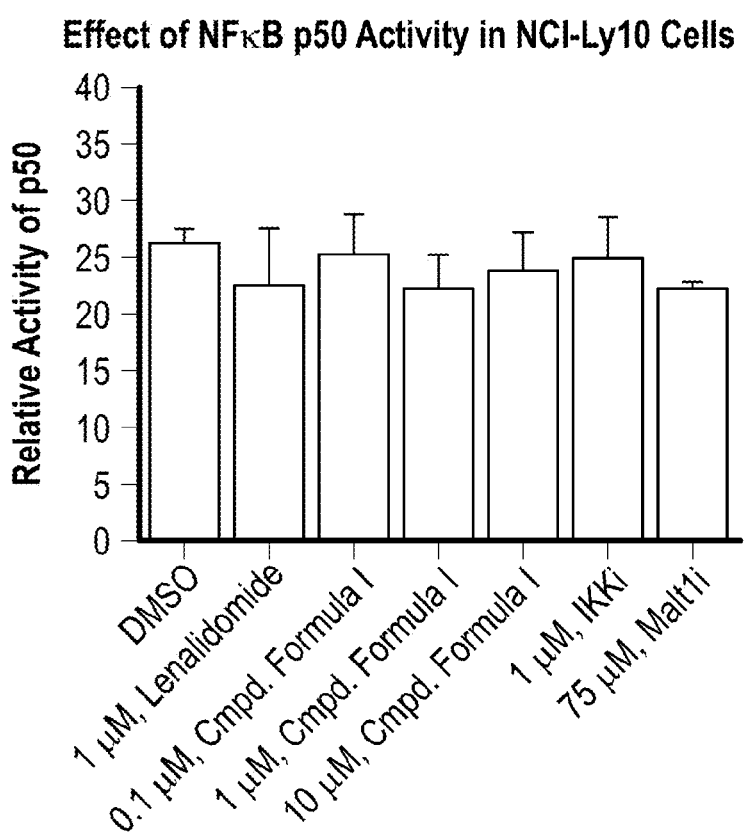

| Proliferation | CC-122 | CC-5013 |
|---|---|---|
| OPM2 (n=2) | 0.04 | 0.3 |
| H929 (n=3) | 0.07 | 10.5 |
| CAG (n=3) | 0.085 | 12.2 |
| MM1.S (n=3) | 0.3 | 8.6 |
| DF15 (n=3) | 0.4 | 19.23 |
| U266 (n=3) | 0.4 | 12.6 |
| KMS34 (n=3) | 9.7 | >10 |
| LP-1 (n=3) | >10 | >10 |
| DF15R (n=3) | >10 | >10 |
| Anbl-6 (n=4) | >10 | >10 |

ZR-75-1 Breast Cells

METHODS OF TREATING CANCER USING 3-(5-AMINO-2-METHYL-4-OXO-4HQUINAZOLIN-3-YL)-PIPERIDINE-2,6-DIONE

This application claims the benefit of U.S. Provisional Patent Application No. 61/451,995, filed on Mar. 11, 2011, and U.S. Provisional Patent Application No. 61/480,272, filed on Apr. 28, 2011, the entireties of which are incorporated herein by reference.

1. FIELD OF THE INVENTION

Provided herein are methods of treating, preventing and/or managing cancers, which comprise administering to a patient 3-(5-amino-2-methyl-4-oxo-4H-quinazolin-3-yl)-piperidine-2,6-dione, or an enantiomer or a mixture of enantiomers thereof, or a pharmaceutically acceptable salt, solvate, hydrate, co-crystal, clathrate, or polymorph thereof.

2. BACKGROUND OF THE INVENTION

2.1 Pathobiology of Cancer

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., *Immunology*, 17.1-17.12 (3rd ed., Mosby, St. Louis, Mo., 1993).

There is an enormous variety of cancers which are described in detail in the medical literature. Examples include cancer of the lung, colon, rectum, prostate, breast, brain, and intestine. The incidence of cancer continues to climb as the general population ages, as new cancers develop, and as susceptible populations (e.g., people infected with AIDS or excessively exposed to sunlight) grow. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a,b-FGF), angiogenin, vascular endothelial growth factor (VEGF), and TNF-α. Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g., TNF-α, b-FGF).

Lymphoma refers to cancers that originate in the lymphatic system. Lymphoma is characterized by malignant neoplasms of lymphocytes—B lymphocytes and T lymphocytes (i.e., B-cells and T-cells). Lymphoma generally starts in lymph nodes or collections of lymphatic tissue in organs including, but not limited to, the stomach or intestines. Lymphoma may involve the marrow and the blood in some cases. Lymphoma may spread from one site to other parts of the body.

The treatment of various forms of lymphomas are described, for example, in U.S. Pat. No. 7,468,363, the entirety of which is incorporated herein by reference. Such lymphomas include, but are not limited to, Hodgkin's lymphoma, non-Hodgkin's lymphoma, cutaneous B-cell lymphoma, activated B-cell lymphoma, diffuse large B-cell lymphoma (DLBCL), mantle cell lymphoma (MCL), follicular center lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-Cell lymphoma and mantle zone lymphoma and low grade follicular lymphoma.

Non-Hodgkin's lymphoma (NHL) is the fifth most common cancer for both men and women in the United States, with an estimated 63,190 new cases and 18,660 deaths in 2007. Jemal A, et al., *CA Cancer J Clin* 2007; 57(1):43-66. The probability of developing NHL increases with age and the incidence of NHL in the elderly has been steadily increasing in the past decade, causing concern with the aging trend of the US population. Id. Clarke C A, et al., *Cancer* 2002; 94(7):2015-2023.

Diffuse large B-cell lymphoma (DLBCL) accounts for approximately one-third of non-Hodgkin's lymphomas. While some DLBCL patients are cured with traditional chemotherapy, the remainder die from the disease. Anticancer drugs cause rapid and persistent depletion of lymphocytes, possibly by direct apoptosis induction in mature T and B cells. See K. Stahnke et al., *Blood* 2001, 98:3066-3073. Absolute lymphocyte count (ALC) has been shown to be a prognostic factor in follicular non-Hodgkin's lymphoma and recent results have suggested that ALC at diagnosis is an important prognostic factor in diffuse large B-cell lymphoma. See D. Kim et al., *Journal of Clinical Oncology*, 2007 ASCO Annual Meeting Proceedings Part I. Vol 25, No. 18S (June 20 Supplement), 2007: 8082.

Leukemia refers to malignant neoplasms of the blood-forming tissues. Various forms of leukemias are described, for example, in U.S. Pat. No. 7,393,862 and U.S. provisional patent application No. 60/380,842, filed May 17, 2002, the entireties of which are incorporated herein by reference. Although viruses reportedly cause several forms of leukemia in animals, causes of leukemia in humans are to a large extent unknown. *The Merck Manual*, 944-952 (17$^{th}$ ed. 1999). Transformation to malignancy typically occurs in a single cell through two or more steps with subsequent proliferation and clonal expansion. In some leukemias, specific chromosomal translocations have been identified with consistent leukemic cell morphology and special clinical features (e.g., translocations of 9 and 22 in chronic myelocytic leukemia, and of 15 and 17 in acute promyelocytic leukemia). Acute leukemias are predominantly undifferentiated cell populations and chronic leukemias more mature cell forms.

Acute leukemias are divided into lymphoblastic (ALL) and non-lymphoblastic (ANLL) types. *The Merck Manual*, 946-949 (17$^{th}$ ed. 1999). They may be further subdivided by their morphologic and cytochemical appearance according to the French-American-British (FAB) classification or according to their type and degree of differentiation. The use of specific B- and T-cell and myeloid-antigen monoclonal antibodies are most helpful for classification. ALL is predominantly a childhood disease which is established by laboratory findings and bone marrow examination. ANLL, also known as acute myelogenous leukemia or acute myeloblastic leukemia (AML), occurs at all ages and is the more common acute leukemia among adults; it is the form usually associated with irradiation as a causative agent.

Chronic leukemias are described as being lymphocytic (CLL) or myelocytic (CML). *The Merck Manual,* 949-952 (17$^{th}$ ed. 1999). CLL is characterized by the appearance of mature lymphocytes in blood, bone marrow, and lymphoid organs. The hallmark of CLL is sustained, absolute lymphocytosis (>5,000/μL) and an increase of lymphocytes in the bone marrow. Most CLL patients also have clonal expansion of lymphocytes with B-cell characteristics. CLL is a disease of middle or old age. In CML, the characteristic feature is the predominance of granulocytic cells of all stages of differentiation in blood, bone marrow, liver, spleen, and other organs. In the symptomatic patient at diagnosis, the total white blood cell (WBC) count is usually about 200,000/μL, but may reach 1,000,000/μL. CML is relatively easy to diagnose because of the presence of the Philadelphia chromosome.

In addition to the acute and chronic categorization, neoplasms are also categorized based upon the cells giving rise to such disorder into precursor or peripheral. See e.g., U.S. patent publication no. 2008/0051379, the disclosure of which is incorporated herein by reference in its entirety. Precursor neoplasms include ALLs and lymphoblastic lymphomas and occur in lymphocytes before they have differentiated into either a T- or B-cell. Peripheral neoplasms are those that occur in lymphocytes that have differentiated into either T- or B-cells. Such peripheral neoplasms include, but are not limited to, B-cell CLL, B-cell prolymphocytic leukemia, lymphoplasmacytic lymphoma, mantle cell lymphoma, follicular lymphoma, extranodal marginal zone B-cell lymphoma of mucosa-associated lymphoid tissue, nodal marginal zone lymphoma, splenic marginal zone lymphoma, hairy cell leukemia, plasmacytoma, diffuse large B-cell lymphoma and Burkitt lymphoma. In over 95 percent of CLL cases, the clonal expansion is of a B cell lineage. See Cancer: Principles & Practice of Oncology (3rd Edition) (1989) (pp. 1843-1847). In less than 5 percent of CLL cases, the tumor cells have a T-cell phenotype. Notwithstanding these classifications, however, the pathological impairment of normal hematopoiesis is the hallmark of all leukemias.

Multiple myeloma (MM) is a cancer of plasma cells in the bone marrow. Normally, plasma cells produce antibodies and play a key role in immune function. However, uncontrolled growth of these cells leads to bone pain and fractures, anemia, infections, and other complications. Multiple myeloma is the second most common hematological malignancy, although the exact causes of multiple myeloma remain unknown. Multiple myeloma causes high levels of proteins in the blood, urine, and organs, including but not limited to M-protein and other immunoglobulins (antibodies), albumin, and beta-2-microglobulin. M-protein, short for monoclonal protein, also known as paraprotein, is a particularly abnormal protein produced by the myeloma plasma cells and can be found in the blood or urine of almost all patients with multiple myeloma.

Skeletal symptoms, including bone pain, are among the most clinically significant symptoms of multiple myeloma. Malignant plasma cells release osteoclast stimulating factors (including IL-1, IL-6 and TNF) which cause calcium to be leached from bones causing lytic lesions; hypercalcemia is another symptom. The osteoclast stimulating factors, also referred to as cytokines, may prevent apoptosis, or death of myeloma cells. Fifty percent of patients have radiologically detectable myeloma-related skeletal lesions at diagnosis. Other common clinical symptoms for multiple myeloma include polyneuropathy, anemia, hyperviscosity, infections, and renal insufficiency.

Solid tumors are abnormal masses of tissue that may, but usually do not contain cysts or liquid areas. Solid tumors may be benign (not cancer), or malignant (cancer). Different types of solid tumors are named for the type of cells that form them. Examples of types solid tumors include, but are not limited to malignant melanoma, adrenal carcinoma, breast carcinoma, renal cell cancer, carcinoma of the pancreas, non-small-cell lung carcinoma (NSCLC) and carcinoma of unknown primary. Drugs commonly administered to patients with various types or stages of solid tumors include, but are not limited to, celebrex, etoposide, cyclophosphamide, docetaxel, apecitabine, IFN, tamoxifen, IL-2, GM-CSF, or a combination thereof.

While patients who achieve a complete remission after initial therapy have a good chance for cure, less than 10% of those who do not respond or relapse achieve a cure or a response lasting longer than 3 years. See Cerny T, et al., *Ann Oncol* 2002; 13 Suppl 4:211-216.

Rituximab is known to deplete normal host B cells. See M. Aklilu et al., Annals of Oncology 15:1109-1114, 2004. The long-term immunologic effects of B cell depletion with rituximab and the characteristics of the reconstituting B cell pool in lymphoma patients are not well defined, despite the widespread usage of this therapy. See Jennifer H. Anolik et al., *Clinical Immunology*, vol. 122, issue 2, February 2007, pages 139-145.

The approach for patients with relapsed or refractory disease relies heavily on experimental treatments followed by stem cell transplantation, which may not be appropriate for patients with a poor performance status or advanced age. Therefore, a tremendous demand exists for new methods that can be used to treat patients with NHL.

The link between cancer an altered cellular metabolism has been well established. See Cairns, R. A., et al. *Nature Rev.,* 2011, 11:85-95. Understanding tumor cell metabolism and the associated genetic changes thereof may lead to the identification of improved methods of cancer treatment. Id. For example, tumor cell survival and proliferation via increased glucose metabolism has been linked to the PIK3 pathway, whereby mutations in tumor suppressor genes such as PTEN activate tumor cell metabolism. Id. AKT1 (a.k.a., PKB) stimulates glucose metabolism associated with tumor cell growth by various interactions with PFKFB3, ENTPD5, mTOR and TSC2 (a.k.a., tuberin). Id.

Transcription factors HIF1 and HIF2 are largely responsible for cellular response to low oxygen conditions often associated with tumors. Id. Once activated, HIF1 promotes tumor cell capacity to carry out glycolysis. Id. Thus, inhibition of HIF1 may slow or reverse tumor cell metabolism. Activation of HIF1 has been linked to PI3K, tumor suppressor proteins such as VHL, succinate dehydrogenase (SDH) and fumarate hydratase. Id. The oncogenic transcription factor MYC has also been linked to tumor cell metabolism, specifically glycolysis. Id. MYC also promotes cell proliferation by glutamine metabolic pathways. Id.

AMP-activated protein kinase (AMPK) functions as a metabolic check point which tumor cells must overcome in order to proliferate. Id. Several mutations have been idenitifed which suppress AMPK signaling in tumor cells. See Shackelford, D. B. & Shaw, R. J., *Nature Rev. Cancer,* 2009, 9: 563-575. STK11 has been identified as a tumor suppressor gene related to the role of AMPK. See Cairns, R. A., et al. *Nature Rev.,* 2011, 11:85-95.

The transcription factor p53, a tumor suppressor, also has an important role in the regulation of cellular metabolism. Id. The loss of p53 in tumor cells may be a significant contributor to changes in tumor cell metabolism to the glycolytic pathway. Id. The OCT1 transcription factor, another potential target for chemotherapeutics, may cooperate with p53 in regulating tumor cell metabolism. Id.

Pyruvate kinate M2 (PKM2) promotes changes in cellular metabolism which confer metabolic advantages to cancer cells by supporting cell proliferation. Id. For example, lung cancer cells which express PKM2 over PKM1 have been found to have such an advantage. Id. In the clinic, PKM2 has been identified as being overexpressed in a number of cancer types. Id. Thus PKM2 may be a useful biomarker for the early detection of tumors.

Mutations in isocitrate dehydrogenases IDH1 and IDH2 have been linked to tumorigenesis, specifically, in glioblastoma and acute myeloid leukemia. See Mardis, E. R. et al., *N. Engl. J. Med.,* 2009, 361: 1058-1066; Parsons, D. W. et al., *Science,* 2008, 321: 1807-1812.

The incidence of cancer continues to climb as the general population ages, as new cancers develop, and as susceptible populations (e.g., people infected with AIDS, the elderly or excessively exposed to sunlight) grow. A tremendous demand therefore exists for new methods, treatments and compositions that can be used to treat patients with cancer including but not limited to those with lymphoma, NHL, multiple myeloma, AML, leukemias, and solid tumors.

Accordingly, compounds that can control and/or inhibit unwanted angiogenesis or inhibit the production of certain cytokines, including TNF-α, may be useful in the treatment and prevention of various forms of cancer.

2.2 Methods of Treating Cancer

Current cancer therapy may involve surgery, chemotherapy, hormonal therapy and/or radiation treatment to eradicate neoplastic cells in a patient (see, for example, Stockdale, 1998, *Medicine,* vol. 3, Rubenstein and Federman, eds., Chapter 12, Section IV). Recently, cancer therapy could also involve biological therapy or immunotherapy. All of these approaches may pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Certain biological and other therapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A number of cancer chemotherapeutics act by inhibiting DNA synthesis, either directly or indirectly by inhibiting the biosynthesis of deoxyribonucleotide triphosphate precursors, to prevent DNA replication and concomitant cell division. Gilman et al., *Goodman and Gilman's: The Pharmacological Basis of Therapeutics,* Tenth Ed. (McGraw Hill, N.Y.).

Despite availability of a variety of chemotherapeutic agents, chemotherapy has many drawbacks. Stockdale, *Medicine,* vol. 3, Rubenstein and Federman, eds., ch. 12, sect. 10, 1998. Almost all chemotherapeutic agents are toxic, and chemotherapy causes significant and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as multidrug resistance. Because of the drug resistance, many cancers prove refractory to standard chemotherapeutic treatment protocols.

There exists a significant need for safe and effective methods of treating, preventing and managing cancer, particularly for cancers that are refractory to standard treatments, such as surgery, radiation therapy, chemotherapy and hormonal therapy, while reducing or avoiding the toxicities and/or side effects associated with the conventional therapies.

2.3 Cereblon

The protein Cereblon (CRBN) is a 442-amino acid protein conserved from plant to human. In humans, the CRBN gene has been identified as a candidate gene of an autosomal recessive nonsyndromic mental retardation (ARNSMR). See Higgins, J. J. et al., *Neurology,* 2004, 63:1927-1931. CRBN was initially characterized as an RGS-containing novel protein that interacted with a calcium-activated potassium channel protein (SLO1) in the rat brain, and was later shown to interact with a voltage-gated chloride channel (ClC-2) in the retina with AMPK7 and DDB1. See Jo, S. et al., *J. Neurochem,* 2005, 94:1212-1224; Hohberger B. et al., *FEBS Lett,* 2009, 583:633-637; Angers S. et al., *Nature,* 2006, 443:590-593. DDB1 was originally identified as a nucleotide excision repair protein that associates with damaged DNA binding protein 2 (DDB2). Its defective activity causes the repair defect in the patients with xeroderma pigmentosum complementation group E (XPE). DDB1 also appears to function as a component of numerous distinct DCX (DDB1-CUL4-X-box) E3 ubiquitin-protein ligase complexes which mediate the ubiquitination and subsequent proteasomal degradation of target proteins. CRBN has also been identified as a target for the development of therapeutic agents for diseases of the cerebral cortex. See WO 2010/137547 A1.

Cereblon has recently been identified as a key molecular target that binds to thalidomide to cause birth defects. See Ito, T. et al., *Science,* 2010, 327:1345-1350. DDB1 was found to interact with CRBN and, thus, was indirectly associated with thalidomide. Moreover, thalidomide was able to inhibit autoubiquitination of CRBN in vitro, suggesting that thalidomide is an E3 ubiquitin-ligase inhibitor. Importantly, this activity was inhibited by thalidomide in wild-type cells, but not in cells with mutated CRBN binding sites that prevent thalidomide binding. The thalidomide binding site was mapped to a highly conserved C-terminal 104 amino acid region in CRBN. Individual point mutants in CRBN, Y384A and W386A were both defective for thalidomide binding, with the double point mutant having the lowest thalidomide-binding activity. A link between CRBN and the teratogenic effect of thalidomide was confirmed in animal models of zebra-fish and chick embryos. Understanding thalidomide and other drug targets will allow the definition of the molecular mechanisms of efficacy and/or toxicity and may lead to drugs with improved efficacy and toxicity profiles.

3. SUMMARY OF THE INVENTION

Provided herein are methods of treating and preventing cancer, including primary and metastatic cancer, as well as cancer that is refractory or resistant to conventional chemotherapy, which comprise administering to a patient in need of such treatment or prevention a therapeutically or prophylactically effective amount of 3-(5-amino-2-methyl-4-oxo-4H-quinazolin-3-yl)-piperidine-2,6-dione, having the structure of Formula I:

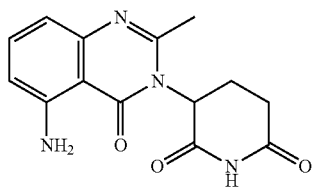

(I)

or an enantiomer or a mixture of enantiomers thereof, or a pharmaceutically acceptable salt, solvate, hydrate, co-crystal, clathrate, or polymorph thereof as a single agent or as a part of a combination therapy.

Also provided herein are methods of managing cancer (e.g., preventing its recurrence, or lengthening the time of remission), which comprise administering to a patient in need of such management a therapeutically or prophylactically effective amount of 3-(5-amino-2-methyl-4-oxo-4H-quinazolin-3-yl)-piperidine-2,6-dione, or an enantiomer or a mixture of enantiomers thereof, or a pharmaceutically acceptable salt, solvate, hydrate, co-crystal, clathrate, or polymorph thereof.

Further provided herein are methods of treating, preventing, or managing cancer, comprising administering to a patient in need of such treatment, prevention, or management a therapeutically or prophylactically effective amount of 3-(5-amino-2-methyl-4-oxo-4H-quinazolin-3-yl)-piperidine-2,6-dione, or an enantiomer or a mixture of enantiomers thereof, or a pharmaceutically acceptable salt, solvate, hydrate, co-crystal, clathrate, or polymorph thereof; in combination with a therapy conventionally used to treat, prevent, or manage cancer. Examples of such conventional therapies include, but are not limited to, surgery, chemotherapy, radiation therapy, hormonal therapy, biological therapy, and immunotherapy.

Provided herein is a method for treating, preventing, or managing cancer, comprising administering to a patient in need of such treatment, prevention, or management 3-(5-amino-2-methyl-4-oxo-4H-quinazolin-3-yl)-piperidine-2,6-dione, or an enantiomer or a mixture of enantiomers thereof, or a pharmaceutically acceptable salt, solvate, hydrate, co-crystal, clathrate, or polymorph thereof, in an amount that is sufficient to provide a plasma concentration of the compound at steady state, of about 0.001 to about 100 µM. In another embodiment, the amount is sufficient to provide a peak plasma concentration of the compound at steady state, of about 0.001 to about 100 µM. In another embodiment, the amount is sufficient to provide a trough plasma concentration of the compound at steady state, of about 0.01 to about 100 µM. In another embodiment, the amount is sufficient to provide an area under the curve (AUC) of the compound, ranging from about 100 to about 100,000 ng*hr/mL.

In certain embodiments, provided herein are methods for the treatment or management of lymphoma, multiple myeloma, leukemia, and solid tumors.

In some embodiments, the lymphoma is selected from the group consisting of Hodkin's lymphoma, non-Hodgkin's lymphoma, AIDS-related lymphomas, anaplastic large-cell lymphoma, angioimmunoblastic lymphoma, blastic NK-cell lymphoma, Burkitt's lymphoma, Burkitt-like lymphoma (small non-cleaved cell lymphoma, small lymphocytic lymphoma, cutaneous T-cell lymphoma, diffuse large B-cell Lymphoma, enteropathy-type T-cell lymphoma, lymphoblastic lymphoma, mantle cell lymphoma, marginal zone lymphoma, nasal T-cell lymphoma, pediatric lymphoma, peripheral T-cell lymphomas, primary central nervous system lymphoma, transformed lymphomas, treatment-related T-cell lymphomas and Waldenstrom's macroglobulinemia.

In some embodiments, the leukemia is selected from the group consisting of acute myeloid leukemia (AML), T-cell leukemia, chronic myeloid leukemia (CML), chronic lymphocytic leukemia (CLL) and acutl lymphoblastic leukemia (ALL).

In some embodiments, the solid tumor is selected from the group consisting of melanoma, head and neck tumors, breast carcinoma, non-small cell lung carcinoma, ovarian carcinoma, pancreatic carcinoma, prostate carcinoma, colorectal carcinoma, and hepatocellular carcinoma.

In some embodiments, provided herein are methods for the treatment or management of non-Hodgkin's lymphomas, including but not limited to, diffuse large B-cell lymphoma (DLBCL), using prognostic factors.

In some embodiments, provided herein are methods for the use of gene and protein biomarkers as a predictor of clinical sensitivity to lymphoma, non-Hodgkin's lymphoma, multiple myeloma, leukemia, AML, and/or solid tumors and patient response to treatment with 3-(5-amino-2-methyl-4-oxo-4H-quinazolin-3-yl)-piperidine-2,6-dione, or an enantiomer or a mixture of enantiomers thereof, or a pharmaceutically acceptable salt, solvate, hydrate, co-crystal, clathrate, or polymorph thereof.

The methods provided herein encompass methods for screening or identifying cancer patients, e.g., lymphoma, non-Hodgkin's lymphoma, multiple myeloma, leukemia, AML, and solid tumor patients, for treatment with 3-(5-amino-2-methyl-4-oxo-4H-quinazolin-3-yl)-piperidine-2,6-dione, or an enantiomer or a mixture of enantiomers thereof, or a pharmaceutically acceptable salt, solvate, hydrate, co-crystal, clathrate, or polymorph thereof. In particular, provided herein are methods for selecting patients having a higher response rate to therapy with 3-(5-amino-2-methyl-4-oxo-4H-quinazolin-3-yl)-piperidine-2,6-dione.

In one embodiment, provided herein is a method of predicting tumor response to treatment in a lymphoma, non-Hodgkin's lymphoma, multiple myeloma, leukemia, AML or solid tumor patient, the method comprising obtaining tumor tissue from the patient, purifying protein or RNA from the tumor, and measuring the presence or absence of a biomarker by, e.g., protein or gene expression analysis. The expression monitored may be, for example, mRNA expression or protein expression.

In certain embodiments, the biomarker is a gene associated with an activated B-cell phenotype of DLBCL. The genes are selected from the group consisting of IRF4/MUM1, FOXP1, SPIB, CARD11 and BLIMP/PDRM1. In one embodiment, the biomarker is NF-κB.

In one embodiment, the mRNA or protein is purified from the tumor and the presence or absence of a biomarker is measured by gene or protein expression analysis. In certain embodiments, the presence or absence of a biomarker is measured by quantitative real-time PCR (QRT-PCR), microarray, flow cytometry or immunofluorescence. In other embodiments, the presence or absence of a biomarker is measured by enzyme-linked immunosorbent assay-based methodologies (ELISA) or other similar methods known in the art.

In another embodiment, provided herein is a method of predicting tumor response to treatment in a non-Hodgkin's lymphoma patient, the method comprising obtaining tumor cells from the patient, culturing the cells in the presence or absence of 3-(5-amino-2-methyl-4-oxo-4H-quinazolin-3-yl)-piperidine-2,6-dione, purifying protein or RNA from the cultured cells, and measuring the presence or absence of a biomarker by, e.g., protein or gene expression analysis. The expression monitored may be, for example, mRNA expression or protein expression.

In another embodiment, provided herein is a method of monitoring tumor response to 3-(5-amino-2-methyl-4-oxo-4H-quinazolin-3-yl)-piperidine-2,6-dione treatment in a lymphoma, non-Hodgkin's lymphoma, multiple myeloma, leukemia, AML or solid tumor patient. The method comprises obtaining a biological sample from the patient, measuring the expression of a biomarker in the biological sample, administering 3-(5-amino-2-methyl-4-oxo-4H-quinazolin-3-yl)-piperidine-2,6-dione to the patient, thereafter obtaining a second biological sample from the patient, measuring biomarker expression in the second biological sample, and comparing the levels of expression, where an increased level of biomarker expression after treatment indicates the likelihood of an effective tumor response. In one embodiment, a decreased level of biomarker expression after treatment indicates the likelihood of effective tumor response. The biomarker expression monitored can be, for example, mRNA expression or protein expression. The expression in the treated sample can increase, for example, by about 1.5×, 2.0×, 3×, 5×, or more.

In yet another embodiment, a method for monitoring patient compliance with a drug treatment protocol is provided. The method comprises obtaining a biological sample from the patient, measuring the expression level of at least one biomarker in the sample, and determining if the expression level is increased or decreased in the patient sample compared to the expression level in a control untreated sample, wherein an increased or decreased expression indicates patient compliance with the drug treatment protocol. In one embodiment, the expression of one or more biomarkers is increased. The biomarker expression monitored can be, for example, mRNA expression or protein expression. The expression in the treated sample can increase, for example, by about 1.5×, 2.0×, 3×, 5×, or more.

In another embodiment, provided herein is a method of predicting the sensitivity to treatment 3-(5-amino-2-methyl-4-oxo-4H-quinazolin-3-yl)-piperidine-2,6-dione in a lymphoma, non-Hodgkin's lymphoma, multiple myeloma, leukemia, AML or solid tumor patient. In one embodiment, the patient is a non-Hodgkin's lymphoma patient, specifically, a DLBCL patient. The method comprises obtaining a biological sample from the patient, optionally isolating or purifying mRNA from the biological sample, amplifying the mRNA transcripts by, e.g., RT-PCR, where a higher baseline level of a specific biomarker indicates a higher likelihood that the cancer will be sensitive to treatment with 3-(5-amino-2-methyl-4-oxo-4H-quinazolin-3-yl)-piperidine-2,6-dione. In certain embodiments, the biomarker is a gene associated with an activated B-cell phenotype. The genes are selected from the group consisting of IRF4/MUM1, FOXP1, SPIB, CARD11 and BLIMP/PDRM1.

Also provided herein are methods for the treatment or management of cancer with 3-(5-amino-2-methyl-4-oxo-4H-quinazolin-3-yl)-piperidine-2,6-dione using CRBN as a predictive or prognostic factor. In certain embodiments, provided herein are methods for screening or identifying cancer patients for treatment with 3-(5-amino-2-methyl-4-oxo-4H-quinazolin-3-yl)-piperidine-2,6-dione using CRBN levels as a predictive or prognostic factor. In some embodiments, provided herein are methods for selecting patients having a higher response rate to therapy with 3-(5-amino-2-methyl-4-oxo-4H-quinazolin-3-yl)-piperidine-2,6-dione using CRBN levels as a predictive or prognostic factor.

In one embodiment, provided herein is a method of predicting patient response to treatment of cancer with 3-(5-amino-2-methyl-4-oxo-4H-quinazolin-3-yl)-piperidine-2,6-dione, the method comprising obtaining biological material from the patient, and measuring the presence or absence of CRBN.

In one embodiment, the method comprises obtaining cancer cells from the patient, culturing the cells in the presence or absence of 3-(5-amino-2-methyl-4-oxo-4H-quinazolin-3-yl)-piperidine-2,6-dione, purifying protein or RNA from the cultured cells, and measuring the presence or absence of a biomarker by, e.g., protein or gene expression analysis. The expression monitored may be, for example, mRNA expression or protein expression. In one embodiment, the cancer is lymphoma, leukemia, multiple myeloma, solid tumor, non-Hodgkin's lymphoma or melanoma.

In another embodiment, provided herein is a method of monitoring tumor response to drug treatment in a cancer patient. The method comprises obtaining a biological sample from the patient, measuring the expression of a biomarker in the biological sample, administering one or more drugs to the patient, thereafter obtaining a second biological sample from the patient, measuring biomarker expression in the second biological sample, and comparing the levels of expression, where an increased level of biomarker expression after treatment indicates the likelihood of an effective tumor response. In one embodiment, the cancer patient is a lymphoma, leukemia, multiple myeloma, solid tumor, non-Hodgkin's lymphoma or melanoma patient.

In one embodiment, a decreased level of biomarker expression after treatment indicates the likelihood of effective tumor response. The biomarker expression monitored can be, for example, mRNA expression or protein expression. The expression in the treated sample can increase, for example, by about 1.5×, 2.0×, 3×, 5×, or more. In one embodiment, the tumor is a lymphoma, leukemia, multiple myeloma, solid tumor, non-Hodgkin's lymphoma or melanoma.

In another embodiment, provided herein is a method of predicting the sensitivity to drug treatment in a cancer patient, specifically, a multiple myeloma or non-Hodgkin's lymphoma patient. The method comprises obtaining a biological sample from the patient, optionally isolating or purifying mRNA from the biological sample, amplifying the mRNA transcripts by, e.g., RT-PCR, where a higher baseline level of a specific biomarker indicates a higher likelihood that the cancer will be sensitive to treatment with a drug. In certain embodiments, the biomarker is a gene or protein associated with multiple myeloma or non-Hodgkin's lymphoma. In one embodiment, the genes are those associated with CRBN and are selected from the group consisting of DDB1, DDB2, GSK3B, CUL4A, CUL4B, XBP-1, FAS1, RANBP6, DUS3L, PHGDH, AMPK, IRF4 and NFκB. In another embodiment, the genes are selected from the group consisting of DDB1, DDB2, IRF4 and NFκB.

In one embodiment, identifying a patient having lymphoma, leukemia, multiple myeloma, a solid tumor, non-Hodgkin's lymphoma, diffuse large B-cell lymphoma or melanoma sensitive to treatment with 3-(5-amino-2-methyl-4-oxo-4H-quinazolin-3-yl)-piperidine-2,6-dione; identification of a gene or protein associated with CRBN wherein the presence of the gene or protein associated with CRBN is indicative of lymphoma, leukemia, multiple myeloma, a solid tumor, non-Hodgkin's lymphoma, diffuse large B-cell lymphoma or melanoma sensitive to treatment with 3-(5-amino-2-methyl-4-oxo-4H-quinazolin-3-yl)-piperidine-2,6-dione. In one embodiment, the gene or protein associated with CRBN is selected from the group consisting of DDB1, DDB2, IRF4 and NFκB.

In one embodiment, identifying a patient having lymphoma, leukemia, multiple myeloma, a solid tumor, non-Hodgkin's lymphoma or melanoma sensitive to treatment with 3-(5-amino-2-methyl-4-oxo-4H-quinazolin-3-yl)-piperidine-2,6-dione comprises measuring the level of CRBN activity in the patient. In another embodiment, measuring the level of CRBN activity in the patient comprises measuring DDB1, DDB2, IRF4 and/or NFκB in cells obtained from the patient.

In one embodiment, provided herein is a method for treating or managing non-Hodgkin's lymphoma, comprising:
(i) identifying a patient having lymphoma, non-Hodgkin's lymphoma, multiple myeloma, leukemia, AML or a solid tumor sensitive to treatment with 3-(5-amino-2-methyl-4-oxo-4H-quinazolin-3-yl)-piperidine-2,6-dione; and
(ii) administering to the patient a therapeutically effective amount of 3-(5-amino-2-methyl-4-oxo-4H-quinazolin-3-yl)-piperidine-2,6-dione, or a pharmaceutically acceptable salt or solvate (e.g., hydrate) thereof.

In one embodiment, the patient has non-Hodgkin's lymphoma. In one embodiment, the non-Hodgkin's lymphoma is diffuse large B-cell lymphoma. In another embodiment, the non-Hodgkin's lymphoma is of the activated B-cell phenotype.

In one embodiment, identifying a patient having non-Hodgkin's lymphoma sensitive to treatment with 3-(5-amino-2-methyl-4-oxo-4H-quinazolin-3-yl)-piperidine-2,6-dione comprises identification of a gene associated with the activated B-cell phenotype. In one embodiment, the gene associated with the activated B-cell phenotype is selected from the group consisting of IRF4/MUM1, FOXP1, SPIB, CARD11 and BLIMP/PDRM1.

In one embodiment, identifying a patient having non-Hodgkin's lymphoma sensitive to treatment with 3-(5-amino-2-methyl-4-oxo-4H-quinazolin-3-yl)-piperidine-2,6-dione comprises measuring the level of NF-κB activity in the patient. In another embodiment, measuring the level of NF-κB activity in the patient comprises measuring the baseline NF-κB activity level in tumor cells obtained from the patient.

Also provided herein are kits useful for predicting the likelihood of an effective lymphoma, non-Hodgkin's lymphoma, multiple myeloma, leukemia, AML or solid tumor treatment or for monitoring the effectiveness of a treatment with 3-(5-amino-2-methyl-4-oxo-4H-quinazolin-3-yl)-piperidine-2,6-dione. The kit comprises a solid support, and a means for detecting the protein expression of at least one biomarker in a biological sample. Such a kit may employ, for example, a dipstick, a membrane, a chip, a disk, a test strip, a filter, a microsphere, a slide, a multiwell plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide. The biological sample can be, for example, a cell culture, a cell line, a tissue, an oral tissue, gastrointestinal tissue, an organ, an organelle, a biological fluid, a blood sample, a urine sample, or a skin sample. The biological sample can be, for example, a lymph node biopsy, a bone marrow biopsy, or a sample of peripheral blood tumor cells.

In an additional embodiment, provided herein is a kit useful for predicting the likelihood of an effective treatment or for monitoring the effectiveness of a treatment with 3-(5-amino-2-methyl-4-oxo-4H-quinazolin-3-yl)-piperidine-2,6-dione. The kit comprises a solid support, nucleic acids contacting the support, where the nucleic acids are complementary to at least 20, 50, 100, 200, 350, or more bases of mRNA, and a means for detecting the expression of the mRNA in a biological sample.

In another embodiment, provided herein is a kit useful for predicting the likelihood of an effective treatment or for monitoring the effectiveness of a treatment with 3-(5-amino-2-methyl-4-oxo-4H-quinazolin-3-yl)-piperidine-2,6-dione. The kit comprises a solid support, at least one nucleic acid contacting the support, where the nucleic acid is complementary to at least 20, 50, 100, 200, 350, 500, or more bases of mRNA, and a means for detecting the expression of the mRNA in a biological sample.

In certain embodiments, the kits provided herein employ means for detecting the expression of a biomarker by quantitative real-time PCR (QRT-PCR), microarray, flow cytometry or immunofluorescence. In other embodiments, the expression of the biomarker is measured by ELISA-based methodologies or other similar methods known in the art.

Also provided herein are pharmaceutical compositions comprising about 1 to 1,000 mg of 3-(5-amino-2-methyl-4-oxo-4H-quinazolin-3-yl)-piperidine-2,6-dione, or an enantiomer or a mixture of enantiomers thereof, or a pharmaceutically acceptable salt, solvate, hydrate, co-crystal, clathrate, or polymorph thereof.

Further provided herein are pharmaceutical compositions comprising about 1 to 1,000 mg of 3-(5-amino-2-methyl-4-oxo-4H-quinazolin-3-yl)-piperidine-2,6-dione, or an enantiomer or a mixture of enantiomers thereof, or a pharmaceutically acceptable salt, solvate, hydrate, co-crystal, clathrate, or polymorph thereof; and one or more additional active ingredient. In certain embodiments, the one or more additional active ingredients are selected from oblimersen, melphalan, G-CSF, GM-CSF, EPO, a cox-2 inhibitor, topotecan, pentoxifylline, ciprofloxacin, taxotere, iritotecan, dexamethasone, doxorubicin, vincristine, IL 2, IFN, dacarbazine, Ara-C, vinorelbine and isotretinoin.

Also provided herein are kits useful for predicting the likelihood of an effective lymphoma, leukemia, multiple myeloma, a solid tumor, non-Hodgkin's lymphoma, diffuse large B-cell lymphoma or melanoma treatment or for monitoring the effectiveness of a treatment with one or more drugs, e.g., 3-(5-amino-2-methyl-4-oxo-4H-quinazolin-3-yl)-piperidine-2,6-dione. The kit comprises a solid support, and a means for detecting the protein expression of at least one biomarker in a biological sample. Such a kit may employ, for example, a dipstick, a membrane, a chip, a disk, a test strip, a filter, a microsphere, a slide, a multiwell plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide. The biological sample can be, for example, a cell culture, a cell line, a tissue, an oral tissue, gastrointestinal tissue, an organ, an organelle, a biological fluid, a blood sample, a urine sample, or a skin sample. The biological sample can be, for example, a lymph node biopsy, a bone marrow biopsy, or a sample of peripheral blood tumor cells.

In another embodiment, the kit comprises a solid support, nucleic acids contacting the support, where the nucleic acids are complementary to at least 20, 50, 100, 200, 350, or more bases of mRNA, and a means for detecting the expression of the mRNA in a biological sample.

In certain embodiments, the kits provided herein employ means for detecting the expression of a biomarker by quantitative real-time PCR (QRT-PCR), microarray, flow cytometry or immunofluorescence. In other embodiments, the expression of the biomarker is measured by ELISA-based methodologies or other similar methods known in the art.

Also provided herein is a kit comprising (i) a pharmaceutical composition comprising 3-(5-amino-2-methyl-4-oxo-4H-quinazolin-3-yl)-piperidine-2,6-dione, or an enantiomer or a mixture of enantiomers thereof, or a pharmaceutically acceptable salt, solvate, hydrate, co-crystal, clathrate, or polymorph thereof; and (ii) a pharmaceutical composition comprising hematopoietic growth factor, cytokine, anti-cancer agent, antibiotic, a cox-2 inhibitor, immunomodulatory agent, immunosuppressive agent, corticosteroid, or a pharmacologically active mutant or derivative thereof, or a combination thereof.

In one embodiment, provided herein is a kit comprising (i) a pharmaceutical composition comprising 3-(5-amino-2-methyl-4-oxo-4H-quinazolin-3-yl)-piperidine-2,6-dione, or an enantiomer or a mixture of enantiomers thereof, or a pharmaceutically acceptable salt, solvate, hydrate, co-crystal, clathrate, or polymorph thereof and (ii) a pharmaceutical composition comprising oblimersen, melphalan, G-CSF, GM-CSF, EPO, a cox-2 inhibitor, topotecan, pentoxifylline, taxotere, iritotecan, ciprofloxacin, dexamethasone, doxorubicin, vincristine, IL 2, IFN, dacarbazine, Ara-C, vinorelbine, or isotretinoin.

In another embodiment, provided herein is a kit comprising (i) a pharmaceutical composition comprising 3-(5-amino-2-methyl-4-oxo-4H-quinazolin-3-yl)-piperidine-2,6-dione, or an enantiomer or a mixture of enantiomers thereof, or a pharmaceutically acceptable salt, solvate, hydrate, co-crystal, clathrate, or polymorph thereof and (ii) umbilical cord blood, placental blood, peripheral blood stem cell, hematopoietic stem cell preparation or bone marrow.

4. BRIEF DESCRIPTION OF THE FIGURES

FIGS. 1A to 1D: Inhibitory effect of 3-(5-amino-2-methyl-4-oxo-4H-quinazolin-3-yl)-piperidine-2,6-dione (Comp. Formula I) on NFκB activity in DLBCL cells.

Figure 2:
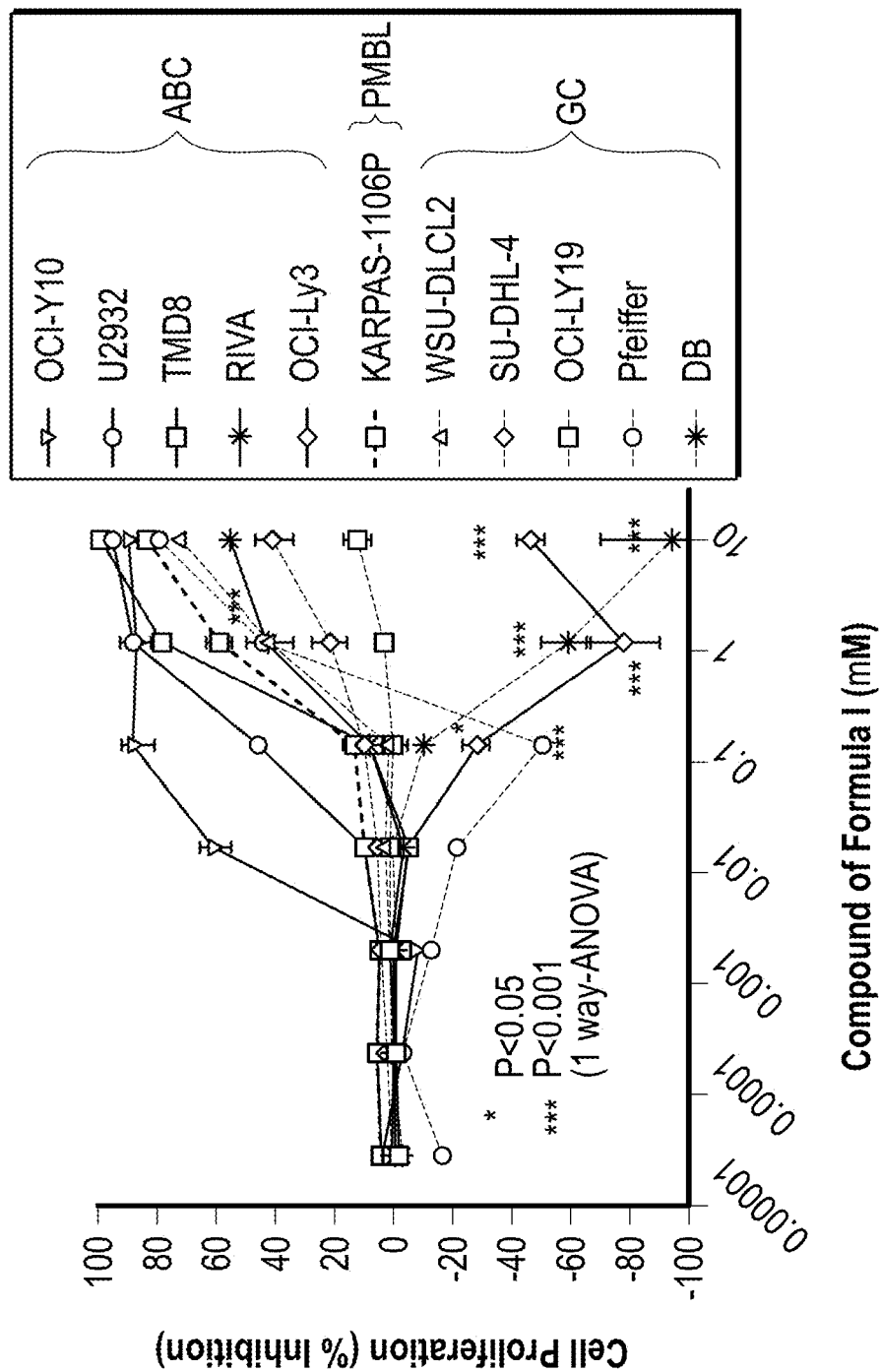

FIG. 2: Antiproliferative effect of 3-(5-amino-2-methyl-4-oxo-4H-quinazolin-3-yl)-piperidine-2,6-dione (Compound of Formula I) in an in vitro DLBCL cell-based assay.

Figure 3:
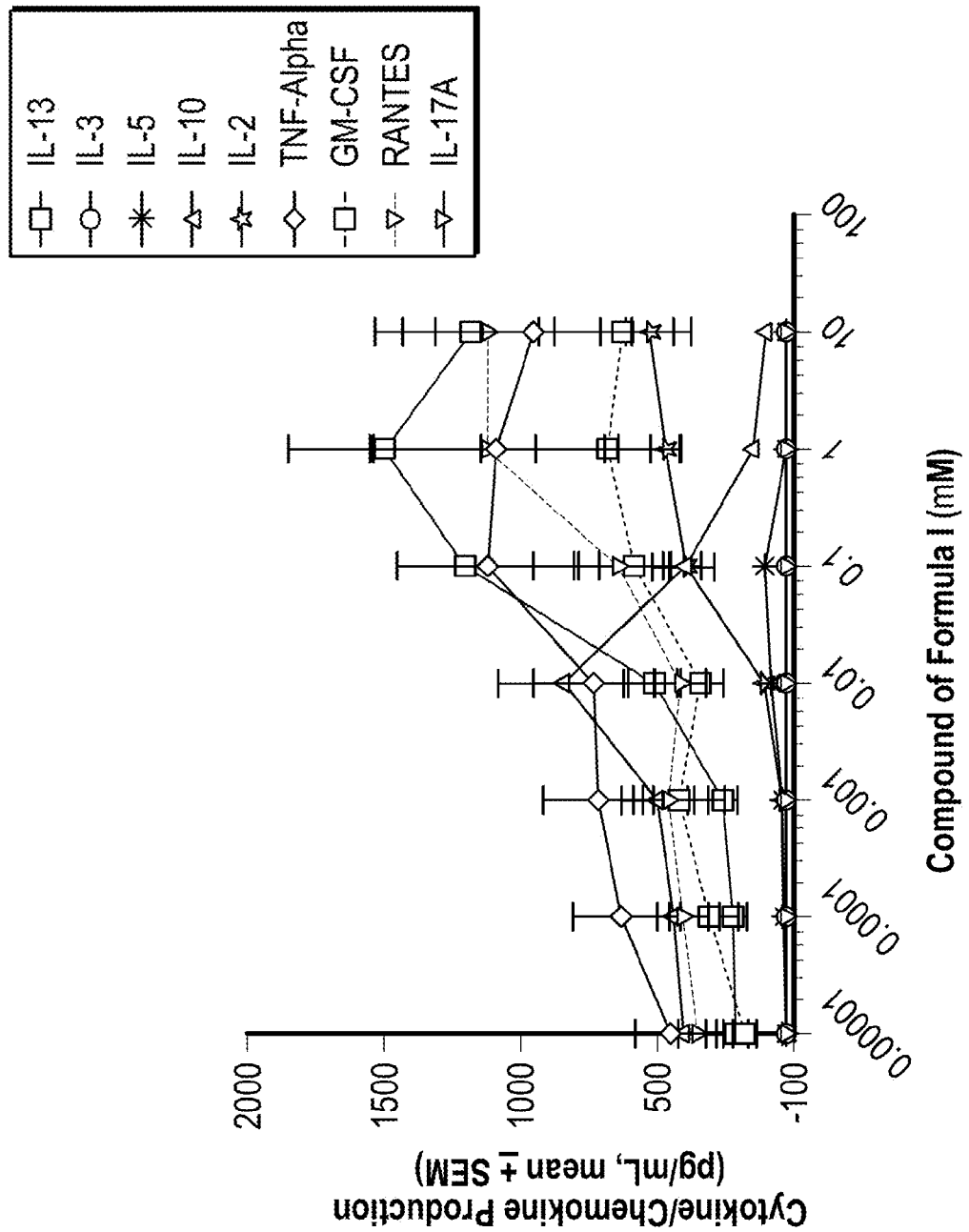

FIG. 3: 3-(5-amino-2-methyl-4-oxo-4H-quinazolin-3-yl)-piperidine-2,6-dione (Compound of Formula I) costimulates T cells and enhances cytokine production.

Figure 4:
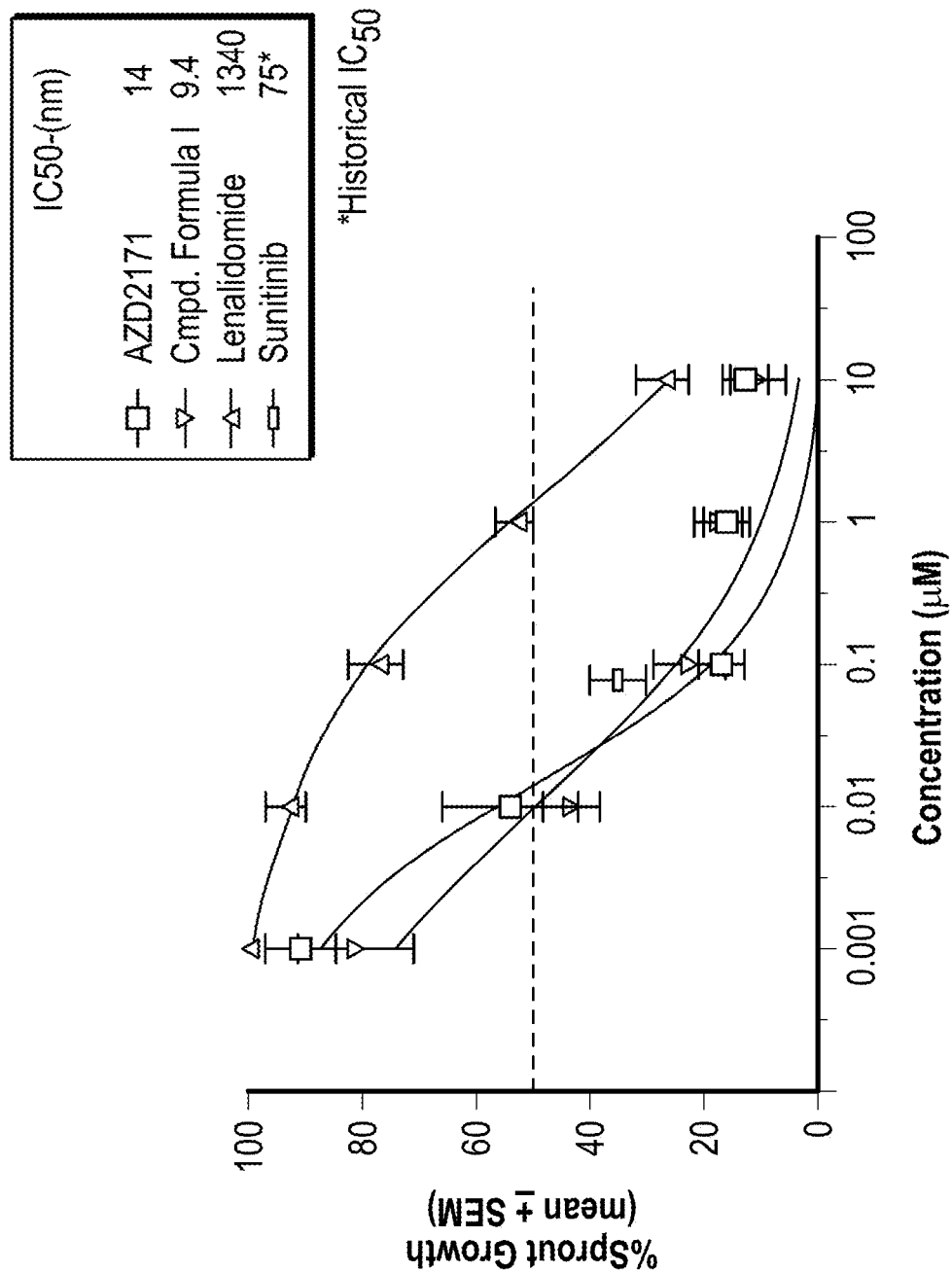

FIG. 4: Anti-angiogenic effect of 3-(5-amino-2-methyl-4-oxo-4H-quinazolin-3-yl)-piperidine-2,6-dionein an in vitro human umbiligcal expant assay.

Figure 5A:
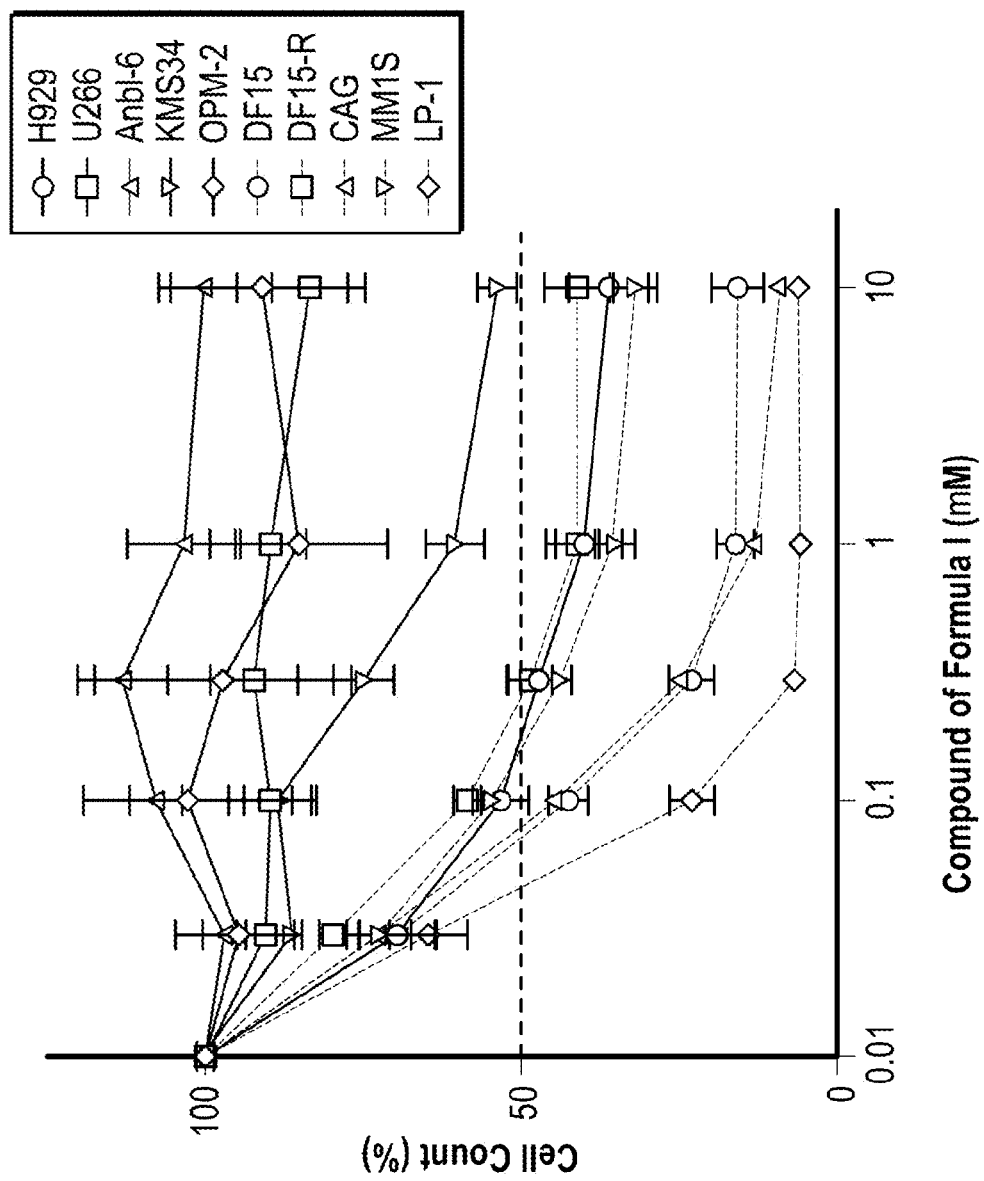
Figure 5B:
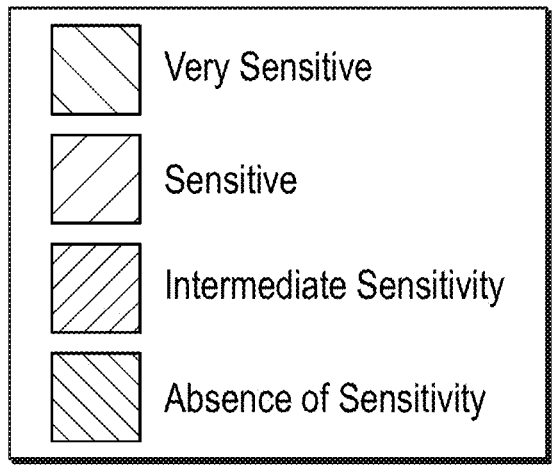

FIGS. 5A & 5B: Antiproliferative effect of 3-(5-amino-2-methyl-4-oxo-4H-quinazolin-3-yl)-piperidine-2,6-dione in an in vitro multiple myleoma (MM) cell-based assay.

Figure 6:
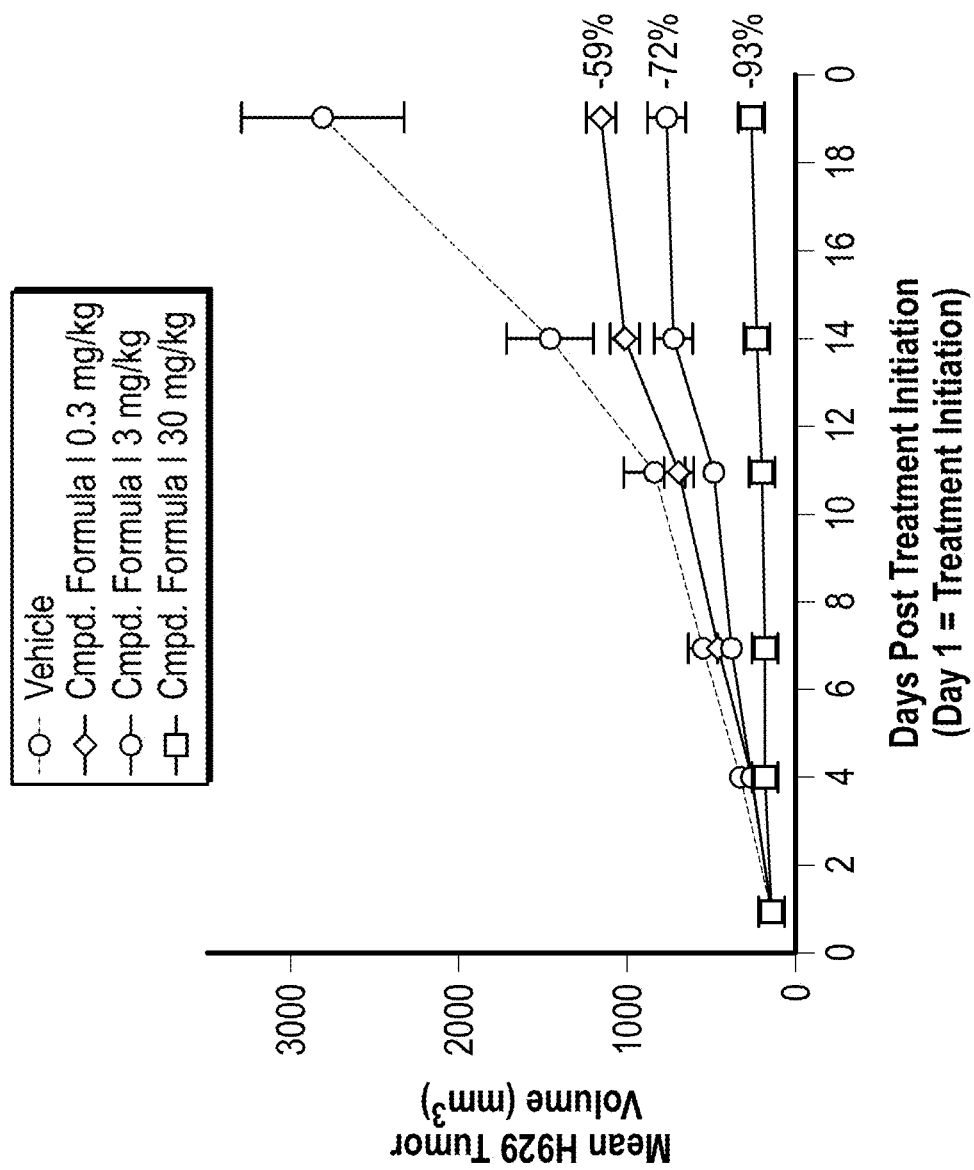

FIG. 6: In vitro tumor inhibition of Antiproliferative effect of 3-(5-amino-2-methyl-4-oxo-4H-quinazolin-3-yl)-piperidine-2,6-dione in a N929 xenograft model.

Figure 7A:
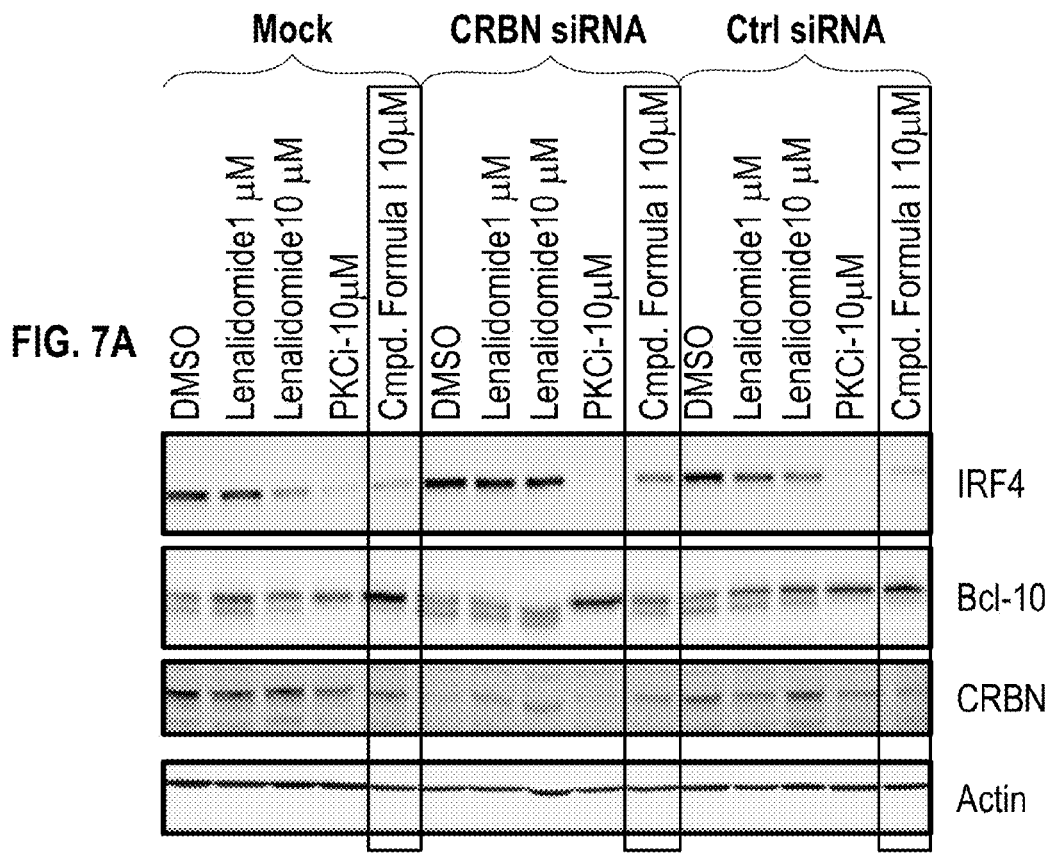
Figure 7B:
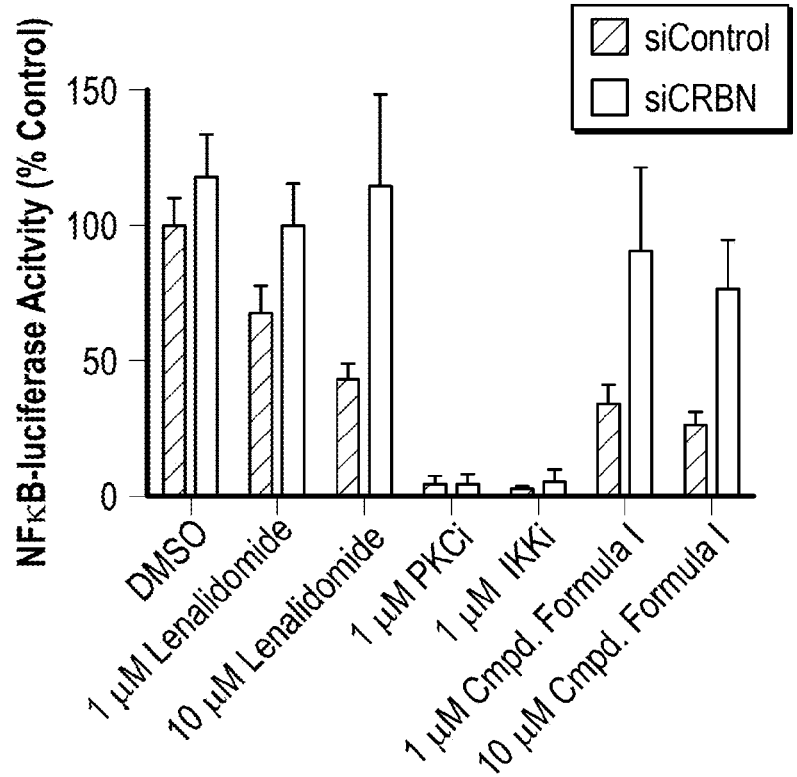
Figure 7C:
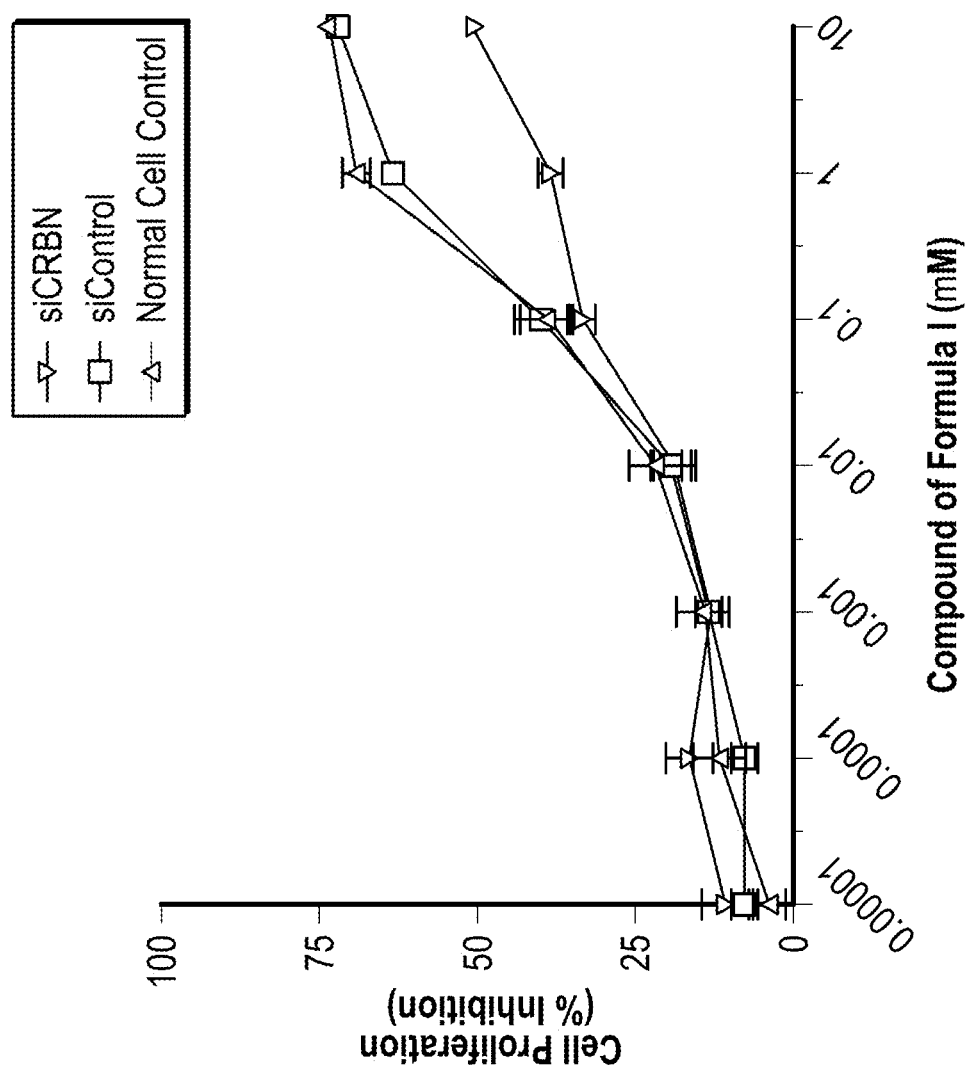

FIGS. 7A-7C: Cereblon expression modulates the effects of 3-(5-amino-2-methyl-4-oxo-4H-quinazolin-3-yl)-piperidine-2,6-dione in ABC-DLBCL cell lines.

Figure 8:
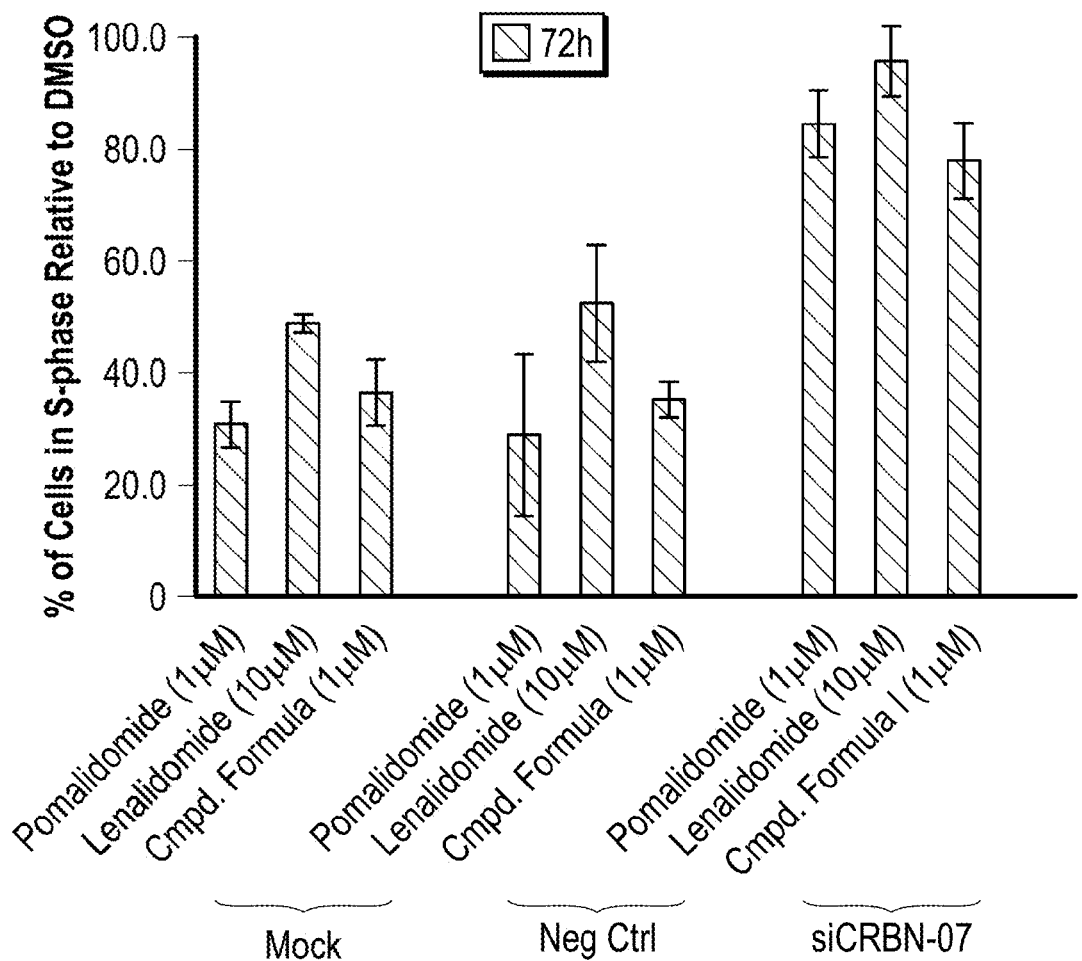

FIG. 8: Knockdown of CRBN abrogated G1 arrest induced by 3-(5-amino-2-methyl-4-oxo-4H-quinazolin-3-yl)-piperidine-2,6-dione.

FIG. 9: CRBN knockdown abrogates effect of 3-(5-amino-2-methyl-4-oxo-4H-quinazolin-3-yl)-piperidine-2,6-dione on phosphorylation of pRb and IRF-4 in H929 cells.

Figure 10:
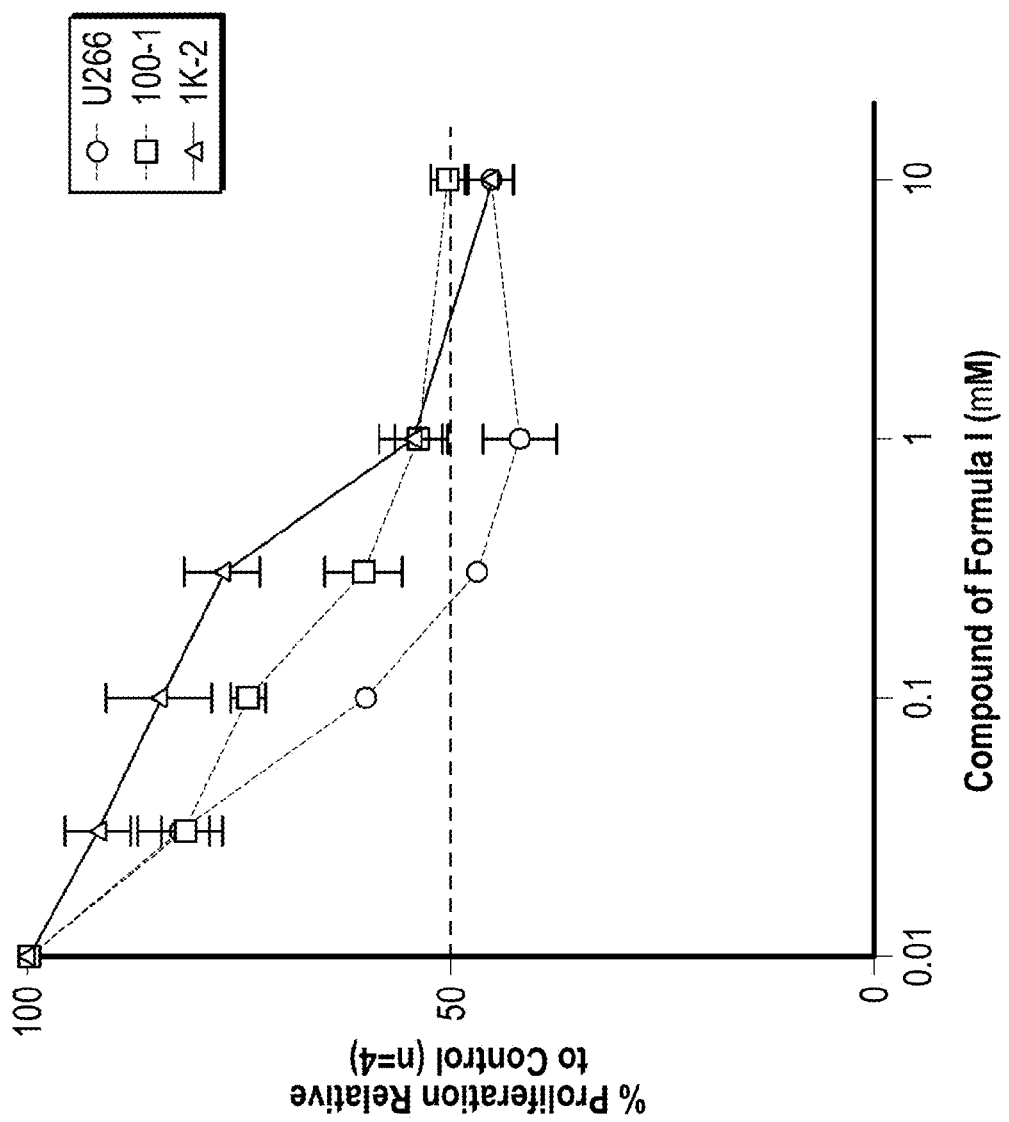

FIG. 10: Antiproliferative activity of 3-(5-amino-2-methyl-4-oxo-4H-quinazolin-3-yl)-piperidine-2,6-dione inhibits in CRBN-sensitive myeloma cells.

Figure 11:
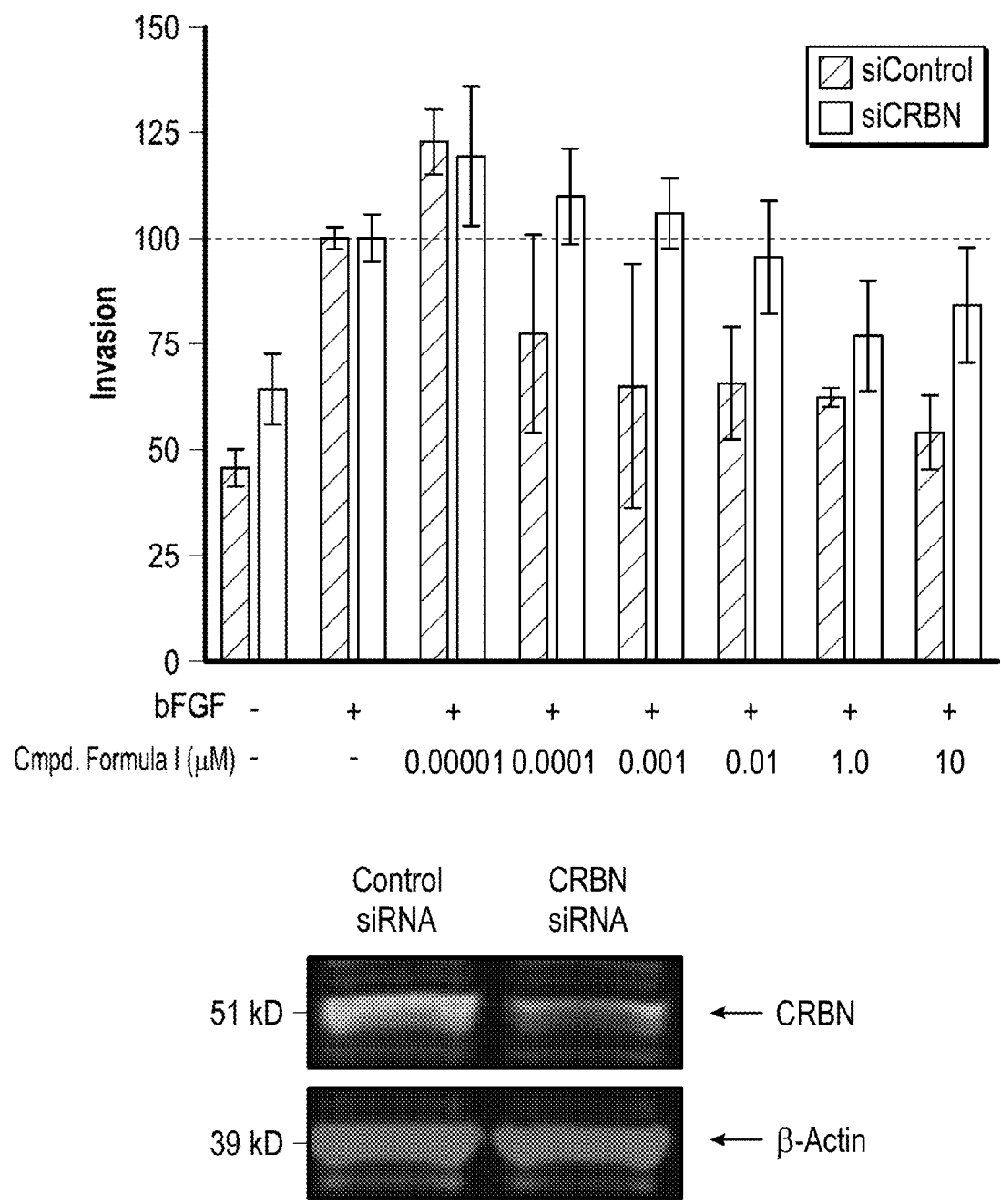
Figure 12A:
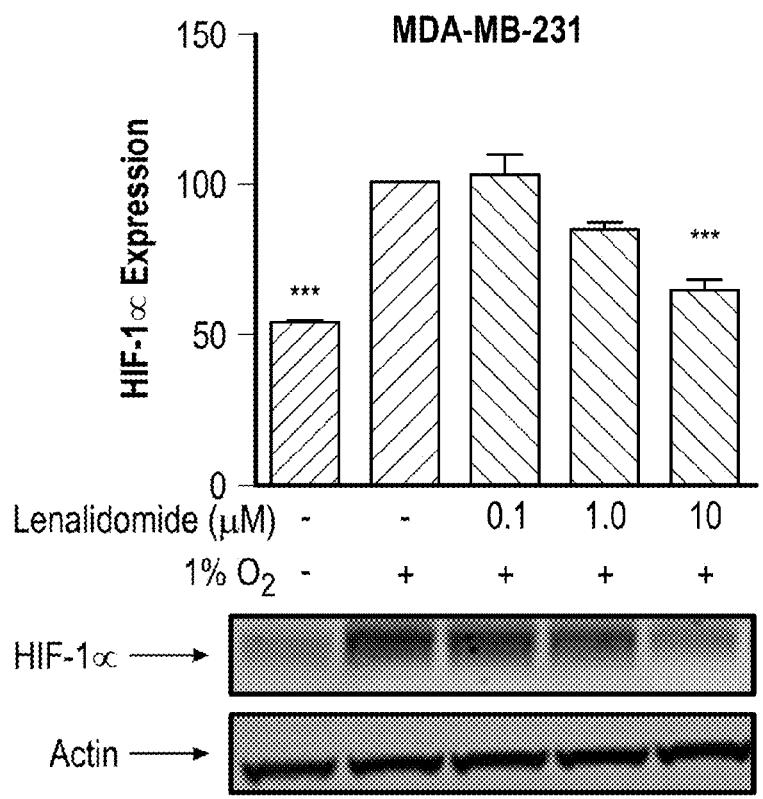
Figure 12B:
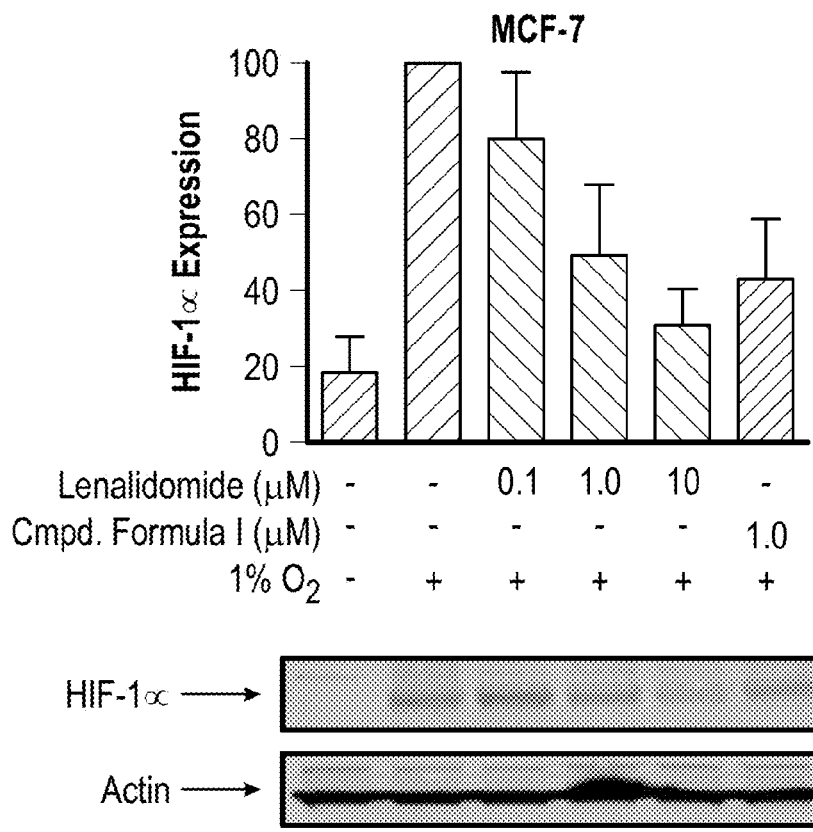
Figure 12C:
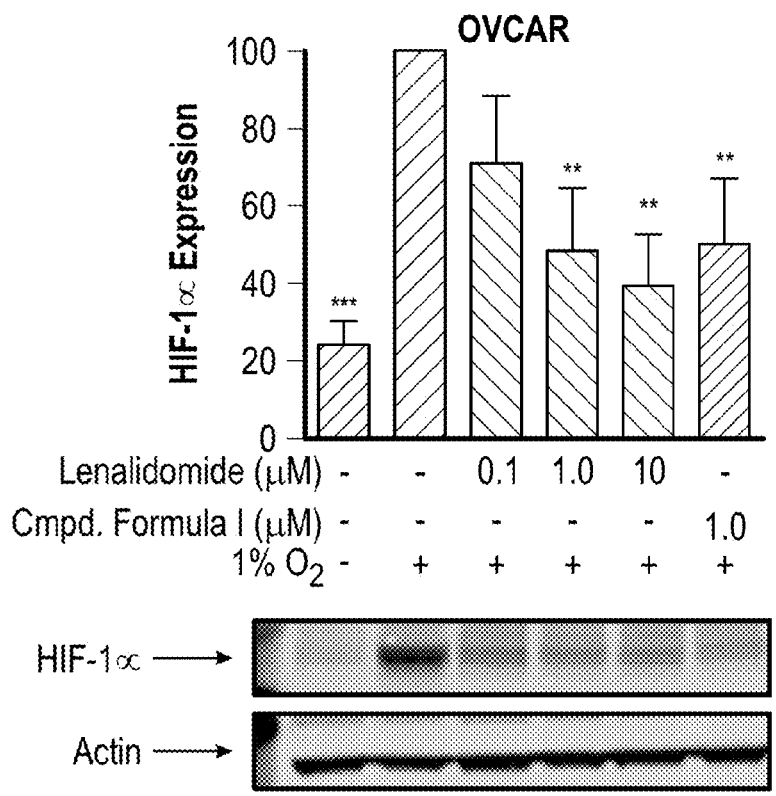
Figure 12D:
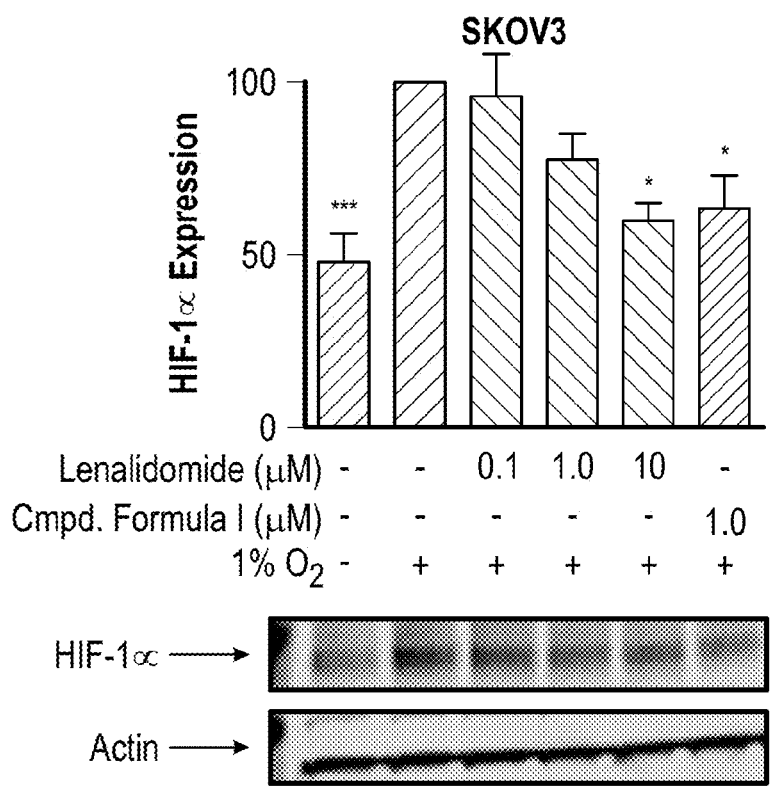
Figure 12E:
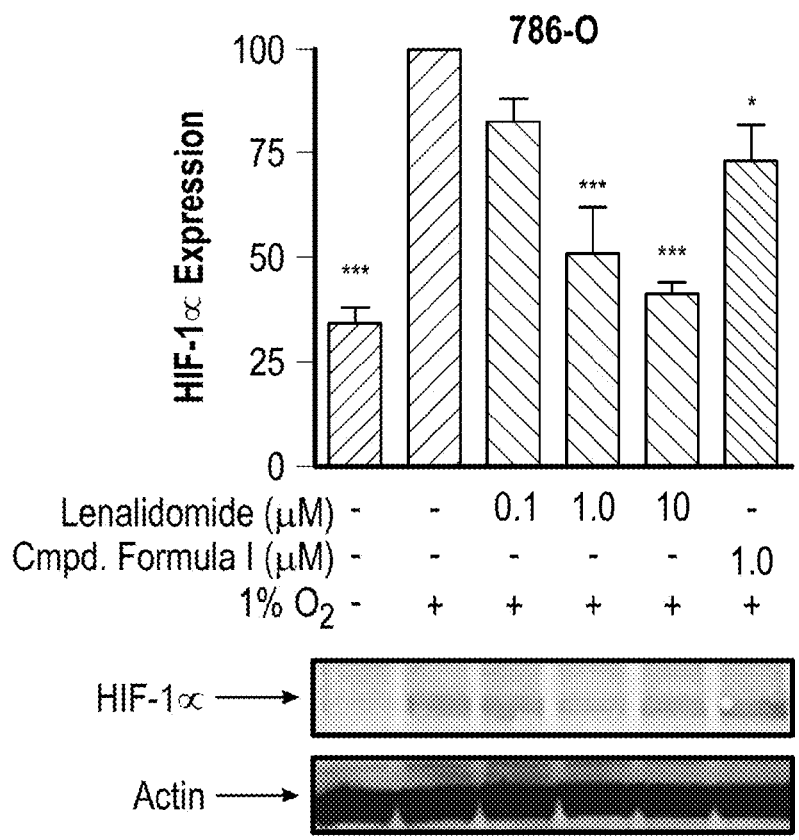
Figure 12F:
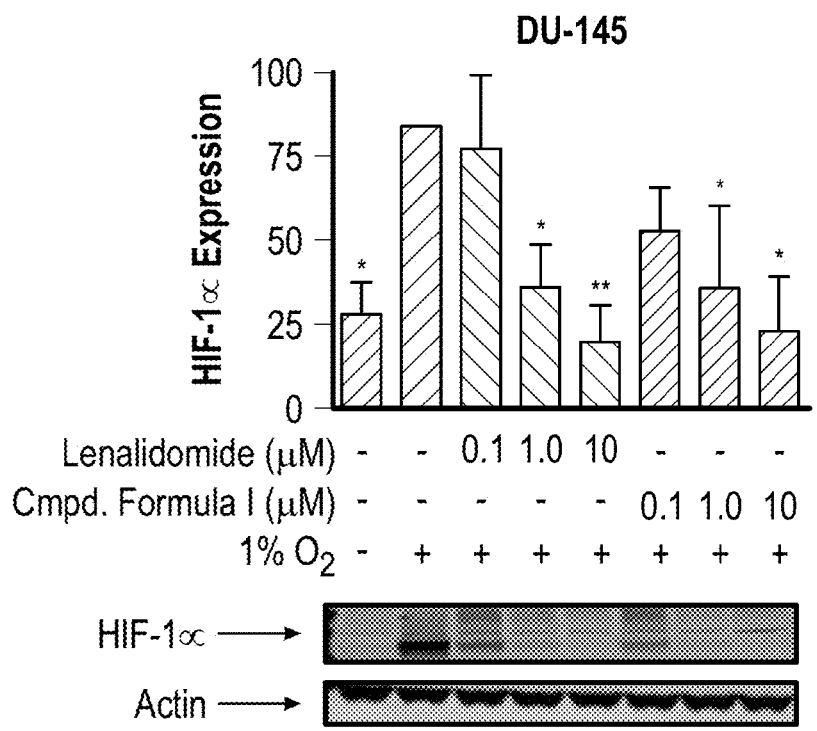
Figure 12G:
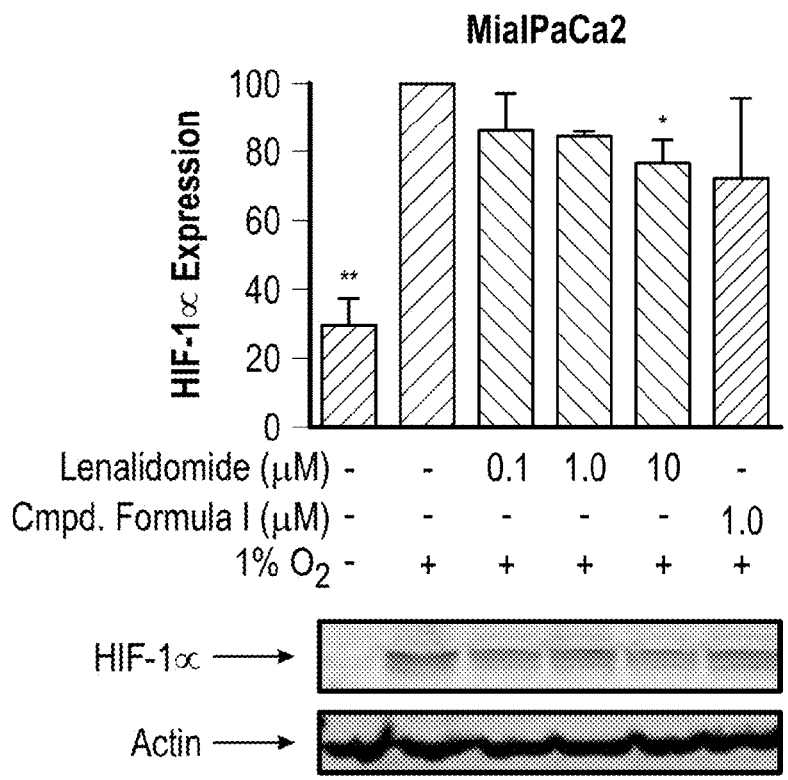
Figure 12H:
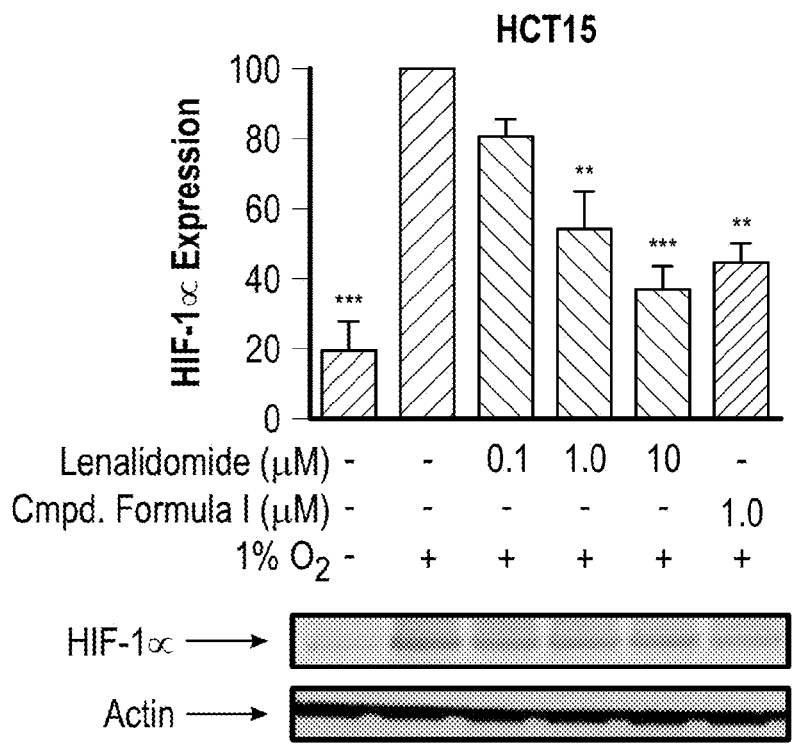
Figure 12I:
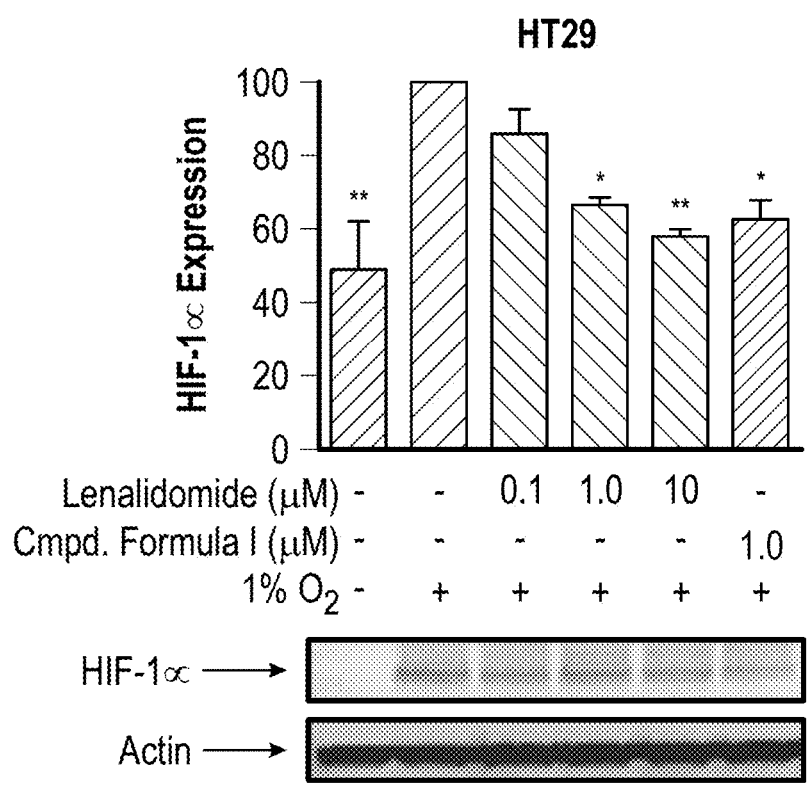

FIG. 11: Cereblon expression modulates anti-invasive activity of 3-(5-amino-2-methyl-4-oxo-4H-quinazolin-3-yl)-piperidine-2,6-dione.

FIGS. 12A-12I: 3-(5-amino-2-methyl-4-oxo-4H-quinazolin-3-yl)-piperidine-2,6-dione inhibits hypoxia-induced HIF1-α expression in solid tumor cell lines.

Figure 13A:
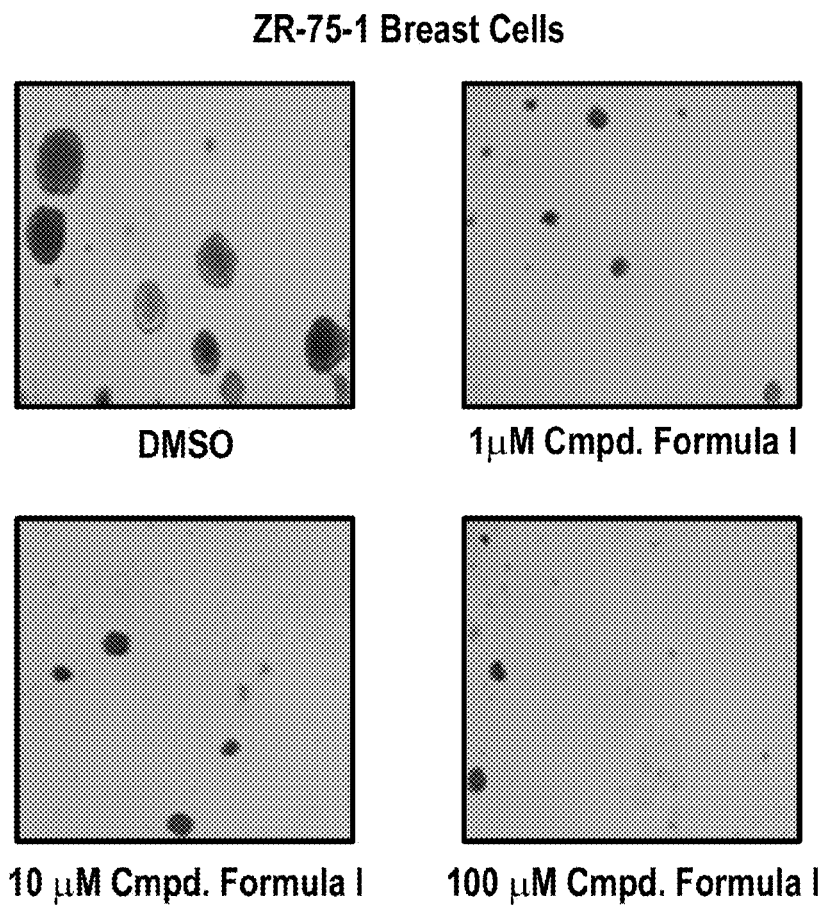
Figure 13B:
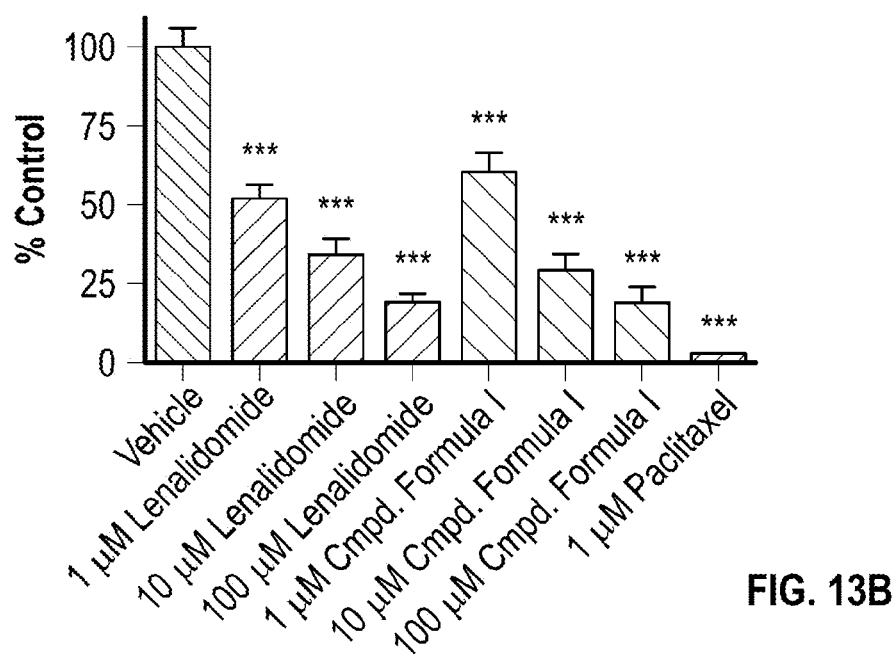

FIGS. 13A & 13B: 3-(5-amino-2-methyl-4-oxo-4H-quinazolin-3-yl)-piperidine-2,6-dione inhibits breast cancer cell colony formation.

Figure 14:
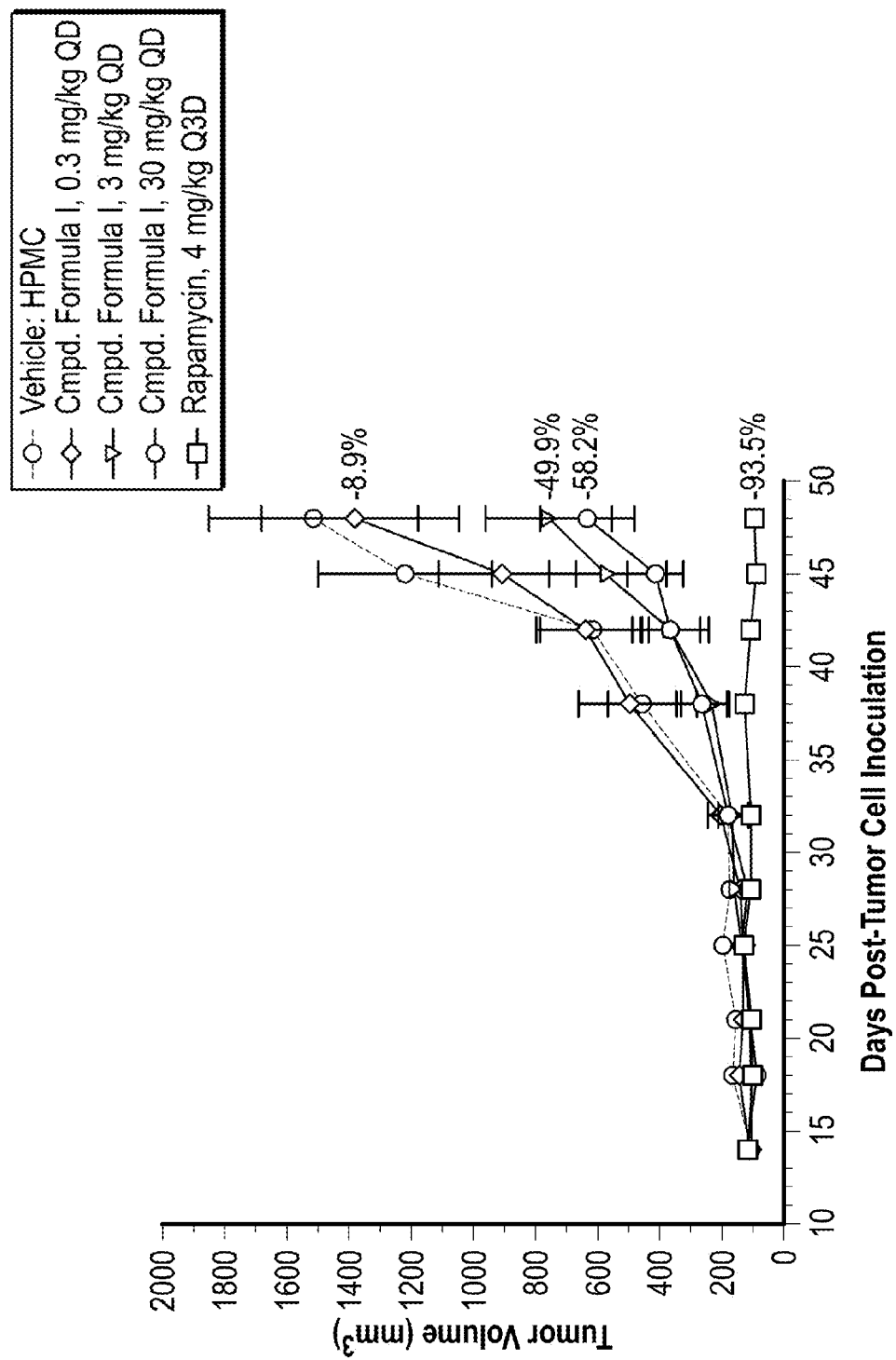

FIG. 14: 3-(5-amino-2-methyl-4-oxo-4H-quinazolin-3-yl)-piperidine-2,6-dione inhibits U87 glioblastoma tumor cell growth.

5. DETAILED DESCRIPTION OF THE INVENTION

Provided herein are methods of treating, managing, or preventing cancer, which comprise administering to a patient in need of such treatment, management, or prevention a therapeutically or prophylactically effective amount of 3-(5-amino-2-methyl-4-oxo-4H-quinazolin-3-yl)-piperidine-2,6-dione, or an enantiomer or a mixture of enantiomers thereof, or a pharmaceutically acceptable salt, solvate, hydrate, co-crystal, clathrate, or polymorph thereof as a single agent or as a part of a combination therapy.

In certain embodiments, 3-(5-amino-2-methyl-4-oxo-4H-quinazolin-3-yl)-piperidine-2,6-dione, or an enantiomer or a mixture of enantiomers thereof, or a pharmaceutically acceptable salt, solvate, hydrate, co-crystal, clathrate, or polymorph thereof, is administered in combination with one or more additional drugs (or "second active agents") for use in the treatment, management, or prevention of cancer. Second active agents include small molecules and large molecules (e.g., proteins and antibodies), some examples of which are provided herein, as well as stem cells. Methods or therapies, that can be used in combination with the administration of the compound provided herein include, but are not limited to, surgery, blood transfusions, immunotherapy, biological therapy, radiation therapy, and other non-drug based therapies presently used to treat, prevent or manage cancer. In certain embodiments, the compound provided herein may be used as a vaccine adjuvant.

In some embodiments, the methods provided herein are based, in part, on the discovery that the expression of certain genes or proteins associated with certain cancer cells may be utilized as biomarkers to indicate the effectiveness or progress of a disease treatment. Such cancers include, but are not limited to, lymphoma, non-Hodgkin's lymphoma, multiple myeloma, leukemia, acute myeloid leukemia (AML), and solid tumors. In certain embodiments, the cancer is of the activated B-cell phenotype in non-Hodgkin's lymphoma. In particular, these biomarkers can be used to predict, assess and track the effectiveness of patient treatment with 3-(5-amino-2-methyl-4-oxo-4H-quinazolin-3-yl)-piperidine-2,6-dione.

In some embodiments, the methods provided herein are based, in part, on the discovery that cereblon (CRBN) is associated with the anti-proliferative activities of certain drugs, such as 3-(5-amino-2-methyl-4-oxo-4H-quinazolin-3-yl)-piperidine-2,6-dione. In some embodiments, CRBN may be utilized as a biomarker to indicate the effectiveness or progress of a disease treatment with 3-(5-amino-2-methyl-4- oxo-4H-quinazolin-3-yl)-piperidine-2,6-dione. Without being bound by a particular theory, CRBN binding may contribute to or even be required for anti-proliferative or other activities of certain compounds, such as 3-(5-amino-2-methyl-4-oxo-4H-quinazolin-3-yl)-piperidine-2,6-dione Without being limited to a particular theory, 3-(5-amino-2-methyl-4-oxo-4H-quinazolin-3-yl)-piperidine-2,6-dione can mediate growth inhibition, apoptosis and inhibition of angiogenic factors in certain types of cancer such as lymphoma, non-Hodkin's lymphoma, multiple myeloma, leukemia, AML, and solid tumors. Upon examining the expression of several cancer-related genes in several cell types before and after the treatment with 3-(5-amino-2-methyl-4-oxo-4H-quinazolin-3-yl)-piperidine-2,6-dione, it was discovered that the expression levels of several cancer-related genes or proteins can be used as biomarkers for predicting and monitoring cancer treatments.

It was also discovered that the level of NF-κB activity is elevated in cells of the activated B-cell phenotype in non-Hodkin's lymphoma relative to other types of lymphoma cells, and that such cells may be sensitive to 3-(5-amino-2-methyl-4-oxo-4H-quinazolin-3-yl)-piperidine-2,6-dione treatment. This suggests that the baseline activity of NF-κB activity in lymphoma cells may be a predictive biomarker for 3-(5-amino-2-methyl-4-oxo-4H-quinazolin-3-yl)-piperidine-2,6-dione treatment in non-Hodgkin's lymphoma patients.

Therefore, in certain embodiments, provided herein are methods for predicting tumor response to treatment in a non-Hodkin's lymphoma patient. In one embodiment, provided herein is a method of predicting tumor response to treatment in a non-Hodgkin's lymphoma patient, the method comprising obtaining tumor tissue from the patient, purifying protein or RNA from the tumor, and measuring the presence or absence of a biomarker by, e.g., protein or gene expression analysis. The expression monitored may be, for example, mRNA expression or protein expression. In certain embodiments, the biomarker is a gene associated with an activated B-cell phenotype of DLBCL. The genes are selected from the group consisting of IRF4/MUM1, FOXP1, SPIB, CARD11 and BLIMP/PDRM1. In one embodiment, the biomarker is NF-κB.

In another embodiment, the method comprises obtaining tumor cells from the patient, culturing the cells in the presence or absence of 3-(5-amino-2-methyl-4-oxo-4H-quinazolin-3-yl)-piperidine-2,6-dione, purifying RNA or protein from the cultured cells, and measuring the presence or absence of a biomarker by, e.g., gene or protein expression analysis.

In certain embodiments, the presence or absence of a biomarker is measured by quantitative real-time PCR (QRT-PCR), microarray, flow cytometry or immunofluorescence. In other embodiments, the presence or absence of a biomarker is measured by ELISA-based methodologies or other similar methods known in the art.

The methods provided herein encompass methods for screening or identifying cancer patients, e.g., non-Hodgkin's lymphoma patients, for treatment with 3-(5-amino-2-methyl-4-oxo-4H-quinazolin-3-yl)-piperidine-2,6-dione. In particular, provided herein are methods for selecting patients having, or who are likely to have, a higher response rate to a therapy with 3-(5-amino-2-methyl-4-oxo-4H-quinazolin-3-yl)-piperidine-2,6-dione.

In one embodiment, the method comprises the identification of patients likely to respond to therapy by obtaining tumor cells from the patient, culturing the cells in the presence or absence of 3-(5-amino-2-methyl-4-oxo-4H-quinazolin-3-yl)-piperidine-2,6-dione, purifying RNA or protein from the cultured cells, and measuring the presence or absence of a specific biomarker. The expression monitored can be, for example, mRNA expression or protein expression. The expression in the treated sample can increase, or in some cases, decrease, for example, by about 1.5×, 2.0×, 3×, 5×, or more. In certain embodiments, the biomarker is a gene associated with an activated B-cell phenotype. The genes are selected from the group consisting of IRF4/MUM1, FOXP1, SPIB, CARD11 and BLIMP/PDRM1. In one embodiment, the biomarker is NF-κB. Baseline levels of expression of these genes can be predictive of the sensitivity of a cancer to treatment with 3-(5-amino-2-methyl-4-oxo-4H-quinazolin-3-yl)-piperidine-2,6-dione.

In one embodiment, IRF4/MUM1 expression in cancer cells, e.g., ABC-subtype lymphoma, can be decreased with the treatment of 3-(5-amino-2-methyl-4-oxo-4H-quinazolin-3-yl)-piperidine-2,6-dione. In some embodiments, IRF4 downregulation by 3-(5-amino-2-methyl-4-oxo-4H-quinazolin-3-yl)-piperidine-2,6-dione can be a potential pharmacodynamic biomarker.

In another embodiment, provided herein is a method of monitoring tumor response to treatment with 3-(5-amino-2-methyl-4-oxo-4H-quinazolin-3-yl)-piperidine-2,6-dione in a lymphoma, non-Hodgkin's lymphoma, multiple myeloma, leukemia, AML or a solid tumor patient. The method comprises obtaining a biological sample from the patient, measuring the expression of one or more biomarkers in the biological sample, administering 3-(5-amino-2-methyl-4-oxo-4H-quinazolin-3-yl)-piperidine-2,6-dione to the patient, thereafter obtaining a second biological sample from the patient, measuring biomarker expression in the second biological sample, and comparing the levels of biomarker expression, where an increased level of biomarker expression after treatment indicates the likelihood of an effective tumor response. In one embodiment, a decreased level of biomarker expression after treatment indicates the likelihood of effective tumor response. In certain embodiments, the biomarker is a gene associated with an activated B-cell phenotype of non-Hodgkin's lymphoma. The genes are selected from the group consisting of IRF4/MUM1, FOXP1, SPIB, CARD11 and BLIMP/PDRM1. In one embodiment, the biomarker is NF-κB.

In certain embodiments, the method comprises measuring the expression of one or more biomarkers genes associated with an activated B-cell phenotype. The genes are selected from the group consisting of IRF4/MUM1, FOXP1, SPIB, CARD11 and BLIMP/PDRM1. The expression monitored can be, for example, mRNA expression or protein expression. The expression in the treated sample can increase, for example, by about 1.5×, 2.0×, 3×, 5×, or more.

In yet another embodiment, a method for monitoring patient compliance with a drug treatment protocol is provided. The method comprises obtaining a biological sample from the patient, measuring the expression level of at least one biomarker in the sample, and determining if the expression level is increased or decreased in the patient sample compared to the expression level in a control untreated sample, wherein an increased or decreased expression indicates patient compliance with the drug treatment protocol. In one embodiment, the expression of one or more biomarker is increased. The expression monitored can be, for example, mRNA expression or protein expression. The expression in the treated sample can increase, for example, by about 1.5×, 2.0×, 3×, 5×, or more. In certain embodiments, the biomarker is a gene associated with an activated B-cell phenotype. The genes are selected from the group consisting of IRF4/MUM1, FOXP1, SPIB, CARD11 and BLIMP/PDRM1. In one embodiment, the biomarker is NF-κB.

In another embodiment, a method of predicting the sensitivity to treatment with 3-(5-amino-2-methyl-4-oxo-4H-quinazolin-3-yl)-piperidine-2,6-dione in a lymphoma, non-Hodgkin's lymphoma, multiple myeloma, leukemia, AML or a solid tumor patient is provided. In one embodiment, the patient is a non-Hodgkin's lymphoma patient, specifically, a DLBCL patient. The method comprises obtaining a biological sample from the patient, optionally isolating or purifying mRNA from the biological sample, amplifying the mRNA transcripts by, e.g., RT-PCR, where a higher baseline level of one or more specific biomarkers indicates a higher likelihood that the cancer will be sensitive to treatment with 3-(5-amino-2-methyl-4-oxo-4H-quinazolin-3-yl)-piperidine-2,6-dione. In one embodiment, the biomarker is a gene associated with an activated B-cell phenotype selected from the group consisting of IRF4/MUM1, FOXP1, SPIB, CARD11 and BLIMP/PDRM1.

In another embodiment, the method of predicting sensitivity to treatment with 3-(5-amino-2-methyl-4-oxo-4H-quinazolin-3-yl)-piperidine-2,6-dione in an NHL, e.g., a DLBCL patient, comprises obtaining a tumor sample from the patient, embedding the tumor sample into a paraffin-embedded, formalin-fixed block, and staining the sample with antibodies to CD20, CD10, bcl-6, IRF4/MUM1, bcl-2, cyclin D2, and/or FOXP1, as described in Hans et al., *Blood*, 2004, 103: 275-282, which is hereby incorporated by reference in its entirety. In one embodiment, CD10, bcl-6, and IRF4/MUM-1 staining can be used to divide DLBCL into GCB and non-GCB subgroups to predict an outcome.

In one embodiment, provided herein is a method for predicting tumor response to treatment in a non-Hodgkin's lymphoma patient, comprising:
(i) obtaining a biological sample from the patient;
(ii) measuring activity of the NF-κB pathway in the biological sample; and
(iii) comparing the level of NF-κB activity in the biological sample to that of a biological sample of a non-activated B-cell lymphoma subtype;
wherein an increased level of NF-κB activity relative to non-activated B-cell subtype lymphoma cells indicates a likelihood of an effective patient tumor response to 3-(5-amino-2-methyl-4-oxo-4H-quinazolin-3-yl)-piperidine-2,6-dione treatment.

In one embodiment, measuring activity of the NF-κB pathway in the biological sample comprises measuring the level of NF-κB in the biological sample.

In one embodiment, provided herein is a method of monitoring tumor response to treatment in a non-Hodgkin's lymphoma patient, comprising:
(i) obtaining a biological sample from the patient;
(ii) measuring the level of NF-κB activity in the biological sample;
(iii) administering a therapeutically effective amount of 3-(5-amino-2-methyl-4-oxo-4H-quinazolin-3-yl)-piperidine-2,6-dione, or a salt, solvate or hydrate thereof to the patient;
(iv) obtaining a second biological sample from the patient;
(v) measuring the level of NF-κB activity in the second biological sample; and
(vi) comparing the level of NF-κB activity in the first biological sample to that in the second biological sample;
wherein a decreased level of NF-κB activity in the second biological sample relative to the first biological sample indicates a likelihood of an effective patient tumor response.

In one embodiment, provided herein is a method for monitoring patient compliance with a drug treatment protocol in a non-Hodgkin's lymphoma patient, comprising:
(i) obtaining a biological sample from the patient;
(ii) measuring the level of NF-κB activity in the biological sample; and
(iii) comparing the level of NF-κB activity in the biological sample to a control untreated sample;
wherein a decreased level of NF-κB activity in the biological sample relative to the control indicates patient compliance with the drug treatment protocol.

In one embodiment, the non-Hodgkin's lymphoma is diffuse large B-cell lymphoma.

In another embodiment, the level of NF-κB activity is measured by an enzyme-linked immunosorbent assay.

In one embodiment, provided herein is a method for predicting tumor response to treatment in a non-Hodgkin's lymphoma patient, comprising:
(i) obtaining a biological sample from the patient;
(ii) culturing cells from the biological sample;
(iii) purifying RNA from the cultured cells; and
(iv) identifying increased expression of a gene associated with the activated B-cell phenotype of non-Hodgkin's lymphoma relative to control non-activated B-cell phenotype of non-Hodgkin's lymphoma;
wherein increased expression of a gene associated with the activated B-cell phenotype of non-Hodgkin's lymphoma indicates a likelihood of an effective patient tumor response to 3-(5-amino-2-methyl-4-oxo-4H-quinazolin-3-yl)-piperidine-2,6-dione treatment.

In one embodiment, increased expression is an increase of about 1.5×, 2.0×, 3×, 5×, or more.

In one embodiment, the gene associated with the activated B-cell phenotype is selected from the group consisting of IRF4/MUM1, FOXP1, SPIB, CARD11 and BLIMP/PDRM1.

In one embodiment, identifying the expression of a gene associated with the activated B-cell phenotype of non-Hodgkin's lymphoma is performed by quantitative real-time PCR.

Also provided herein is a method for treating or managing non-Hodgkin's lymphoma, comprising:
(i) identifying a patient having non-Hodgkin's lymphoma sensitive to treatment with 3-(5-amino-2-methyl-4-oxo-4H-quinazolin-3-yl)-piperidine-2,6-dione; and
(ii) administering to the patient a therapeutically effective amount of 3-(5-amino-2-methyl-4-oxo-4H-quinazolin-3-yl)-piperidine-2,6-dione, or a pharmaceutically acceptable salt, solvate or hydrate thereof.

In one embodiment, the non-Hodgkin's lymphoma is diffuse large B-cell lymphoma.

In another embodiment, the non-Hodgkin's lymphoma is of the activated B-cell phenotype.

In another embodiment, the diffuse large B-cell lymphoma is characterized by the expression of one or more biomarkers overexpressed in RIVA, U2932, TMD8, OCI-Ly3 or OCI-Ly10 cell lines.

In another embodiment, the diffuse large B-cell lymphoma is characterized by the expression of one or more biomarkers overexpressed in RIVA, U2932, TMD8 or OCI-Ly10 cell lines.

In one embodiment, identifying a patient having lymphoma sensitive to treatment with 3-(5-amino-2-methyl-4-oxo-4H-quinazolin-3-yl)-piperidine-2,6-dione comprises characterization of the lymphoma phenotype of the patient.

In one embodiment, the lymphoma phenotype is characterized as an activated B-cell subtype.

In one embodiment, the lymphoma phenotype is characterized as an activated B-cell subtype of diffuse large B-cell lymphoma.

In certain embodiments, identification of the lymphoma phenotype comprises obtaining a biological sample from a patient having lymphoma. In one embodiment, the biological sample is a cell culture or tissue sample. In one embodiment, the biological sample is a sample of tumor cells. In another embodiment, the biological sample is a lymph node biopsy, a bone marrow biopsy, or a sample of peripheral blood tumor cells. In one embodiment, the biological sample is a blood sample.

In one embodiment, identifying a patient having non-Hodgkin's lymphoma sensitive to treatment with 3-(5-amino-2-methyl-4-oxo-4H-quinazolin-3-yl)-piperidine-2,6-dione comprises identification of a gene associated with an activated B-cell phenotype. In one embodiment, the gene associated with the activated B-cell phenotype is selected from the group consisting of IRF4/MUM1, FOXP1, SPIB, CARD11 and BLIMP/PDRM1.

In one embodiment, identifying a patient having non-Hodgkin's lymphoma sensitive to treatment with 3-(5-amino-2-methyl-4-oxo-4H-quinazolin-3-yl)-piperidine-2,6-dione comprises measuring the level of NF-κB activity in the patient. In another embodiment, measuring the level of NF-κB activity in a patient comprises measuring the baseline NF-κB activity level in tumor cells obtained from the patient.

In another embodiment, the diffuse large B-cell lymphoma is characterized by one or more of the following:
(i) over expression of SPIB, a hematopoietic-specific Ets family transcription factor required for survival of activated B-cell subtype cells;
(ii) higher constitutive IRF4/MUM1 expression than GCB subtype cells;
(iii) higher constitutive FOXP1 expression up-regulated by trisomy 3;
(iv) higher constitutive Blimp1, i.e., PRDM1, expression; and
(v) higher constitutive CARD11 gene expression; and
(vi) an increased level of NF-κB activity relative to non-activated B-cell subtype DLBCL cells.

Additional prognostic factors that may be used concurrently with those provided herein are prognostic factors of disease (tumor) burden, absolute lymphocyte count (ALC), time since last rituximab therapy for lymphomas, or all of the above.

Also provided herein is a method of selecting a group of cancer patients based on the level of CRBN expression, or the levels of DDB1, DDB2, IRF4 or NFκB expression within the cancer, for the purposes of predicting clinical response, monitoring clinical response, or monitoring patient compliance to dosing by 3-(5-amino-2-methyl-4-oxo-4H-quinazolin-3-yl)-piperidine-2,6-dione, a stereoisomer thereof, or a pharmaceutically acceptable salt, solvate, hydrate, co-crystal, clathrate, or polymorph thereof; wherein the cancer patients are selected from multiple myeloma, non-Hodgkin's lymphoma, diffuse large B-cell lymphoma, melanoma and solid tumor patients. Baseline levels of expression of these genes can be predictive of the sensitivity of a cancer to treatment with 3-(5-amino-2-methyl-4-oxo-4H-quinazolin-3-yl)-piperidine-2,6-dione.

In one embodiment, IRF4/MUM1 expression in cancer cells, e.g., ABC-subtype lymphoma, can be decreased with the treatment of 3-(5-amino-2-methyl-4-oxo-4H-quinazolin-3-yl)-piperidine-2,6-dione. In some embodiments, IRF4 downregulation by 3-(5-amino-2-methyl-4-oxo-4H-quinazolin-3-yl)-piperidine-2,6-dione can be a potential pharmacodynamic biomarker.

In one embodiment, the cancer patients are multiple myeloma patients.

In one embodiment, the cancer patients are non-Hodgkin's lymphoma patients.

In one embodiment, the method of selecting a group of cancer patients is based on the level of DDB1 expression within the cancer.

In one embodiment, the method of selecting a group of cancer patients is based on the level of DDB2 expression within the cancer.

In one embodiment, the method of selecting a group of cancer patients is based on the level of IRF4 expression within the cancer.

In one embodiment, the method of selecting a group of cancer patients is based on the level of NFκB expression within the cancer.

In another embodiment, the method comprises selecting a group of cancer patients responsive to treatment with 3-(5-amino-2-methyl-4-oxo-4H-quinazolin-3-yl)-piperidine-2,6-dione, a stereoisomer thereof, or a pharmaceutically acceptable salt, solvate, hydrate, co-crystal, clathrate, or polymorph thereof based on the level of CRBN expression, or the levels of DDB1, DDB2, IRF4 or NFκB expression within the patient's T cells, B cells, or plasma cells, for the purposes of predicting clinical response, monitoring clinical response, or monitoring patient compliance to dosing by 3-(5-amino-2-methyl-4-oxo-4H-quinazolin-3-yl)-piperidine-2,6-dione, a stereoisomer thereof, or a pharmaceutically acceptable salt, solvate, hydrate, co-crystal, clathrate, or polymorph thereof. In one embodiment, the cancer patients are selected from multiple myeloma, non-Hodgkin's lymphoma, diffuse large B-cell lymphoma, melanoma and solid tumor patients.

Also provided herein are methods of treating cancer, e.g., lymphoma, non-Hodgkin's lymphoma, multiple myeloma, leukemia, acute myeloid leukemia (AML), and solid tumors, which result in an improvement in overall survival of the patient. In some embodiments, the improvement in overall survival of the patient is observed in a patient population sensitive to treatment with 3-(5-amino-2-methyl-4-oxo-4H-quinazolin-3-yl)-piperidine-2,6-dione. In some embodiments, the patient population sensitive to treatment with 3-(5-amino-2-methyl-4-oxo-4H-quinazolin-3-yl)-piperidine-2,6-dione is characterized by one or more biomarkers provided herein.

In other embodiments, provided herein are methods of treating cancer, e.g., lymphoma, non-Hodgkin's lymphoma, multiple myeloma, leukemia, acute myeloid leukemia (AML), and solid tumors, which result in disease free survival of the patient. In some embodiments, disease free survival of the patient is observed in a patient population sensitive to treatment with 3-(5-amino-2-methyl-4-oxo-4H-quinazolin-3-yl)-piperidine-2,6-dione. In some embodiments, the patient population sensitive to treatment with 3-(5-amino-2-methyl-4-oxo-4H-quinazolin-3-yl)-piperidine-2,6-dione is characterized by one or more biomarkers provided herein.

In other embodiments, provided herein are methods of treating cancer, e.g., lymphoma, non-Hodgkin's lymphoma, multiple myeloma, leukemia, acute myeloid leukemia (AML), and solid tumors, which result in an improvement in the objective response rate in the patient population. In some embodiments, the patient population sensitive to treatment with 3-(5-amino-2-methyl-4-oxo-4H-quinazolin-3-yl)-piperidine-2,6-dione. In some embodiments, the patient population sensitive to treatment with 3-(5-amino-2-methyl-4-oxo-4H-quinazolin-3-yl)-piperidine-2,6-dione is characterized by one or more biomarkers provided herein.

In other embodiments, provided herein are methods of treating cancer, e.g., lymphoma, non-lymphoma, Hodgkin's lymphoma, multiple myeloma, leukemia, acute myeloid leukemia (AML), and solid tumors, which result in an improved time to progression or progression-free survival of the patient. In some embodiments, the improved time to progression or progression-free survival of the patient is observed in a patient population sensitive to treatment with 3-(5-amino-2-methyl-4-oxo-4H-quinazolin-3-yl)-piperidine-2,6-dione. In some embodiments, the patient population sensitive to treatment with 3-(5-amino-2-methyl-4-oxo-4H-quinazolin-3-yl)-piperidine-2,6-dione is characterized by one or more biomarkers provided herein.

Also provided herein are kits useful for predicting the likelihood of an effective lymphoma, non-Hodgkin's lymphoma, multiple myeloma, leukemia, AML or solid tumor treatment or for monitoring the effectiveness of a treatment with 3-(5-amino-2-methyl-4-oxo-4H-quinazolin-3-yl)-piperidine-2,6-dione. The kit comprises a solid support, and a means for detecting the expression of a biomarker in a biological sample. Such a kit may employ, for example, a dipstick, a membrane, a chip, a disk, a test strip, a filter, a microsphere, a slide, a multiwell plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide. The biological sample can be, for example, a cell culture, a cell line, a tissue, an oral tissue, gastrointestinal tissue, an organ, an organelle, a biological fluid, a blood sample, a urine sample, or a skin sample. The biological sample can be, for example, a lymph node biopsy, a bone marrow biopsy, or a sample of peripheral blood tumor cells.

In one embodiment, the kit comprises a solid support, nucleic acids contacting the support, where the nucleic acids are complementary to at least 20, 50, 100, 200, 350, or more bases of mRNA of a gene associated with an activated B-cell phenotype in a NHL, and a means for detecting the expression of the mRNA in a biological sample. In one embodiment, the gene associated with the activated B-cell phenotype is selected from the group consisting of IRF4/MUM1, FOXP1, SPIB, CARD11 and BLIMP/PDRM1.

In one embodiment, a kit useful for predicting the likelihood of an effective lymphoma, non-Hodgkin's lymphoma, multiple myeloma, leukemia, AML or solid tumor treatment, or for monitoring the effectiveness of a treatment with 3-(5-amino-2-methyl-4-oxo-4H-quinazolin-3-yl)-piperidine-2,6-dione is provided. The kit comprises a solid support, and a means for detecting the expression of NF-κB in a biological sample. In one embodiment, the biological sample is a cell culture or tissue sample. In one embodiment, the biological sample is a sample of tumor cells. In another embodiment, the biological sample is a lymph node biopsy, a bone marrow biopsy, or a sample of peripheral blood tumor cells. In one embodiment, the biological sample is a blood sample. In one embodiment, the NHL is DLBCL.

In certain embodiments, the kits provided herein employ means for detecting the expression of a biomarker by quantitative real-time PCR (QT-PCR), microarray, flow cytometry or immunofluorescence. In other embodiments, the expression of the biomarker is measured by ELISA-based methodologies or other similar methods known in the art. Additional mRNA and protein expression techniques may be used in connection with the methods and kits provided herein, e.g., cDNA hybridization and cytometric bead array methods.

In embodiment, provided herein is a kit for predicting tumor response to treatment with 3-(5-amino-2-methyl-4-oxo-4H-quinazolin-3-yl)-piperidine-2,6-dione in a non-Hodgkin's lymphoma patient, comprising:
(i) a solid support; and
(ii) a means for detecting the expression of a biomarker of an activated B-cell phenotype of non-Hodgkin's lymphoma in a biological sample.

In one embodiment, the biomarker is NF-κB.

In one embodiment, the biomarker is a gene associated with the activated B-cell phenotype and is selected from the group consisting of IRF4/MUM1, FOXP1, SPIB, CARD11 and BLIMP/PDRM1.

In particular methods of the invention, a 3-(5-amino-2-methyl-4-oxo-4H-quinazolin-3-yl)-piperidine-2,6-dione is administered in combination with a therapy conventionally used to treat, prevent or manage cancer. Examples of such conventional therapies include, but are not limited to, surgery, chemotherapy, radiation therapy, hormonal therapy, biological therapy and immunotherapy.

Also provided herein are pharmaceutical compositions, single unit dosage forms, dosing regimens and kits which comprise 3-(5-amino-2-methyl-4-oxo-4H-quinazolin-3-yl)-piperidine-2,6-dione, or a pharmaceutically acceptable salt, solvate, hydrate, stereoisomer, clathrate, or prodrug thereof, and a second, or additional, active agent. Second active agents include specific combinations, or "cocktails," of drugs.

In some embodiments, the methods for treating, preventing and/or managing lymphomas provided herein may be used in patients that have not responded to standard treatment. In one embodiment, the lymphoma is relapsed, refractory or resistant to conventional therapy.

In other embodiments, the methods for treating, preventing and/or managing lymphomas provided herein may be used in treatment naive patients, i.e., patients that have not yet received treatment.

In certain embodiments, 3-(5-amino-2-methyl-4-oxo-4H-quinazolin-3-yl)-piperidine-2,6-dione, or an enantiomer or a mixture of enantiomers thereof, or a pharmaceutically acceptable salt, solvate, hydrate, co-crystal, clathrate, or polymorph thereof, is administered in combination or alternation with a therapeutically effective amount of one or more additional active agents. Second active agents include small molecules and large molecules (e.g., proteins and antibodies), examples of which are provided herein, as well as stem cells. Methods or therapies that can be used in combination with the administration of the compound provided herein include, but are not limited to, surgery, blood transfusions, immunotherapy, biological therapy, radiation therapy, and other non-drug based therapies presently used to treat, prevent or manage disease and conditions associated with or characterized by undesired angiogenesis.

In one embodiment, the additional active agent is selected from the group consisting of an alkylating agent, an adenosine analog, a glucocorticoid, a kinase inhibitor, a SYK inhibitor, a PDE3 inhibitor, a PDE7 inhibitor, doxorubicin, chlorambucil, vincristine, bendamustine, forskolin, rituximab, or a combination thereof.

In one embodiment, the additional active agent is rituximab.

In one embodiment, the glucocorticoid is hydrocortisone or dexamethasone.

In one embodiment, 3-(5-amino-2-methyl-4-oxo-4H-quinazolin-3-yl)-piperidine-2,6-dione is administered in an amount of about 5 to about 50 mg per day.

In one embodiment, 3-(5-amino-2-methyl-4-oxo-4H-quinazolin-3-yl)-piperidine-2,6-dione is administered in an amount of about 5 to about 25 mg per day.

In another embodiment, 3-(5-amino-2-methyl-4-oxo-4H-quinazolin-3-yl)-piperidine-2,6-dione is administered in an amount of about 5, 10, 15, 25, 30 or 50 mg per day.

In another embodiment, 10 or 25 mg of 3-(5-amino-2-methyl-4-oxo-4H-quinazolin-3-yl)-piperidine-2,6-dione is administered per day.

In one embodiment, 3-(5-amino-2-methyl-4-oxo-4H-quinazolin-3-yl)-piperidine-2,6-dione is administered twice per day.

Provided herein are pharmaceutical compositions (e.g., single unit dosage forms) that can be used in methods disclosed herein. In certain embodiments, the pharmaceutical compositions comprise 3-(5-amino-2-methyl-4-oxo-4H-quinazolin-3-yl)-piperidine-2,6-dione, or an enantiomer or a mixture of enantiomers thereof, or a pharmaceutically acceptable salt, solvate, hydrate, co-crystal, clathrate, or polymorph thereof, and a second active agent.

In one embodiment, 3-(5-amino-2-methyl-4-oxo-4H-quinazolin-3-yl)-piperidine-2,6-dione is orally administered.

In one embodiment, 3-(5-amino-2-methyl-4-oxo-4H-quinazolin-3-yl)-piperidine-2,6-dione is administered in a capsule or tablet.

In one embodiment, 3-(5-amino-2-methyl-4-oxo-4H-quinazolin-3-yl)-piperidine-2,6-dione is administered for 21 days followed by seven days rest in a 28 day cycle.

5.1 Definitions

To facilitate understanding of the disclosure set forth herein, a number of terms are defined below.

The term "subject" or "patient" refers to an animal, including, but not limited to, a mammal, including a primate (e.g., human), cow, sheep, goat, horse, dog, cat, rabbit, rat, or mouse. The terms "subject" and "patient" are used interchangeably herein in reference, for example, to a mammalian subject, such as a human subject.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a patient with such a disease or disorder. In some embodiments, the terms refer to the administration of a compound provided herein, with or without other additional active agent, after the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of diseases or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a patient derives from a prophylactic and/or therapeutic agent do not result in a cure of the disease or disorder. In this regard, the term "managing" encompasses treating a patient who had suffered from the particular disease in an attempt to prevent or minimize the recurrence of the disease, or lengthening the time during which the remains in remission.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy*, 21st Edition; Lippincott Williams & Wilkins: Philadelphia, Pa., 2005; *Handbook of Pharmaceutical Excipients*, 5th Edition; Rowe et al., Eds., The Pharmaceutical Press and the American Pharmaceutical Association: 2005; and *Handbook of Pharmaceutical Additives*, 3rd Edition; Ash and Ash Eds., Gower Publishing Company: 2007; *Pharmaceutical Preformulation and Formulation*, Gibson Ed., CRC Press LLC: Boca Raton, Fla., 2004).

"Tumor," as used herein, refers to all neoplastic cell growth and proliferation, whether malignant or benign, and all precancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

The term "relapsed" refers to a situation where a subject or a mammal, which has had a remission of cancer after therapy has a return of cancer cells.

As used herein, an "effective patient tumor response" refers to any increase in the therapeutic benefit to the patient. An "effective patient tumor response" can be, for example, a 5%, 10%, 25%, 50%, or 100% decrease in the rate of progress of the tumor. An "effective patient tumor response" can be, for example, a 5%, 10%, 25%, 50%, or 100% decrease in the physical symptoms of a cancer. An "effective patient tumor response" can also be, for example, a 5%, 10%, 25%, 50%, 100%, 200%, or more increase in the response of the patient, as measured by any suitable means, such as gene expression, cell counts, assay results, etc.

The term "likelihood" generally refers to an increase in the probability of an event. The term "likelihood" when used in reference to the effectiveness of a patient tumor response generally contemplates an increased probability that the rate of tumor progress or tumor cell growth will decrease. The term "likelihood" when used in reference to the effectiveness of a patient tumor response can also generally mean the increase of indicators, such as mRNA or protein expression, that may evidence an increase in the progress in treating the tumor.

The term "predict" generally means to determine or tell in advance. When used to "predict" the effectiveness of a cancer treatment, for example, the term "predict" can mean that the likelihood of the outcome of the cancer treatment can be determined at the outset, before the treatment has begun, or before the treatment period has progressed substantially.

The term "monitor," as used herein, generally refers to the overseeing, supervision, regulation, watching, tracking, or surveillance of an activity. For example, the term "monitoring the effectiveness of a compound" refers to tracking the effectiveness in treating a cancer in a patient or in a tumor cell culture. Similarly, the "monitoring," when used in connection with patient compliance, either individually, or in a clinical trial, refers to the tracking or confirming that the patient is actually taking the immunomodulatory compound being tested as prescribed. The monitoring can be performed, for example, by following the expression of mRNA or protein biomarkers.

An improvement in the cancer or cancer-related disease can be characterized as a complete or partial response. "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about a 10%, 20%, 30%, 40%, 50%, 60%, 70%, 80%, or 90% decrease in all measurable tumor burden (i.e., the number of malignant cells present in the subject, or the measured bulk of tumor masses or the quantity of abnormal monoclonal protein) in the absence of new lesions. The term "treatment" contemplates both a complete and a partial response.

The term "refractory or resistant" refers to a circumstance where a subject or a mammal, even after intensive treatment, has residual cancer cells in his body.

The term "drug resistance" refers to the condition when a disease does not respond to the treatment of a drug or drugs. Drug resistance can be either intrinsic, which means the disease has never been responsive to the drug or drugs, or it can be acquired, which means the disease ceases responding to a drug or drugs that the disease had previously responded to. In certain embodiments, drug resistance is intrinsic. In certain embodiments, the drug resistance is acquired.

The term "sensitivity" and "sensitive" when made in reference to treatment with compound is a relative term which refers to the degree of effectiveness of the compound in lessening or decreasing the progress of a tumor or the disease being treated. For example, the term "increased sensitivity" when used in reference to treatment of a cell or tumor in connection with a compound refers to an increase of, at least a 5%, or more, in the effectiveness of the tumor treatment.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from the RNA molecule to give a protein, a polypeptide or a portion thereof.

An mRNA that is "upregulated" is generally increased upon a given treatment or condition. An mRNA that is "downregulated" generally refers to a decrease in the level of expression of the mRNA in response to a given treatment or condition. In some situations, the mRNA level can remain unchanged upon a given treatment or condition.

An mRNA from a patient sample can be "upregulated" when treated with an immunomodulatory compound, as compared to a non-treated control. This upregulation can be, for example, an increase of about 5%, 10%, 20%, 30%, 40%, 50%, 60%, 70%, 90%, 100%, 200%, 300%, 500%, 1,000%, 5,000% or more of the comparative control mRNA level.

Alternatively, an mRNA can be "downregulated", or expressed at a lower level, in response to administration of certain immunomodulatory compounds or other agents. A downregulated mRNA can be, for example, present at a level of about 99%, 95%, 90%, 80%, 70%, 60%, 50%, 40%, 30%, 20%, 10%, 1% or less of the comparative control mRNA level.

Similarly, the level of a polypeptide or protein biomarker from a patient sample can be increased when treated with an immunomodulatory compound, as compared to a non-treated control. This increase can be about 5%, 10%, 20%, 30%, 40%, 50%, 60%, 70%, 90%, 100%, 200%, 300%, 500%, 1,000%, 5,000% or more of the comparative control protein level.

Alternatively, the level of a protein biomarker can be decreased in response to administration of certain immunomodulatory compounds or other agents. This decrease can be, for example, present at a level of about 99%, 95%, 90%, 80%, 70%, 60%, 50%, 40%, 30%, 20%, 10%, 1% or less of the comparative control protein level.

The terms "determining", "measuring", "evaluating", "assessing" and "assaying" as used herein generally refer to any form of measurement, and include determining if an element is present or not. These terms include both quantitative and/or qualitative determinations. Assessing may be relative or absolute. "Assessing the presence of" can include determining the amount of something present, as well as determining whether it is present or absent.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N dibenzylethylenediamine, chloroprocaine, choline, diethanolamine, ethylenediamine, meglumaine (N-methylglucamine), lysine, and procaine.

As used herein and unless otherwise indicated, the term "solvate" means a compound provided herein or a salt thereof, that further includes a stoichiometric or non-stoichiometric amount of solvent bound by non-covalent intermolecular forces. Where the solvent is water, the solvate is a hydrate.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of the compound of Formula I provided herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of the compound of Formula I provided herein that comprise —NO, —NO$_2$, —ONO, or —ONO$_2$ moieties. Prodrugs can be prepared using such methods as described in *Burger's Medicinal Chemistry and Drug Discovery*, 172-178, 949-982 (Manfred E. Wolff ed., 5th ed. 1995), and *Design of Prodrugs* (H. Bundgaard ed., Elsevier, N.Y. 1985).

As used herein and unless otherwise indicated, the terms "biohydrolyzable amide," "biohydrolyzable ester," "biohydrolyzable carbamate," "biohydrolyzable carbonate," "biohydrolyzable ureide," and "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyl-oxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, amino acids, hydroxyalkylamines, heterocyclic and heteroaromatic amines, and polyether amines.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. In certain embodiments, a stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. As used herein and unless otherwise indicated, the term "stereomerically enriched" means a composition that comprises greater than about 60% by weight of one stereoisomer of a compound, greater than about 70% by weight, or greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

5.2 Clinical Trials Endpoints for Cancer Approval

"Overall survival" is defined as the time from randomization until death from any cause, and is measured in the intent-to-treat population. Overall survival should be evaluated in randomized controlled studies. Demonstration of a statistically significant improvement in overall survival can be considered to be clinically significant if the toxicity profile is acceptable, and has often supported new drug approval.

Several endpoints are based on tumor assessments. These endpoints include disease free survival (DFS), objective response rate (ORR), time to progression (TTP), progression-free survival (PFS), and time-to-treatment failure (TTF). The collection and analysis of data on these time-dependent endpoints are based on indirect assessments, calculations, and estimates (e.g., tumor measurements).

Generally, "disease free survival" (DFS) is defined as the time from randomization until recurrence of tumor or death from any cause. Although overall survival is a conventional endpoint for most adjuvant settings, DFS can be an important endpoint in situations where survival may be prolonged, making a survival endpoint impractical. DFS can be a surrogate for clinical benefit or it can provide direct evidence of clinical benefit. This determination is based on the magnitude of the effect, its risk-benefit relationship, and the disease setting. The definition of DFS can be complicated, particularly when deaths are noted without prior tumor progression documentation. These events can be scored either as disease recurrences or as censored events. Although all methods for statistical analysis of deaths have some limitations, considering all deaths (deaths from all causes) as recurrences can minimize bias. DFS can be overestimated using this definition, especially in patients who die after a long period without observation. Bias can be introduced if the frequency of long-term follow-up visits is dissimilar between the study arms or if dropouts are not random because of toxicity.

"Objective response rate" (ORR) is defined as the proportion of patients with tumor size reduction of a predefined amount and for a minimum time period. Response duration usually is measured from the time of initial response until documented tumor progression. Generally, the FDA has defined ORR as the sum of partial responses plus complete responses. When defined in this manner, ORR is a direct measure of drug antitumor activity, which can be evaluated in a single-arm study. If available, standardized criteria should be used to ascertain response. A variety of response criteria have been considered appropriate (e.g., RECIST criteria) (Therasse et al., (2000) *J. Natl. Cancer Inst,* 92: 205-16). The significance of ORR is assessed by its magnitude and duration, and the percentage of complete responses (no detectable evidence of tumor).

"Time to progression" (TTP) and "progression-free survival" (PFS) have served as primary endpoints for drug approval. TTP is defined as the time from randomization until objective tumor progression; TTP does not include deaths. PFS is defined as the time from randomization until objective tumor progression or death. Compared with TTP, PFS is the preferred regulatory endpoint. PFS includes deaths and thus can be a better correlate to overall survival. PFS assumes patient deaths are randomly related to tumor progression. However, in situations where the majority of deaths are unrelated to cancer, TTP can be an acceptable endpoint.

As an endpoint to support drug approval, PFS can reflect tumor growth and be assessed before the determination of a survival benefit. Its determination is not confounded by subsequent therapy. For a given sample size, the magnitude of effect on PFS can be larger than the effect on overall survival. However, the formal validation of PFS as a surrogate for survival for the many different malignancies that exist can be difficult. Data are sometimes insufficient to allow a robust evaluation of the correlation between effects on survival and PFS. Cancer trials are often small, and proven survival benefits of existing drugs are generally modest. The role of PFS as an endpoint to support licensing approval varies in different cancer settings. Whether an improvement in PFS represents a direct clinical benefit or a surrogate for clinical benefit depends on the magnitude of the effect and the risk-benefit of the new treatment compared to available therapies.

"Time-to-treatment failure" (TTF) is defined as a composite endpoint measuring time from randomization to discontinuation of treatment for any reason, including disease progression, treatment toxicity, and death. TTF is not recommended as a regulatory endpoint for drug approval. TTF does not adequately distinguish efficacy from these additional variables. A regulatory endpoint should clearly distinguish the efficacy of the drug from toxicity, patient or physician withdrawal, or patient intolerance.

5.3 The Compound

The compound suitable for use in the methods provided herein is 3-(5-amino-2-methyl-4-oxo-4H-quinazolin-3-yl)-piperidine-2,6-dione, having the structure of Formula I:

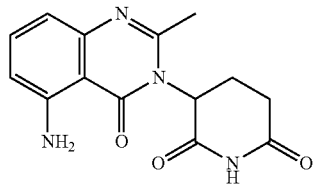

(I)

or an enantiomer or a mixture of enantiomers thereof; or a pharmaceutically acceptable salt, solvate, hydrate, co-crystal, clathrate, or polymorph thereof.

The compound of Formula I can be prepared according to the methods described in the Examples provided herein or as described in U.S. Pat. No. 7,635,700, the disclosure of which is incorporated herein by reference in its entirety. The compound can be also synthesized according to other methods apparent to those of skill in the art based upon the teaching herein.

The compound of Formula I markedly inhibits TNF-α, IL-1β, and other inflammatory cytokines in LPS-stimulated hPBMC and human whole blood. TNF-α is an inflammatory cytokine produced by macrophages and monocytes during acute inflammation. TNF-α is responsible for a diverse range of signaling events within cells. TNF-α may play a pathological role in cancer. Without being limited by theory, one of the biological effects exerted by the immunomodulatory compound of Formula I is the reduction of synthesis of TNF-α. The immunomodulatory compound of Formula I enhances the degradation of TNF-α mRNA. The compound of Formula I also potently inhibits IL-1β and stimulates IL-10 under these conditions.

Further, without being limited by theory, the compound of Formula I is a potent co-stimulator of T cells and increase cell proliferation in a dose dependent manner under appropriate conditions.

In certain embodiments, without being limited by theory, the biological effects exerted by the immunomodulatory compound of Formula I include, but not limited to, anti-angiogenic and immune modulating effects.

In certain embodiments, the compound of Formula I is a solid. In certain embodiments, the compound of Formula I is hydrated. In certain embodiments, the compound of Formula I is solvated. In certain embodiments, the compound of Formula I is anhydrous. In certain embodiments, the compound of Formula I is nonhygroscopic.

In certain embodiments, the solid compound of Formula I is amorphous. In certain embodiments, the solid compound of Formula I is crystalline. In certain embodiments, the solid compound of Formula I is in a crystalline form described in U.S. Provisional Pat. App. No. 61/451,806, filed Mar. 11, 2011, which is incorporated herein by reference in its entirety.

The solid forms of the compound of Formula I can be prepared according to the methods described in the disclosure of U.S. Provisional Pat. App. No. 61/451,806. The solid forms can be also prepared according to other methods apparent to those of skill in the art.

In certain embodiments, the compound of Formula I is a hydrochloride salt of 3-(5-amino-2-methyl-4-oxo-4H-quinazolin-3-yl)-piperidine-2,6-dione, or an enantiomer or a mixture of enantiomers thereof; or a pharmaceutically acceptable solvate, hydrate, co-crystal, clathrate, or polymorph thereof. In certain embodiments, the hydrochloride salt is a solid. In certain embodiments, the hydrochloride salt is anhydrous. In certain embodiments, the hydrochloride salt is nonhygroscopic. In certain embodiments, the hydrochloride salt is amorphous. In certain embodiments, the hydrochloride salt is crystalline. In certain embodiments, the hydrochloride salt is in crystalline Form A.

The hydrochloride salt of the compound of Formula I and solid forms thereof can be prepared according to the methods described in the disclosure of U.S. Provisional Pat. App. No. 61/451,806. The hydrochloride salt the solid forms thereof can be also prepared according to other methods apparent to those of skill in the art.

The compound of Formula I provided herein contains one chiral center, and can exist as a mixture of enantiomers, e.g., a racemic mixture. This disclosure encompasses the use of stereomerically pure forms of such a compound, as well as the use of mixtures of those forms. For example, mixtures comprising equal or unequal amounts of the enantiomers of the compound of Formula I provided herein may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of the structure.

5.4 Second Active Agents

A compound provided herein, e.g., the compound of Formula I, or an enantiomer or a mixture of enantiomers thereof, or a pharmaceutically acceptable salt, solvate, hydrate, co-crystal, clathrate, or polymorph thereof, can be combined with one or more other pharmacologically active compounds ("second active agents") in methods and compositions provided herein. It is believed that certain combinations work synergistically in the treatment of particular types of cancer, and certain diseases and conditions associated with or characterized by undesired angiogenesis. The compound of Formula I provided herein can also work to alleviate adverse effects associated with certain second active agents, and some second active agents can be used to alleviate adverse effects associated with the compound of Formula I provided herein.

One or more second active ingredients or agents can be used in the methods and compositions provided herein with the compound of Formula I provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. In certain embodiments, large molecule active agents are biological molecules, such as naturally occurring or artificially made proteins. Proteins that are particularly useful in this disclosure include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

Particular proteins that can be used in the methods and compositions of the disclosure include, but are not limited to: filgrastim, which is sold in the United States under the trade name NEUPOGEN® (Amgen, Thousand Oaks, Calif.); sargramostim, which is sold in the United States under the trade name LEUKINE® (Immunex, Seattle, Wash.); and recombinant EPO, which is sold in the United States under the trade name EPGEN® (Amgen, Thousand Oaks, Calif.).

Inhibitors of ActRII receptors or activin-ActRII inhibitors may be used in the methods and compositions provided herein. ActRII receptors include ActRIIA inhibitors and ActRIIB inhibitors. Inhibitors of ActRII receptors can be polypeptides comprising activin-binding domains of ActRII. In certain embodiments, the activin-binding domain comprising polypeptides are linked to an Fc portion of an antibody (i.e., a conjugate comprising an activin-binding domain comprising polypeptide of an ActRII receptor and an Fc portion of an antibody is generated). In certain embodiments, the activin-binding domain is linked to an Fc portion of an antibody via a linker, e.g., a peptide linker. Examples of such non-antibody proteins selected for activin or ActRIIA binding and methods for design and selection of the same are found in WO/2002/088171, WO/2006/055689, WO/2002/032925, WO/2005/037989, US 2003/0133939, and US 2005/0238646, each of which is incorporated herein by reference in its entirety.

Recombinant and mutated forms of GM-CSF can be prepared as described in U.S. Pat. Nos. 5,391,485; 5,393,870; and 5,229,496; the disclosure of each of which is incorporated herein by reference in its entirety. Recombinant and mutated forms of G-CSF can be prepared as described in U.S. Pat. Nos. 4,810,643; 4,999,291; 5,528,823; and 5,580,755; the disclosure of each of which is incorporated herein by reference in its entirety.

This disclosure encompasses the use of native, naturally occurring, and recombinant proteins. The disclosure further encompasses mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with the compound of Formula I provided herein include monoclonal and polyclonal antibodies. Examples of antibodies include, but are not limited to, trastuzumab (HERCEPTIN®), rituximab (RITUXAN®), bevacizumab (AVASTIN™), pertuzumab (OMNITARG™), tositumomab (BEXXAR®), edrecolomab (PANOREX®), panitumumab and G250. The compound of Formula I provided herein can also be combined with or used in combination with anti-TNF-α antibodies.

Large molecule active agents may be administered in the form of anti-cancer vaccines. For example, vaccines that secrete, or cause the secretion of, cytokines such as IL-2, SCF, CXCl4 (platelet factor 4), G-CSF, and GM-CSF can be used in the methods, pharmaceutical compositions, and kits of the disclosure. See, e.g., Emens, L. A., et al., *Curr. Opinion Mol. Ther.* 3(1):77-84 (2001).

Second active agents that are small molecules can also be used to alleviate adverse effects associated with the administration of the compound of Formula I provided herein. However, like some large molecules, many are believed to be capable of providing a synergistic effect when administered with (e.g., before, after or simultaneously) the compound of Formula I. Examples of small molecule second active agents include, but are not limited to, anti-cancer agents, antibiotics, immunosuppressive agents, and steroids.

Examples of anti-cancer agents include, but are not limited to: abraxane; ace-11; acivicin; aclarubicin; acodazole hydrochloride; acronine; adozelesin; aldesleukin; altretamine; ambomycin; ametantrone acetate; amrubicin; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; herceptin; hydroxyurea; idarubicin hydrochloride; ifosfamide; ilmofosine; iproplatin; irinotecan; irinotecan hydrochloride; lanreotide acetate; lapatinib; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; romidepsin; safingol; safingol hydrochloride; semustine; simtrazene; sparfosate sodium; sparsomycin; spirogermanium hydrochloride; spiromustine; spiroplatin; stem cell treatments such as PDA-001; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; b-FGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., GLEEVEC®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (GENASENSE®); O$^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, oblimersen (GENASENSE®), remicade, docetaxel, celecoxib, melphalan, dexamethasone (DECADRON®), steroids, gemcitabine, cisplatinum, temozolomide, etoposide, cyclophosphamide, temodar, carboplatin, procarbazine, gliadel, tamoxifen, topotecan, methotrexate, ARISA®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, paclitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (DOXIL®), paclitaxel, ganciclovir, adriamycin, estramustine sodium phosphate) (EMCYT®), sulindac, and etoposide.

5.5 Biomarkers

Provided herein are methods relating to the use of mRNAs or proteins as biomarkers to ascertain the effectiveness of cancer therapy. mRNA or protein levels can be used to determine whether a particular agent is likely to be successful in the treatment of a specific type of cancer, e.g., non-Hodgkin's lymphoma.

A biological marker or "biomarker" is a substance whose detection indicates a particular biological state, such as, for example, the presence of cancer. In some embodiments, biomarkers can either be determined individually, or several biomarkers can be measured simultaneously.

In some embodiments, a "biomarker" indicates a change in the level of mRNA expression that may correlate with the risk or progression of a disease, or with the susceptibility of the disease to a given treatment. In some embodiments, the biomarker is a nucleic acid, such as a mRNA or cDNA.

In additional embodiments, a "biomarker" indicates a change in the level of polypeptide or protein expression that may correlate with the risk, susceptibility to treatment, or progression of a disease. In some embodiments, the biomarker can be a polypeptide or protein, or a fragment thereof. The relative level of specific proteins can be determined by methods known in the art. For example, antibody based methods, such as an immunoblot, enzyme-linked immunosorbent assay (ELISA), or other methods can be used.

5.6 Methods of Treatment and Prevention

In one embodiment, provided herein is a method of treating and preventing cancer, which comprises administering to a patient a compound provided herein, e.g., the compound of Formula I, or an enantiomer or a mixture of enantiomers thereof, or a pharmaceutically acceptable salt, solvate, hydrate, co-crystal, clathrate, or polymorph thereof.

In another embodiment, provided herein is method of managing cancer, which comprises administering to a patient a compound provided herein, e.g., the compound of Formula I, or an enantiomer or a mixture of enantiomers thereof, or a pharmaceutically acceptable salt, solvate, hydrate, co-crystal, clathrate, or polymorph thereof. Provided herein are methods of treating or managing lymphoma, particularly non-Hodgkin's lymphoma. In some embodiments, provided herein are methods for the treatment or management of non-Hodgkin's lymphoma (NHL), including but not limited to, diffuse large B-cell lymphoma (DLBCL), using prognostic factors.

Also provided herein are methods of treating patients who have been previously treated for cancer but are non-responsive to standard therapies, as well as those who have not previously been treated. The invention also encompasses methods of treating patients regardless of patient's age, although some diseases or disorders are more common in certain age groups. The invention further encompasses methods of treating patients who have undergone surgery in an attempt to treat the disease or condition at issue, as well as those who have not. Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

As used herein, the term "cancer" includes, but is not limited to, solid tumors and blood born tumors. The term "cancer" refers to disease of skin tissues, organs, blood, and vessels, including, but not limited to, cancers of the bladder, bone, blood, brain, breast, cervix, chest, colon, endometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant giolma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma In certain embodiments, the cancer is a blood borne tumor. In certain embodiments, the blood borne tumor is metastatic. In certain embodiments, the blood borne tumor is drug resistant. In certain embodiments, the cancer is myeloma or lymphoma.

In certain embodiments, the cancer is a solid tumor. In certain embodiments, the solid tumor is metastatic. In certain embodiments, the solid tumor is drug-resistant. In certain embodiments, the solid tumor is hepatocellular carcinoma, prostate cancer, ovarian cancer, or glioblastoma.

In certain embodiments, a therapeutically or prophylactically effective amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg per day.

In certain embodiment, a therapeutically or prophylactically effective amount is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg every other day.

In certain embodiments, the therapeutically or prophylactically effective amount is about 1, about 2, about 5, about 10, about 15, about 20, about 25, about 30, about 40, about 45, about 50, about 60, about 70, about 80, about 90, about 100, or about 150 mg per day.

In one embodiment, the recommended daily dose range of the compound of Formula I for the conditions described herein lie within the range of from about 0.5 mg to about 50 mg per day, preferably given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.5, 1, 2, 3, 4, 5, 10, 15, 20, 25 or 50 mg per day. In another embodiment, the recommended starting dosage may be 0.5, 1, 2, 3, 4, or 5 mg per day. The dose may be escalated to 15, 20, 25, 30, 35, 40, 45 and 50 mg/day. In a specific embodiment, the compound can be administered in an amount of about 25 mg/day to patients with NHL (e.g., DLBCL). In a particular embodiment, the compound can be administered in an amount of about 10 mg/day to patients with NHL (e.g., DLBCL).

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, or from about 0.01 to about 1 mg/kg/day.

The administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both (see, www.fda.gov/cder/cancer/animalframe.htm). For example, a dose of 1 mg/kg/day for a 65 kg human is approximately equal to 38 mg/m$^2$/day.

In certain embodiments, the amount of the compound administered is sufficient to provide a plasma concentration of the compound at steady state, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In other embodiments, the amount of the compound administered is sufficient to provide a plasma concentration of the compound at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of a compound provided herein, e.g., the compound of Formula I, or an enantiomer or a mixture of enantiomers thereof, or a pharmaceutically acceptable salt, solvate, hydrate, co-crystal, clathrate, or polymorph thereof. Once steady state is reached, there are minor peaks and troughs on the time dependent curve of the plasma concentration of the compound.

In certain embodiments, the amount of the compound administered is sufficient to provide a maximum plasma concentration (peak concentration) of the compound, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In certain embodiments, the amount of the compound administered is sufficient to provide a minimum plasma concentration (trough concentration) of the compound, ranging from about 0.001 to about 500 µM, about 0.002 to about 200 µM, about 0.005 to about 100 µM, about 0.01 to about 50 µM, from about 1 to about 50 µM, about 0.01 to about 25 µM, from about 0.01 to about 20 µM, from about 0.02 to about 20 µM, from about 0.02 to about 20 µM, or from about 0.01 to about 20 µM.

In certain embodiments, the amount of the compound administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

In certain embodiments, the patient to be treated with one of the methods provided herein has not been treated with anticancer therapy prior to the administration of the compound of Formula I. In certain embodiments, the patient to be treated with one of the methods provided herein has been treated with anticancer therapy prior to the administration of the compound of Formula I. In certain embodiments, the patient to be treated with one of the methods provided herein has developed drug resistance to the anticancer therapy.

The methods provided herein encompass treating a patient regardless of patient's age, although some diseases or disorders are more common in certain age groups. Further provided herein is a method for treating a patient who has undergone surgery in an attempt to treat the disease or condition at issue, as well in one who has not. Because the subjects with cancer have heterogeneous clinical manifestations and varying clinical outcomes, the treatment given to a particular subject may vary, depending on his/her prognosis. The skilled clinician will be able to readily determine without undue experimentation, specific secondary agents, types of surgery, and types of non-drug based standard therapy that can be effectively used to treat an individual subject with cancer.

Depending on the disease to be treated and the subject's condition, the compound of Formula I, or an enantiomer or a mixture of enantiomers thereof; or a pharmaceutically acceptable salt, solvate, hydrate, co-crystal, clathrate, or polymorph thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. The compound of Formula I, or an enantiomer or a mixture of enantiomers thereof; or a pharmaceutically acceptable salt, solvate, hydrate, co-crystal, clathrate, or polymorph thereof, may be formulated, alone or together, in suitable dosage unit with pharmaceutically acceptable excipients, carriers, adjuvants and vehicles, appropriate for each route of administration.

In one embodiment, the compound of Formula I, or an enantiomer or a mixture of enantiomers thereof; or a pharmaceutically acceptable salt, solvate, hydrate, co-crystal, clathrate, or polymorph thereof, is administered orally. In another embodiment, the compound of Formula I, or an enantiomer or a mixture of enantiomers thereof; or a pharmaceutically acceptable salt, solvate, hydrate, co-crystal, clathrate, or polymorph thereof, is administered parenterally. In yet another embodiment, the compound of Formula I, or an enantiomer or a mixture of enantiomers thereof; or a pharmaceutically acceptable salt, solvate, hydrate, co-crystal, clathrate, or polymorph thereof, is administered intravenously.

The compound of Formula I, or an enantiomer or a mixture of enantiomers thereof; or a pharmaceutically acceptable salt, solvate, hydrate, co-crystal, clathrate, or polymorph thereof, can be delivered as a single dose such as, e.g., a single bolus injection, or oral tablets or pills; or over time, such as, e.g., continuous infusion over time or divided bolus doses over time. The compound can be administered repeatedly if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

The compound of Formula I, or an enantiomer or a mixture of enantiomers thereof; or a pharmaceutically acceptable salt, solvate, hydrate, co-crystal, clathrate, or polymorph thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as the compound of Formula I, is administered once or more than once each day, for example, for a period of time. The term "continuous" is intended to mean that a therapeutic compound, such as the compound of Formula I, is administered daily for an uninterrupted period of at least 10 days to 52 weeks. The term "intermittent" or "intermittently" as used herein is intended to mean stopping and starting at either regular or irregular intervals. For example, intermittent administration of the compound of Formula I is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as the compound of Formula I, is administered daily or continuously but with a rest period.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the compound of Formula I, or an enantiomer or a mixture of enantiomers thereof; or a pharmaceutically acceptable salt, solvate, hydrate, co-crystal, clathrate, or polymorph thereof, is administered once a day. In another embodiment, the compound of Formula I, or an enantiomer or a mixture of enantiomers thereof; or a pharmaceutically acceptable salt, solvate, hydrate, co-crystal, clathrate, or polymorph thereof, is administered twice a day. In yet another embodiment, the compound of Formula I, or an enantiomer or a mixture of enantiomers thereof; or a pharmaceutically acceptable salt, solvate, hydrate, co-crystal, clathrate, or polymorph thereof, is administered three times a day. In still another embodiment, the compound of Formula I, or an enantiomer or a mixture of enantiomers thereof; or a pharmaceutically acceptable salt, solvate, hydrate, co-crystal, clathrate, or polymorph thereof, is administered four times a day.

In certain embodiments, the compound of Formula I, or an enantiomer or a mixture of enantiomers thereof; or a pharmaceutically acceptable salt, solvate, hydrate, co-crystal, clathrate, or polymorph thereof, is administered once per day from one day to six months, from one week to three months, from one week to four weeks, from one week to three weeks, or from one week to two weeks. In certain embodiments, the compound of Formula I, or a pharmaceutically acceptable salt or solvate thereof, is administered once per day for one week, two weeks, three weeks, or four weeks. In one embodiment, the compound of Formula I, or an enantiomer or a mixture of enantiomers thereof; or a pharmaceutically acceptable salt, solvate, hydrate, co-crystal, clathrate, or polymorph thereof, is administered once per day for one week. In another embodiment, the compound of Formula I, or an enantiomer or a mixture of enantiomers thereof; or a pharmaceutically acceptable salt, solvate, hydrate, co-crystal, clathrate, or polymorph thereof, is administered once per day for two weeks. In yet another embodiment, the compound of Formula I, or an enantiomer or a mixture of enantiomers thereof; or a pharmaceutically acceptable salt, solvate, hydrate, co-crystal, clathrate, or polymorph thereof, is administered once per day for three weeks. In still another embodiment, the compound of Formula I, or an enantiomer or a mixture of enantiomers thereof; or a pharmaceutically acceptable salt, solvate, hydrate, co-crystal, clathrate, or polymorph thereof, is administered once per day for four weeks.

5.6.1 Combination Therapy with a Second Active Agent

The compound of Formula I, or an enantiomer or a mixture of enantiomers thereof; or a pharmaceutically acceptable salt, solvate, hydrate, co-crystal, clathrate, or polymorph thereof, can also be combined or used in combination with other therapeutic agents useful in the treatment and/or prevention of cancer described herein.

In one embodiment, provided herein is a method of treating, preventing, or managing cancer, comprising administering to a patient 3-(5-amino-2-methyl-4-oxo-4H-quinazolin-3-yl)-piperidine-2,6-dione, or an enantiomer or a mixture of enantiomers thereof; or a pharmaceutically acceptable salt, solvate, hydrate, co-crystal, clathrate, or polymorph thereof; in combination with one or more second active agents, and optionally in combination with radiation therapy, blood transfusions, or surgery. Examples of second active agents are disclosed herein (see, e.g., section 5.3).

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a compound provided herein, a compound provided herein, e.g., the compound of Formula I, or an enantiomer or a mixture of enantiomers thereof, or a pharmaceutically acceptable salt, solvate, hydrate, co-crystal, clathrate, or polymorph thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of the compound of Formula I and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of the compound of Formula I is independent of the route of administration of a second therapy. In one embodiment, the compound of Formula I is administered orally. In another embodiment, the compound of Formula I is administered intravenously. Thus, in accordance with these embodiments, the compound of Formula I is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, the compound of Formula I and a second therapy are administered by the same mode of administration, orally or by IV. In another embodiment, the compound of Formula I is administered by one mode of administration, e.g., by IV, whereas the second agent (an anticancer agent) is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount of the compound of Formula I provided herein and any optional additional active agents concurrently administered to the patient. In certain embodiments, the second active agent is oblimersen (GENASENSE®), GM-CSF, G-CSF, SCF, EPO, taxotere, irinotecan, dacarbazine, transretinoic acid, topotecan, pentoxifylline, ciprofloxacin, dexamethasone, vincristine, doxorubicin, COX-2 inhibitor, IL2, IL8, IL18, IFN, Ara-C, vinorelbine, or a combination thereof.

In certain embodiments, GM-CSF, G-CSF, SCF or EPO is administered subcutaneously during about five days in a four or six week cycle in an amount ranging from about 1 to about 750 mg/m$^2$/day, from about 25 to about 500 mg/m$^2$/day, from about 50 to about 250 mg/m$^2$/day, or from about 50 to about 200 mg/m$^2$/day. In certain embodiments, GM-CSF may be administered in an amount of from about 60 to about 500 mcg/m$^2$ intravenously over 2 hours or from about 5 to about 12 mcg/m$^2$/day subcutaneously. In certain embodiments, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In certain embodiments, EPO may be administered subcutaneously in an amount of 10,000 Unit 3 times per week.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with melphalan and dexamethasone to patients with amyloidosis. In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, and steroids can be administered to patients with amyloidosis.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with gemcitabine and cisplatinum to patients with locally advanced or metastatic transitional cell bladder cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with a second active ingredient as follows: temozolomide to pediatric patients with relapsed or progressive brain tumors or recurrent neuroblastoma; celecoxib, etoposide and cyclophosphamide for relapsed or progressive CNS cancer; temodar to patients with recurrent or progressive meningioma, malignant meningioma, hemangiopericytoma, multiple brain metastases, relapsed brain tumors, or newly diagnosed glioblastoma multiforms; irinotecan to patients with recurrent glioblastoma; carboplatin to pediatric patients with brain stem glioma; procarbazine to pediatric patients with progressive malignant gliomas; cyclophosphamide to patients with poor prognosis malignant brain tumors, newly diagnosed or recurrent glioblastoma multiforms; Gliadel® for high grade recurrent malignant gliomas; temozolomide and tamoxifen for anaplastic astrocytoma; or topotecan for gliomas, glioblastoma, anaplastic astrocytoma or anaplastic oligodendroglioma.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with methotrexate, cyclophosphamide, taxane, abraxane, lapatinib, herceptin, aromatase inhibitors, selective estrogen modulators, estrogen receptor antagonists, and/or PLX3397 (Plexxikon) to patients with metastatic breast cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with temozolomide to patients with neuroendocrine tumors.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with gemcitabine to patients with recurrent or metastatic head or neck cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with gemcitabine to patients with pancreatic cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with colon cancer in combination with ARISA®, avastatin, taxol, and/or taxotere.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with capecitabine and/or PLX4032 (Plexxikon) to patients with refractory colorectal cancer or patients who fail first line therapy or have poor performance in colon or rectal adenocarcinoma.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with fluorouracil, leucovorin, and irinotecan to patients with Dukes C & D colorectal cancer or to patients who have been previously treated for metastatic colorectal cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with refractory colorectal cancer in combination with capecitabine, xeloda, and/or CPT-11.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with capecitabine and irinotecan to patients with refractory colorectal cancer or to patients with unresectable or metastatic colorectal carcinoma.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered alone or in combination with interferon alpha or capecitabine to patients with unresectable or metastatic hepatocellular carcinoma; or with cisplatin and thiotepa to patients with primary or metastatic liver cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with pegylated interferon alpha to patients with Kaposi's sarcoma.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with fludarabine, carboplatin, and/or topotecan to patients with refractory or relapsed or high-risk acuted myelogenous leukemia.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with liposomal daunorubicin, topotecan and/or cytarabine to patients with unfavorable karotype acute myeloblastic leukemia.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with gemcitabine, abraxane, erlotinib, geftinib, and/or irinotecan to patients with non-small cell lung cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with carboplatin and irinotecan to patients with non-small cell lung cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with doxetaxol to patients with non-small cell lung cancer who have been previously treated with carbo/VP 16 and radiotherapy.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with carboplatin and/or taxotere, or in combination with carboplatin, paclitaxel and/or thoracic radiotherapy to patients with non-small cell lung cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with taxotere to patients with stage IIIB or IV non-small cell lung cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with oblimersen (Genasense®) to patients with small cell lung cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with ABT-737 (Abbott Laboratories) and/or obatoclax (GX15-070) to patients with lymphoma and other blood cancers.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered alone or in combination with a second active ingredient such as vinblastine or fludarabine to patients with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with taxotere, IL-2, IFN, GM-CSF, PLX4032 (Plexxikon) and/or dacarbazine to patients with various types or stages of melanoma.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered alone or in combination with vinorelbine to patients with malignant mesothelioma, or stage IIIB non-small cell lung cancer with pleural implants or malignant pleural effusion mesothelioma syndrome.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with various types or stages of multiple myeloma in combination with dexamethasone, zoledronic acid, palmitronate, GM-CSF, biaxin, vinblastine, melphalan, busulphan, cyclophosphamide, IFN, palmidronate, prednisone, bisphosphonate, celecoxib, arsenic trioxide, PEG INTRON-A, vincristine, or a combination thereof.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with relapsed or refractory multiple myeloma in combination with doxorubicin (Doxil®), vincristine and/or dexamethasone (Decadron®).

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with various types or stages of ovarian cancer such as peritoneal carcinoma, papillary serous carcinoma, refractory ovarian cancer or recurrent ovarian cancer, in combination with taxol, carboplatin, doxorubicin, gemcitabine, cisplatin, xeloda, paclitaxel, dexamethasone, or a combination thereof.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with various types or stages of prostate cancer, in combination with xeloda, 5 FU/LV, gemcitabine, irinotecan plus gemcitabine, cyclophosphamide, vincristine, dexamethasone, GM-CSF, celecoxib, taxotere, ganciclovir, paclitaxel, adriamycin, docetaxel, estramustine, Emcyt, denderon or a combination thereof.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with various types or stages of renal cell cancer, in combination with capecitabine, IFN, tamoxifen, IL-2, GM-CSF, Celebrex®, or a combination thereof.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with various types or stages of gynecologic, uterus or soft tissue sarcoma cancer in combination with IFN, a COX-2 inhibitor such as Celebrex®, and/or sulindac.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with various types or stages of solid tumors in combination with celebrex, etoposide, cyclophosphamide, docetaxel, apecitabine, IFN, tamoxifen, IL-2, GM-CSF, or a combination thereof.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with scleroderma or cutaneous vasculitis in combination with celebrex, etoposide, cyclophosphamide, docetaxel, apecitabine, IFN, tamoxifen, IL-2, GM-CSF, or a combination thereof.

Also encompassed herein is a method of increasing the dosage of an anti-cancer drug or agent that can be safely and effectively administered to a patient, which comprises administering to the patient (e.g., a human) or an enantiomer or a mixture of enantiomers thereof, or a pharmaceutically acceptable salt, solvate, hydrate, co-crystal, clathrate, or polymorph thereof. Patients that can benefit by this method are those likely to suffer from an adverse effect associated with anti-cancer drugs for treating a specific cancer of the skin, subcutaneous tissue, lymph nodes, brain, lung, liver, bone, intestine, colon, heart, pancreas, adrenal, kidney, prostate, breast, colorectal, or combinations thereof. The administration of a compound provided herein, e.g., the compound of Formula I, or an enantiomer or a mixture of enantiomers thereof, or a pharmaceutically acceptable salt, solvate, hydrate, co-crystal, clathrate, or polymorph thereof, alleviates or reduces adverse effects which are of such severity that it would otherwise limit the amount of anti-cancer drug.

In one embodiment, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered orally and daily in an amount ranging from about 0.1 to about 150 mg, from about 1 to about 50 mg, or from about 2 to about 25 mg, prior to, during, or after the occurrence of the adverse effect associated with the administration of an anti-cancer drug to a patient. In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with specific agents such as heparin, aspirin, coumadin, or G-CSF to avoid adverse effects that are associated with anti-cancer drugs such as but not limited to neutropenia or thrombocytopenia.

In one embodiment, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with diseases and disorders associated with or characterized by, undesired angiogenesis in combination with additional active ingredients, including, but not limited to, anti-cancer drugs, anti-inflammatories, antihistamines, antibiotics, and steroids.

In another embodiment, encompassed herein is a method of treating, preventing and/or managing cancer, which comprises administering the compound of Formula I, or an enantiomer or a mixture of enantiomers thereof, or a pharmaceutically acceptable salt, solvate, hydrate, co-crystal, clathrate, or polymorph thereof, in conjunction with (e.g. before, during, or after) conventional therapy including, but not limited to, surgery, immunotherapy, biological therapy, radiation therapy, or other non-drug based therapy presently used to treat, prevent or manage cancer. The combined use of the compound provided herein and conventional therapy may provide a unique treatment regimen that is unexpectedly effective in certain patients. Without being limited by theory, it is believed that the compound of Formula I may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, hormonal therapy, biological therapy and immunotherapy. A compound provided herein, e.g., the compound of Formula I, or an enantiomer or a mixture of enantiomers thereof, or a pharmaceutically acceptable salt, solvate, hydrate, co-crystal, clathrate, or polymorph thereof, and other active ingredient can be administered to a patient prior to, during, or after the occurrence of the adverse effect associated with conventional therapy.

In one embodiment, the compound of Formula I can be administered in an amount ranging from about 0.1 to about 150 mg, from about 1 to about 25 mg, or from about 2 to about 10 mg orally and daily alone, or in combination with a second active agent disclosed herein (see, e.g., section 4.3), prior to, during, or after the use of conventional therapy.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, and doxetaxol are administered to patients with non-small cell lung cancer who were previously treated with carbo/VP 16 and radiotherapy.

5.6.2 Use with Transplantation Therapy

The compound of Formula I provided herein can be used to reduce the risk of Graft Versus Host Disease (GVHD). Therefore, encompassed herein is a method of treating, preventing and/or managing cancer, which comprises administering the compound of Formula I, or an enantiomer or a mixture of enantiomers thereof, or a pharmaceutically acceptable salt, solvate, hydrate, co-crystal, clathrate, or polymorph thereof, in conjunction with transplantation therapy.

As those of ordinary skill in the art are aware, the treatment of cancer is often based on the stages and mechanism of the disease. For example, as inevitable leukemic transformation develops in certain stages of cancer, transplantation of peripheral blood stem cells, hematopoietic stem cell preparation or bone marrow may be necessary. The combined use of the compound of Formula I provided herein and transplantation therapy provides a unique and unexpected synergism. In particular, the compound of Formula I exhibits immunomodulatory activity that may provide additive or synergistic effects when given concurrently with transplantation therapy in patients with cancer.

The compound of Formula I can work in combination with transplantation therapy reducing complications associated with the invasive procedure of transplantation and risk of GVHD. Encompassed herein is a method of treating, preventing and/or managing cancer which comprises administering to a patient (e.g., a human) the compound of Formula I, or an enantiomer or a mixture of enantiomers thereof, or a pharmaceutically acceptable salt, solvate, hydrate, co-crystal, clathrate, or polymorph thereof, before, during, or after the transplantation of umbilical cord blood, placental blood, peripheral blood stem cell, hematopoietic stem cell preparation, or bone marrow. Some examples of stem cells suitable for use in the methods provided herein are disclosed in U.S. Pat. No. 7,498,171, the disclosure of which is incorporated herein by reference in its entirety.

In one embodiment, the compound of Formula I is administered to patients with multiple myeloma before, during, or after the transplantation of autologous peripheral blood progenitor cell.

In another embodiment, the compound of Formula I is administered to patients with relapsing multiple myeloma after the stem cell transplantation.

In yet another embodiment, the compound of Formula I and prednisone are administered as maintenance therapy to patients with multiple myeloma following the transplantation of autologous stem cell.

In yet another embodiment, the compound of Formula I and dexamethasone are administered as salvage therapy for low risk post transplantation to patients with multiple myeloma.

In yet another embodiment, the compound of Formula I and dexamethasone are administered as maintenance therapy to patients with multiple myeloma following the transplantation of autologous bone marrow.

In yet another embodiment, the compound of Formula I is administered following the administration of high dose of melphalan and the transplantation of autologous stem cell to patients with chemotherapy responsive multiple myeloma.

In yet another embodiment, the compound of Formula I and PEG INTRO-A are administered as maintenance therapy to patients with multiple myeloma following the transplantation of autologous CD34-selected peripheral stem cell.

In yet another embodiment, the compound of Formula I is administered with post transplant consolidation chemotherapy to patients with newly diagnosed multiple myeloma to evaluate anti-angiogenesis.

In still another embodiment, the compound of Formula I and dexamethasone are administered as maintenance therapy after DCEP consolidation, following the treatment with high dose of melphalan and the transplantation of peripheral blood stem cell to 65 years of age or older patients with multiple myeloma.

In one embodiment, the compound of Formula I is administered to patients with NHL (e.g., DLBCL) before, during, or after the transplantation of autologous peripheral blood progenitor cell.

In another embodiment, the compound of Formula I is administered to patients with NHL (e.g., DLBCL) after a stem cell transplantation.

5.6.3 Cycling Therapy

In certain embodiments, the prophylactic or therapeutic agents provided herein are cyclically administered to a patient. Cycling therapy involves the administration of an active agent for a period of time, followed by a rest for a period of time, and repeating this sequential administration. Cycling therapy can reduce the development of resistance to one or more of the therapies, avoid, or reduce the side effects of one of the therapies, and/or improves the efficacy of the treatment.

Consequently, in certain embodiments, the compound of Formula I provided herein is administered daily in a single or divided doses in a four to six week cycle with a rest period of about a week or two weeks. The cycling method further allows the frequency, number, and length of dosing cycles to be increased. Thus, encompassed herein in certain embodiments is the administration of a compound provided herein, e.g., the compound of Formula I, or an enantiomer or a mixture of enantiomers thereof, or a pharmaceutically acceptable salt, solvate, hydrate, co-crystal, clathrate, or polymorph thereof, for more cycles than are typical when it is administered alone. In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered for a greater number of cycles that would typically cause dose-limiting toxicity in a patient to whom a second active ingredient is not also being administered.

In one embodiment, the compound of Formula I is administered daily and continuously for three or four weeks at a dose of from about 0.1 to about 150 mg/d followed by a break of one or two weeks.

In another embodiment, the compound of Formula I and a second active ingredient are administered orally, with administration of the compound of Formula I occurring 30 to 60 minutes prior to a second active ingredient, during a cycle of four to six weeks. In certain embodiments, the combination of the compound of Formula I and a second active ingredient is administered by intravenous infusion over about 90 minutes every cycle. In certain embodiments, one cycle comprises the administration from about 0.1 to about 150 mg/day of the compound of Formula I and from about 50 to about 200 mg/m$^2$/day of a second active ingredient daily for three to four weeks and then one or two weeks of rest. In certain embodiments, the number of cycles during which the combinatorial treatment is administered to a patient is ranging from about one to about 24 cycles, from about two to about 16 cycles, or from about four to about three cycles.

5.7 Pharmaceutical Compositions and Dosage Forms

In one embodiment, provided herein are pharmaceutical compositions and dosage forms, which comprise the compound of Formula I, or an enantiomer or a mixture of enantiomers thereof, or a pharmaceutically acceptable salt, solvate, hydrate, co-crystal, clathrate, or polymorph thereof. In another embodiment, pharmaceutical compositions and dosage forms further comprise one or more excipients.

In certain embodiments, pharmaceutical compositions and dosage forms provided herein also comprise one or more additional active ingredients. Consequently, pharmaceutical compositions and dosage forms provided herein comprise the compound of Formula I, or an enantiomer or a mixture of enantiomers thereof, or a pharmaceutically acceptable salt, solvate, hydrate, co-crystal, clathrate, or polymorph thereof, and a second active agent. Examples of optional second, or additional, active ingredients are disclosed herein (see, e.g., section 4.3).

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal, or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms provided herein may vary depending on their use. For example, a dosage form used in the acute treatment of a disease may contain larger amounts of one or more of the active ingredients than a dosage form used in the chronic treatment of the same disease. Similarly, a parenteral dosage form may contain smaller amounts of one or more of the active ingredients than an oral dosage form used to treat the same disease. See, e.g., *Remington's Pharmaceutical Sciences*, 18th ed., Mack Publishing, Easton Pa. (1990).

Whether a particular excipient is suitable for incorporation into a pharmaceutical composition or dosage form provided herein depends on a variety of factors, including, but not limited to, the route of administration. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, encompassed herein are pharmaceutical compositions and dosage forms that contain little, if any, lactose. As used herein, the term "lactose-free" means that the amount of lactose present, if any, is insufficient to substantially increase the degradation rate of an active ingredient.

Lactose-free compositions provided herein can comprise excipients that are listed, for example, in the *U.S. Pharmacopeia* (USP) 25-NF20 (2002). In certain embodiments, lactose-free compositions comprise active ingredients, a binder/filler, and a lubricant in pharmaceutically compatible and pharmaceutically acceptable amounts. In certain embodiments, lactose-free dosage forms comprise active ingredients, microcrystalline cellulose, pre-gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, in certain embodiments, provided herein are anhydrous compositions packaged using materials to prevent exposure to water such that they can be included in suitable formulary kits. Examples of suitable packaging include, but are not limited to, hermetically sealed foils, plastics, unit dose containers (e.g., vials), blister packs, and strip packs.

Encompassed herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In certain embodiments, the dosage forms provided herein comprise the compound of Formula I, or an enantiomer or a mixture of enantiomers thereof, or a pharmaceutically acceptable salt, solvate, hydrate, co-crystal, clathrate, or polymorph thereof, in an amount ranging from about 0.10 to about 1000 mg, from about 0.10 to about 500 mg, from about 0.10 to about 200 mg, from about 0.10 to about 150 mg, from about 0.10 to about 100 mg, or from about 0.10 to about 50 mg. In certain embodiments, the dosage forms provided herein comprise the compound of Formula I, or an enantiomer or a mixture of enantiomers thereof, or a pharmaceutically acceptable salt, solvate, hydrate, co-crystal, clathrate, or polymorph thereof, in an amount of about 0.1, about 1, about 2, about 5, about 7.5, about 10, about 12.5, about 15, about 17.5, about 20, about 25, about 50, about 100, about 150, or about 200 mg.

5.7.1 Oral Dosage Forms

In certain embodiments, pharmaceutical compositions provided herein that are suitable for oral administration are formulated as discrete dosage forms, examples of which include, but are not limited to, tablets (e.g., chewable tablets), caplets, capsules, and liquids (e.g., flavored syrups). Such dosage forms contain predetermined amounts of active ingredients and may be prepared by some known methods of pharmacy. See generally, *Remington's Pharmaceutical Sciences,* 18th ed., Mack Publishing, Easton Pa. (1990).

In certain embodiments, the oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms may be prepared by some known methods of pharmacy. In certain embodiments, pharmaceutical compositions and dosage forms are prepared by uniformly and intimately admixing the active ingredients with liquid carriers, finely divided solid carriers, or both, and then shaping the product into the desired presentation if necessary.

In certain embodiments, a tablet is prepared by compression or molding. In certain embodiments, compressed tablets are be prepared by compressing in a suitable machine the active ingredients in a free-flowing form, e.g., powder or granules, optionally mixed with an excipient. In certain embodiments, molded tablets are made by molding in a suitable machine a mixture of a powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms provided herein include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, AVICEL-PH-101, AVICEL-PH-103 AVICEL RC-581, AVICEL-PH-105 (FMC Corporation, American Viscose Division, Avicel Sales, Marcus Hook, Pa.), and mixtures thereof. An specific binder is a mixture of microcrystalline cellulose and sodium carboxymethyl cellulose (e.g., AVICEL RC-581). Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. In certain embodiments, the binder or filler in pharmaceutical compositions provided herein is present in from about 50 to about 99 weight percent of the pharmaceutical composition or dosage form.

Disintegrants are used in the compositions provided herein to provide tablets the ability to disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation. In certain embodiments, the pharmaceutical compositions provided herein comprise from about 0.5 to about 15 weight percent or from about 1 to about 5 weight percent of disintegrant.

Disintegrants that are suitable for use in pharmaceutical compositions and dosage forms provided herein include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that are suitable for use in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, but are not limited to, a syloid silica gel (AEROSIL200, W.R. Grace Co., Baltimore, Md.), a coagulated aerosol of synthetic silica (Degussa Co. of Plano, Tex.), CAB-O-SIL (a pyrogenic silicon dioxide, Cabot Co. of Boston, Mass.), and mixtures thereof. In certain embodiments, if used at all, lubricants are used in an amount of less than about 1 weight percent of the pharmaceutical compositions or dosage forms into which they are incorporated.

In certain embodiments, provided herein is a solid oral dosage form, comprising the compound of Formula I, or an enantiomer or a mixture of enantiomers thereof, or a pharmaceutically acceptable salt, solvate, hydrate, co-crystal, clathrate, or polymorph thereof; and one or more excipients selected from anhydrous lactose, microcrystalline cellulose, polyvinylpyrrolidone, stearic acid, colloidal anhydrous silica, and gelatin.

In certain embodiments, provided herein is a solid oral dosage form, comprising the compound of Formula I, or an enantiomer or a mixture of enantiomers thereof, or a pharmaceutically acceptable salt, solvate, hydrate, co-crystal, clathrate, or polymorph thereof; and anhydrous lactose, microcrystalline cellulose, polyvinylpyrrolidone, stearic acid, colloidal anhydrous silica, and gelatin.

In certain embodiments, provided herein is a solid oral dosage form, comprising a hydrochloride sale of the compound of Formula I, or an enantiomer or a mixture of enantiomers thereof, or a pharmaceutically solvate, hydrate, co-crystal, clathrate, or polymorph thereof; and one or more excipients selected from anhydrous lactose, microcrystalline cellulose, polyvinylpyrrolidone, stearic acid, colloidal anhydrous silica, and gelatin.

In certain embodiments, provided herein is a solid oral dosage form, comprising a hydrochloride sale of the compound of Formula I, or an enantiomer or a mixture of enantiomers thereof, or a pharmaceutically solvate, hydrate, co-crystal, clathrate, or polymorph thereof; and anhydrous lactose, microcrystalline cellulose, polyvinylpyrrolidone, stearic acid, colloidal anhydrous silica, and gelatin.

5.7.2 Delayed Release Dosage Forms

In certain embodiments, the active ingredients provided herein are administered by controlled release means or by delivery devices. Examples include, but are not limited to, those described in U.S. Pat. Nos. 3,845,770; 3,916,899; 3,536,809; 3,598,123; 4,008,719, 5,674,533, 5,059,595, 5,591,767, 5,120,548, 5,073,543, 5,639,476, 5,354,556, and 5,733,566, each of which is incorporated herein by reference in its entirety. In certain embodiments, such dosage forms are be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Encompassed herein are single unit dosage forms suitable for oral administration, including, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

5.7.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Some suitable vehicles that can be used to provide parenteral dosage forms provided herein include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms provided herein. For example, cyclodextrin and its derivatives can be used to increase the solubility of a compound provided herein, e.g., the compound of Formula I, or an enantiomer or a mixture of enantiomers thereof, or a pharmaceutically acceptable salt, solvate, hydrate, co-crystal, clathrate, or polymorph thereof. See, e.g., U.S. Pat. No. 5,134,127, the disclosure of which is incorporated herein by reference in its entirety.

5.7.4 Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences*, 16$^{th}$ and 18$^{th}$ eds., Mack Publishing, Easton Pa. (1980 & 1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein depend on the particular tissue to which a given pharmaceutical composition or dosage form will be applied. With that fact in mind, in certain embodiments, the excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Additional examples of such ingredients can be found, e.g., in *Remington's Pharmaceutical Sciences*, 16$^{th}$ and 18$^{th}$ eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

5.7.5 Kits

In certain embodiments, active ingredients provided herein are not administered to a patient at the same time or by the same route of administration. Therefore, encompassed herein are kits which, when used by the medical practitioner, can simplify the administration of appropriate amounts of active ingredients to a patient.

In certain embodiments, a kit provided herein comprises a dosage form of a compound provided herein, e.g., the compound of Formula I, or an enantiomer or a mixture of enantiomers thereof, or a pharmaceutically acceptable salt, solvate, hydrate, co-crystal, clathrate, or polymorph thereof. In certain embodiments, the kit provided herein further comprises additional active ingredients, such as oblimersen (GENASESE®), melphalan, G-CSF, GM-CSF, EPO, topotecan, dacarbazine, irinotecan, taxotere, IFN, COX-2 inhibitor, pentoxifylline, ciprofloxacin, dexamethasone, IL2, IL8, IL18, Ara-C, vinorelbine, isotretinoin, 13 cis-retinoic acid, or a pharmacologically active mutant or derivative thereof, or a combination thereof. Examples of the additional active ingredients include, but are not limited to, those disclosed herein (see, e.g., section 4.3).

In certain embodiments, the kit provided herein further comprises a device that is used to administer the active ingredients. Examples of such devices include, but are not limited to, syringes, drip bags, patches, and inhalers.

In certain embodiments, the kit provided herein further comprises cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

6. EXAMPLES

Certain embodiments of the invention are illustrated by the following non-limiting examples.

6.1 Preparation of 3-(5-Amino-2-methyl-4-oxo-4H-quinazolin-3-yl)-piperidine-2,6-dione

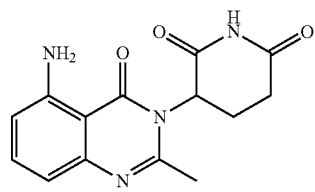 [SMILES: Cc1nc2cccc(N)c2c(=O)n1C1CCC(=O)NC1=O]

Step 1: To a solution of potassium hydroxide (16.1 g, 286 mmol) in water (500 mL), was added 3-nitrophthalimide (25.0 g, 130 mmol) in portion at 0° C. The suspension was stirred at 0° C. for 3 hrs, and then heated to 30° C. for 3 hrs. To the solution, was added HCl (100 mL, 6N). The resulting suspension was cooled to 0° C. for 1 hr. The suspension was filtered and washed with cold water (2×10 mL) to give 3-nitro-phthalamic acid as a white solid (24.6 g, 90% yield): $^1$H NMR (DMSO-$d_6$) δ 7.69 (brs, 1H, NHH), 7.74 (t, J=8 Hz, 1H, Ar), 7.92 (dd, J=1, 8 Hz, 1H, Ar), 8.13 (dd, J=1, 8 Hz, 1H, Ar), 8.15 (brs, 1H, NHH), 13.59 (s, 1H, OH); $^{13}$C NMR (DMSO-$d_6$) δ 125.33, 129.15, 130.25, 132.54, 136.72, 147.03, 165.90, 167.31.

Step 2: To a mixture of 3-nitro-phthalamic acid (24.6 g, 117 mmol) and potassium hydroxide (6.56 g, 117 mmol) in water (118 mL), was added a mixture of bromine (6 mL), potassium hydroxide (13.2 g, 234 mmol) in water (240 mL) at 0° C., followed by addition of a solution of potassium hydroxide (19.8 g, 351 mmol) in water (350 mL). After 5 minutes at 0° C., the mixture was heated in a 100° C. oil bath for 1 hr. The reaction solution was cooled to room temperature, and then, in an ice-water bath for 30 minutes. To the mixture, a solution of HCl (240 mL, 2N) was added dropwise at 0° C., and the resulting mixture was kept for 1 hr. The suspension was filtered and washed with water (5 mL) to give 2-amino-6-nitro-benzoic acid as yellow solid (15.6 g, 73% yield): HPLC: Waters Symmetry $C_{18}$, 5 μm, 3.9×150 mm, 1 mL/min, 240 nm, $CH_3CN/0.1\%$ $H_3PO_4$, 5% grad to 95% over 5 min, 5.83 min (85%); $^1$H NMR (DMSO-$d_6$) δ 6.90 (dd, J=1, 8 Hz, 1H, Ar), 7.01 (dd, J=1, 9 Hz, 1H, Ar), 7.31 (t, J=8 Hz, 1H, Ar), 8.5-9.5 (brs, 3H, OH, $NH_2$); $^{13}$C NMR (DMSO-$d_6$) δ 105.58, 110.14, 120.07, 131.74, 149.80, 151.36, 166.30; LCMS: MH=183.

Step 3: A mixture of 2-amino-6-nitro-benzoic acid (1.5 g, 8.2 mmol) in acetic anhydride (15 mL) was heated at 200° C. for 30 minutes in a microwave oven. The mixture was filtered and washed with ethyl acetate (20 mL). The filtrate was concentrated in vacuo. The solid was stirred in ether (20 mL) for 2 hrs. The suspension was filtered and washed with ether (20 mL) to give 2-methyl-5-nitro-benzo[d][1,3]oxazin-4-one as a light brown solid (1.4 g, 85% yield): HPLC: Waters Symmetry $C_{18}$, 5 μm, 3.9×150 mm, 1 mL/min, 240 nm, $CH_3CN/0.1\%$ $H_3PO_4$, 5% grad 95% in 5 min, 5.36 min (92%); $^1$H NMR (DMSO-$d_6$) δ 2.42 (s, 3H, $CH_3$), 7.79 (dd, J=1, 8 Hz, 1H, Ar), 7.93 (dd, J=1, 8 Hz, 1H, Ar), 8.06 (t, J=8 Hz, 1H, Ar); $^{13}$C NMR (DMSO-$d_6$) δ 20.87, 107.79, 121.54, 128.87, 137.19, 147.12, 148.46, 155.18, 161.78; LCMS: MH=207.

Step 4: Two vials each with a suspension of 5-nitro-2-methyl-benzo[d][1,3]oxazin-4-one (0.60 g, 2.91 mmol) and 3-amino-piperidine-2,6-dione hydrogen chloride (0.48 g, 2.91 mmol) in pyridine (15 mL) were heated at 170° C. for 10 minutes in a microwave oven. The suspension was filtered and washed with pyridine (5 mL). The filtrate was concentrated in vacuo. The resulting mixture was stirred in HCl (30 mL, 1N), ethyl acetate (15 mL) and ether (15 mL) for 2 hrs. The suspension was filtered and washed with water (30 mL) and ethyl acetate (30 mL) to give a dark brown solid, which was stirred with methanol (50 mL) at room temperature overnight. The suspension was filtered and washed with methanol to give 3-(2-methyl-5-nitro-4-oxo-4H-quinazolin-3-yl)-piperidine-2,6-dione as a black solid (490 mg, 27% yield). The solid was used in the next step without further purification.

Step 5: A mixture of 3-(2-methyl-5-nitro-4-oxo-4H-quinazolin-3-yl)-piperidine-2,6-dione (250 mg) and Pd(OH)$_2$ on carbon (110 mg) in DMF (40 mL) was shaken under hydrogen (50 psi) for 12 hrs. The suspension was filtered through a pad of Celite and washed with DMF (10 mL). The filtrate was concentrated in vacuo and the resulting oil was purified by flash column chromatography (silica gel, methanol/methylene chloride) to give 3-(5-amino-2-methyl-4-oxo-4H-quinazolin-3-yl)-piperidine-2,6-dione as a white solid (156 mg, 69% yield): HPLC: Waters Symmetry $C_{18}$, 5 μm, 3.9×150 mm, 1 mL/min, 240 nm, 10/90 $CH_3CN/0.1\%$ $H_3PO_4$, 3.52 min (99.9%); mp: 293-295° C.; $^1$H NMR (DMSO-$d_6$) δ 2.10-2.17 (m, 1H, CHH), 2.53 (s, 3H, $CH_3$), 2.59-2.69 (m, 2H, $CH_2$), 2.76-2.89 (m, 1H, CHH), 5.14 (dd, J=6, 11 Hz, 1H, NCH), 6.56 (d, J=8 Hz, 1H, Ar), 6.59 (d, J=8 Hz, 1H, Ar), 7.02 (s, 2H, $NH_2$), 7.36 (t, J=8 Hz, 1H, Ar), 10.98 (s, 1H, NH); $^{13}$C NMR (DMSO-$d_6$) δ 20.98, 23.14, 30.52, 55.92, 104.15, 110.48, 111.37, 134.92, 148.17, 150.55, 153.62, 162.59, 169.65, 172.57; LCMS: MH=287; Anal. Calcd. for $C_{14}H_{14}N_4O_3+0.3H_2O$: C, 57.65; H, 5.05; N, 19.21. Found: C, 57.50; H, 4.73; N, 19.00.

6.2 Assays

6.2.1 TNFα Inhibition Assay in PMBC

Peripheral blood mononuclear cells (PBMC) from normal donors are obtained by Ficoll Hypaque (Pharmacia, Piscataway, N.J., USA) density centrifugation. Cells are cultured in RPMI 1640 (Life Technologies, Grand Island, N.Y., USA) supplemented with 10% AB+human serum (Gemini Bioproducts, Woodland, Calif., USA), 2 mM L-glutamine, 100 U/mL penicillin, and 100 μg/mL streptomycin (Life Technologies)).

The PBMCs (2×10$^5$ cells) were plated in 96-well flat-bottom Costar tissue culture plates (Corning, N.Y., USA) in triplicate. The cells were stimulated with LPS (from *Salmonella abortus equi*, Sigma cat. no. L-1887, St. Louis, Mo., USA) at 1 ng/mL final in the absence or presence of compounds to be tested. The compounds were dissolved in DMSO (Sigma) and further dilutions were done in culture medium immediately before use. The final DMSO concentration in all assays was about 0.25%. The compounds were added to cells 1 hour before LPS stimulation. The cells were then incubated for 18-20 hours at 37° C. in 5% $CO_2$, and supernatants were then collected, diluted with culture medium and assayed for TNFα levels by ELISA (Endogen, Boston, Mass., USA). $IC_{50}$ values were calculated using non-linear regression, sigmoidal dose-response, constraining the top to 100% and bottom to 0%, allowing variable slope (GraphPad Prism v3.02).

6.2.2 Inhibition of MM Cell Proliferation

The ability of compounds to effect the proliferation of MM cell lines was investigated in an in vitro study. Uptake of [$^3$H]-thymidine by H929 MM cells and 7-AAD uptake in several MM cell lines (H929, U266B1, Anb1-6, KMS-34, OPM-2, DF-15, DF15/R, CAG, MM1.S and LP-1) was measured as an indicator of cell proliferation. Cells were incubated in the presence of compounds for 72 hours ([$^3$H]-thymidine was included for the last 6 hours of the incubation period) or 5 days followed by 7-AAD uptake to measure and count viable cells.

6.2.3 Cytokine Production by T Cells

T cells were isolated from buffy coat by negative selection using the RosetteSep® T Cell Enrichment Cocktail. The manufacturer's procedures were followed accordingly. All 96-well plates were pre-coated with 3 μg/ml anti-human CD3 antibody in 100 μl 1×PBS for 4 hours at 37° C. The plates were washed three times with RPMI-1640 Complete Media prior to the T cell assay. T cells were then plated in CD3 pre-coated plates at a density of 2.5×10$^5$ cells/well in 180 μl RPMI-1640 Complete Media. The cells were treated with 20 μl 10× titrated compounds at 10, 1, 0.1, 0.01, 0.001, 0.0001 and 0.00001 μM. Final DMSO concentrations were 0.25%. The plates were incubated for 48 hours at 37° C., 5% $CO_2$. After 48 hours, the supernatants were harvested and tested by a multi-plex cytomteric bead array (CBA) assay for the following cytokines/chemokines: IL-2, IL-3, IL-5, IL-10, IL-13, IL-15, IL-17a, GM-CSF, G-SCF, IFN-γ, TNF-α and RANTES. The CBA plates were analyzed on the Luminex IS100 instrument.

Cytokine levels were normalized to the amount produced in the presence of the amount of a compound tested, and $EC_{50}$ values were calculated using non-linear regression, sigmoidal dose-response, constraining the top to 100% and bottom to 0%, allowing variable slope (GraphPad Prism v3.02).

Anti-CD3-Stimulated Human T Cell Assay

All 96-well plates were pre-coated with 3 μg/mL anti-human CD3 antibody in 100 μL 1×PBS for 4 hours at 37° C. The plates were washed 3 times with RPMI-1640 Complete Media prior to the T cell assay. The T cells were then plated in anti-CD3-pre-coated plates at a density of 2.5×105 cells/well in 180 μL RPMI-1640 Complete Media. The cells were treated with 20 μL 10× titrated Celgene compounds at 10, 1, 0.1, 0.01, 0.001, 0.0001, and 0.00001 μM in duplicate. The final DMSO concentrations were 0.25%. The plates were incubated for 48 hours at 37° C., 5% CO2. After 48 hours, the supernatants were harvested and tested by a multiplex cytometric bead array (CBA) assay for the following cytokines/chemokines: IL-2, IL-3, IL-5, IL-10, IL-13, IL-15, IL-17A, GM-CSF, G-CSF, IFN-γ, TNF-α, and RANTES. The CBA plates were analyzed on the Luminex IS100 instrument.

6.2.4 Cytotoxicity Assay

Cells line Farage, DOHH2 and Rec-1 were obtained from American Type Culture Collection (Manassas, Va., USA) Cytotoxicity assays were measured in 3 day ATP production assays as follows:

The cells were plated in black/clear-bottom 96-well TC plates (BD Falcon, Cat #353948) at 3000 cells/75 μL (for DoHH-2 and Farage cells) or 6000 cells/75 μL (Rec-1 cells) media per well. Stock solutions (40×) of compounds were prepared in DMSO and 4× solutions were prepared by diluting the 40× stock solutions 1:10 with 1% DMSO in culture medium In each assay plate well, 25 μL of the compound of Formula I in 1% DMSO were added to the cells in triplicate so that the final volume was 100 μL and [DMSO] final was 0.25%. Plates were then sealed with breathable sealing films (ISC BioExpress, Cat # T-2421-50) and placed in a 37° C., 5% $CO_2$ humidified incubator for 72 hours. In addition, cells were seeded in a separate plate in the same manner as above, 25 μL medium in 1% DMSO was added to each well. This plate was immediately tested in the CellTiter-Glo Luminescent Cell Viability Assay (Promega, Cat # G7572) as 0 time point and the results were used to calculate $GIC_{50}$ in the Farage and DOHH-2 cell experiments After 72 hours of incubation, 100 μL of CellTiter-Glo reagent were added to each well and incubated at room temperature with gentle shaking for 30 minutes. The plates were then analyzed for luminescence in a TopCount NXT Reader (Packard). Each well was counted for one second. Values for duplicate wells were averaged and then compared to the zero time point DMSO control (0% inhibition) to calculate the percentage inhibition of cell growth. Mean DOHH-2 $GIC_{50}$ values and Farage $GIC_{50}$ values were calculated from three experiments. Rec-1 $IC_{50}$ values were calculated from two experiments.

6.2.5 Cell Cycle Analysis

Cells were treated with DMSO or an amount of a compound provided herein for 48 hours. Propidium iodide staining for cell cycle was performed using CycleTEST PLUS (Becton Dickinson) according to manufacturer's protocol. Following staining, cells were analyzed by a FACSCalibur flow cytometer using ModFit LT software (Becton Dickinson).

6.2.6 Apoptosis Analysis

Cells were treated with DMSO or an amount of a compound provided herein at various time points, then washed with annexin-V wash buffer (BD Biosciences). Cells were incubated with annexin-V binding protein and propidium iodide (BD Biosciences) for 10 minutes. Samples were analyzed using flow cytometry.

6.2.7 NK Cell Analysis

Ninety-six-well flat-bottom plates were coated with 100 μg/mL of human IgG (Sigma) overnight at 4° C. The next day, unbound IgG was washed away with cold 1×PBS. NK cells were then plated in the IgG-coated 96-well plates at 2×105 cells per well in 180 μL RPMI-1640 Media and 10 ng/mL of rhIL-2 (R & D Systems, MN) was added. Test compounds were added in a volume of 20 μL DMSO. Final concentrations of test compounds were 0.0001, 0.001, 0.01, 0.1, 1, or 10 μM. Final DMSO concentrations were 0.25%. After 48 hours, the supernatants were harvested and analyzed by ELISA for IFN-γ production.

6.2.8 Results

The biological activities of the compound of Formula I are summarized in Tables 1 to 5. In the anti-CD3-stimulated human T cell assay described above, the compound of Formula I enhanced production of IL-2, IL-3, IL-5, IL-10, IL-15, GM-CSF, INF-γ, RANTES, and TNF-α at concentrations of 0.01 to 10 μM. Enhancement of IL-2, IL-3, IL-13, GM-CSF, TNF-α, and RANTES by the compound was concentration-dependent. At a concentration of 0.1 μM of the compound of Formula I, production of IL-2 and IL-13 was enhanced to levels 14× and 7× those in control cells, respectively. At a concentration of 1 μM of the compound of Formula I, production of IL-2 and IL-13 was enhanced to levels 17× and 8× those in control cells, respectively. The compound enhanced IL-10 production 2-fold at low concentrations (≤0.01 μM) but inhibited IL-10 production at 1 and 10 μM. The compound increased IL-5 production 3- and 4-fold at 0.01 and 0.1 μM, respectively, showing less enhancement at both lower and higher concentrations.

Additionally, it was observed that, in a human umbilical artery assay, the compound of Formula I was a potent anti-angiogenic agent with an $IC_{50}$ of 9.4 nM; and the compound of Formula I did not inhibit HUVEC proliferation.

In a mouse Matrigel™ angiogenesis assay, it was observed that the compound of Formula I significantly inhibited blood vessel growth at 30 mpk and exhibited a dose dependent inhibition of angiogenesis.

It was observed that the compound of Formula I induced G1 arrest in DoHH2 and WSU-DLCL2. It was also observed that, in proliferation assays, the compound of Formula I acted synergistically with Rituxan, as calculated using the Chou-Talalay method.

In a DoHH2 xenograft model, it was observed that the compound of Formula I inhibited tumor growth and that the combination of the compound of Formula I with Rituxan significantly delayed time to tumor endpoint (63%) at 30 mg/kg dose. Tumor growth inhibition was observed at 3 and 30 mpk of the compound of Formula I in combination with Rituxan (1 mg/kg), at 45% and 55% on day 12, respectively. It was also observed that the compound of Formula I significantly inhibited blood vessels counts in tumor.

In a WSU-DLCL2 xenograft model, the combination of the compound of Formula I with Rituxan (2 mg/kg iv qw) yielded 60% and 90% complete regressions (tumor volume <25 mm³) at 3 and 30 mg, respectively.

In a NCI-H929 MM xenograft model, the compound of Formula I inhibited H929 tumor growth in a dose-dependent manner. On day 19, the compound showed 93% tumor growth inhibition at 30 mg/kg, 73% tumor growth inhibition at 3 mg/kg, and 59% tumor growth inhibition at 0.3 mg/kg.

In a U87 GB xenograft model, dose dependent inhibition of tumor volume was observed. The compound of Formula I significantly inhibited U87 tumor growth at 3 and 30 mg/kg qd.

TABLE 1

In Vitro Activities

| Assay | $IC_{50}$ or $EC_{50}$ (µM) |
|---|---|
| PBMC TNFα | 0.063[a] |
| WB TNFα | 0.164[a] |
| LPS-induced TNFα | 0.017[a] |
| T cell IL-2 | 0.012-0.014[c] |
| REC1 (MCL) | 0.47[a] |
| DoHH2 (FL) | 0.61[b] |
| Farage (GCB-DLBCL) | 0.70[b] |
| Human angiogenesis | 0.0094[a] |
| NK cell IFNγ | 0.0015[c] |
| B cell proliferation | 0.015[c] |
| B cell IgG | 0.061[a] |
| Immature MK colonies | >10[a] |
| Intermediate MK colonies | >10[a] |

[a] = $IC_{50}$,
[b] = $GIC_{50}$,
[c] = $EC_{50}$

TABLE 2

In Vitro Activities (5 Day ³H Thymidine Incorporation Assay)

| | | $IC_{50}$ (µM) |
|---|---|---|
| ABC Subtype | OCI-Ly10 | 0.0085 |
| | U2932 | 0.11-0.12 |
| | TMD8 | 0.44 |
| | RIVA | 4.3 |
| PMBL | Karpas-1106P | 0.58-0.71 |
| GCB Subtype | WSU-DLCL2 | 0.79-2.1 |
| | SUDHL4 | >10 |
| | OCI-Ly19 | >10 |

TABLE 3

Activity of the Compound of Formula I against Lenalidomide Resistant Cell Lines ($IC_{50}$ (µM))

| | H929 | D1 | 1051 | 1052 | 1053 | 1054 |
|---|---|---|---|---|---|---|
| Lenolidomide (n = 3) | 12.64 | No $IC_{50}$ | No $IC_{50}$ | No $IC_{50}$ | No $IC_{50}$ | No $IC_{50}$ |
| Cmpd. of Form. I (n = 3) | 0.1539 | 0.3092 | 2.974 | 4.238 | 2.099 | 6.593 |

TABLE 4

Effect of the Compound of Formula I in HIF-1α protein expression in solid tumor cell

| Cancer cell lines | | % Inhibition at (1 µM) |
|---|---|---|
| Breast Cancer | MCF-7 | 74.82% |
| Colorectal Cancer | HCT116 | 74.60% |
| | HT29 | 78.54% |
| | HCT15 | 69.26% |
| Ovarian Cancer | Skov-3 | 100.00% |
| | Ovcar-3 | 63.39% |
| Prostate cancer | DU145 | 66.01% |
| Pancreatic Cancer | Miapaca-3 | 33.72% |
| Renal Cancer | 786-O | 41.70% |
| Brain Cancer | U87 | 73.81% |

TABLE 5

Anti-Proliferative Activity of the Compound of Formula I in DLBCL cell lines

| Compound of Formula I | Correlation with Anti-proliferative activity (100 nM) | Statistics | |
|---|---|---|---|
| Oncomine ™ ABC scores | Correlated | P < 0.05 | $r^2 = 0.48$ |
| Oncomine ™ NFκB scores | Not Correlated | P > 0.05 | $r^2 = 0.35$ |
| Baseline activity of NFκB subunit p50 | Correlated | P < 0.005 | $r^2 = 0.60$ |
| baseline activity of NFκB subunit p65 | Correlated | P < 0.01 | $r^2 = 0.65$ |
| Baseline IRF4 gene expression | Correlated | P < 0.05 | $r^2 = 0.47$ |
| Baseline SPIB gene expression | Not Correlated | P > 0.05 | $r^2 = 0.027$ |
| Baseline cyclin D1 gene expression | Not Correlated | P > 0.05 | $r^2 = 0.21$ |
| Baseline A20 gene expression | Not Correlated | P > 0.05 | $r^2 = 0.044$ |
| Baseline CARD11 gene expression | Correlated | P < 0.05 | $r^2 = 0.54$ |
| Baseline CRBN gene expression | Correlated | P < 0.05 | $r^2 = 0.45$ |

6.3 Pharmacokinetics

It was observed that the compound of Formula I had a $t_{1/2}$ of 230 min in human plasma. The oral pharmacokinetic parameters in mouse, rat, and monkey are summarized in Tables 5 to 7. Exposures ($AUC_{(0-t)}$) of the compound of Formula I increased in a dose proportional manner up to 30 mg/kg in SCID mouse, CD-IDS rat, and male monkey. The compound of Formula I did not inhibit any megakaryocyte progenitor cells at 10 µM.

TABLE 6

Oral Pharmacokinetics

| | SCID Mouse | SD Rat | Cyno Monkey |
|---|---|---|---|
| Dose (mpk) | 3 po | 30 po | 3 po |
| $C_{max}$ (ng/mL (µM)) | 2900 (10) | 4800 (17) | 3300 (11) |
| AUC (ng-h/mL (µM-h)) | 7100 (25) | 25000 (87) | 12000 (43) |
| $T_{1/2}$ (h) | | 2.7 | 5.8 |
| CLp (mL/min/kg) | | 11 | 1.2 |
| F (%) | | 53 | 32 |

TABLE 7

PK Profiles in Male Monkeys

| Dose (mg/kg) | $C_{max}$ (ng/mL) | $AUC_{0-t}$ (ng*h/mL) |
|---|---|---|
| 0.3 | 100 (0.36 μM) | 1300 (4.5 μM-h) |
| 3 | 1100 (3.8 μM) | 14000 (49 μM-h) |
| 10 | 3100 (11 μM) | 38000 (130 μM-h) |
| 30 | 7700 (27 μM) | 99000 (350 μM-h) |

TABLE 8

Pharmacokinetics in Monkeys on Day 1

| Dose (mg/kg) | $T_{max}$ (h) | $C_{max}$ (ng/mL) | $AUC_{0-24}$ (ng*h/mL) |
|---|---|---|---|
| 0.15 | 2 to 4 (m[a]) | 36 (m) | 430 (m) |
|  | 2 (f[b]) | 63 (f) | 450 (f) |
| 1.5 | 2 to 4 (m) | 510 (m) | 4600 (m) |
|  | 2 (f) | 680 (f) | 4100 (f) |
| 15 | 4 (m) | 4100 (m) | 51000 (m) |
|  | 2 to 4 (f) | 4200 (f) | 38000 (f) |

[a]m: Male;
[b]f: Female.

TABLE 9

Pharmacokinetics in Monkeys on Day 27

| Dose (mg/kg) | $T_{max}$ (h) | $C_{max}$ (ng/mL) | $AUC_{0-24}$ (ng*h/mL) |
|---|---|---|---|
| 0.15 | 4 (m[a]) | 53 (m) | 570 (m) |
|  | 2 to 4 (f[b]) | 57 (f) | 450 (f) |
| 1.5 | 2 (m) | 560 (m) | 5700 (m) |
|  | 0.5 to 2 (f) | 590 (f) | 4200 (f) |
| 15 | 2 to 4 (m) | 5800 (m) | 72000 (m) |
|  | 4 (f) | 7000 (f) | 75000 (f) |

[a]m: Male;
[b]f: Female.

The oral administration of the compound of Formula I at 100, 300, and 10000 mg/kg/day for 7 consecutive days in the male CD-IGS rat resulted generally in near dose proportional exposure increases. The NOAEL was determined to be 1000 mg/kg/day.

6.4 In Vitro DLBCL Cell Thymidine Incorporation Assay

A panel of DLBCL cell lines of various cytogenetic features was tested for their sensitivity to the antiproliferative activity of the compound of Formula I (FIG. 2). Cells were treated with the compound of Formula I for 5 days at 37° C.; proliferation of cells was determined using $^3$H-thymidine incorporation method. Results of 3 independent experiments are shown (mean±SD) in FIG. 2. The compound starting at 0.1-1 μM significantly (p<0.05) inhibited proliferation of several lines of DLBCL cells, particularly ABC-subtype cells such as Riva, U2932, TMD8, OCI-Ly3 and OCI-Ly10 cells. ABC-subtype cells appear more sensitive to the antiproliferative effect than other subtype cells including GCB-DLBCL and PMBL cells.

6.5 Inhibitory Effect on NFκB Activity in DLBCL Cells

DLBCL cells were treated with the compound of Formula I or an IKK1/2 dual inhibitor (used as a positive inhibitor control) for 2 days. NFκB activity was examined with Active Motif transcription factor assay using nuclear extracts from cells following treatment. Results are shown in FIG. 1 (mean±SD). The compound of Formula I significantly inhibits NFκB p65 and p50 activity at concentrations of 0.1 μM, 1 μM and 10 μM. The compound of Formula I was found to inhibit the NFκB activity in some DLBCL lines of the ABC subtype, such as U2932 and OCI-Ly10 cells. These results suggest that an effect on NFκB signal transduction might be involved in the antiproliferative activity of the compound of Formula I against ABC-DLBCL cells, and that the baseline NFκB activity may be a predictive biomarker of lymphoma tumor response to therapy with the compound.

6.6 In Vivo Mouse Xenograph Model for the OCI-LY10 Cell Subtype

Efficacy of the compound of Formula I against the OCI-Ly10 cell subtype is investigated in an in vivo mouse xenograft model. Female CB.17 SCID mice age 6 to 12 weeks are injected with about 0.2 mL/mouse of 1×10$^7$ OCI-Ly10 tumor cells in 100% Matrigel sc in flank. Treatment with the compound of Formula I begins once tumor reaches an average size of 100 to 150 mg. Body weight is measured 5/2 and then biweekly to the end of the study. Caliper measurement of the tumor is performed biweekly. The endpoint of the study is tumor growth delay (TGD). The percentage TGD is calculated. Animals are monitored individually. The endpoint of the study is a tumor volume of about 1000 m$^3$ or 60 days, whichever comes first. Responders to therapy may be followed longer.

Tumor collection: collect tumors in RNAse free environment (divide into 3 parts). Part is preserved via snap freeze as a powder for future protein analysis, shipping condition –80° C. Part 2 is preserved in RNA later, snap freeze, shipping condition –80° C. Part 3 is preserved in formalin for 24 hours, then 70% ethanol, ship at room temperature to PAI for paraffin embedding. The treatment plan is shown below.

| Gr. | N | Agent | mg/kg | Route | Schedule |
|---|---|---|---|---|---|
| 1 | 10 | vehicle 1 | — | po | qd x 28 |
| 2 | 10 | Compound of Formula I | 3 | po | qd x 28 |
| 3 | 10 | Compound of Formula I | 10 | po | qd x 28 |
| 4 | 10 | Compound of Formula I | 30 | po | qd x 28 |
| 5 | 10 | vincristine | 1 | iv | q4d x 28 |

6.7 Multiple Myeloma Models

The ability of 3-(5-amino-2-methyl-4-oxo-4H-quinazolin-3-yl)-piperidine-2,6-dione to inhibit cancer cell growth was evaluated in a number of multiple myeloma (MM) cell lines using in vitro and in vivo methods (FIGS. 5A & 5B). 3-(5-amino-2-methyl-4-oxo-4H-quinazolin-3-yl)-piperidine-2,6-dione was shown to inhibit MM cell proliferation in a number of cell lines (FIGS. 5A, 5B & 6). For example, the antiproliferative effect of 3-(5-amino-2-methyl-4-oxo-4H-quinazolin-3-yl)-piperidine-2,6-dione was demonstrated in a N929 xenograft model (FIG. 6).

6.8 Cereblon Models in ABC-DLBCL, Multiple Myeloma and Colorectal Cancer Cells The effect of the protein cereblon (CRBN) on the efficacy of the compound of Formula I to inhibit the proliferation, cell cycle progression and/or cell invasion of various cancer cell lines was studied. The compound of Formula I was found to interact with endogenous myeloma CRBN and in a dose-dependent manner. The compound of Formula I also interacts with HepG2 HCC CRBN in a dose-dependent manner. In addition, the compound of Formula I was found to inhibit CRBN ubiquitination with an $IC_{50}$ of 208.7 μm.

ABC-DLBCL Cell Model

The expression of cereblon was found to modulate the efficacy of the compound of Formula I against proliferation of ABC-DLBCL cell lines (FIG. 7A-7C). Cereblon was required for inhibition of each of IRF4 expression, NFκB activity, and cell proliferation.

Myeloma Cell Models

The effect of cereblon in H929 myeloma cells was also evaluated. H929 cells were transfected with mock, negative control siRNA and CRBN-siRNA-7 for 24, 48, 72 and 96 hours. Cells were treated 24 h after transfection with DMSO (0.1%) or the compound of Formula I for 1, 2, 3 days and the effect on cell cycle and proliferation investigated. The compound of Formula I induced a delay of cell cycle progression, measured as the decrease of the number of cells in S phase, in control mock and negative control siRNA-transfected cells after 72 h treatment (FIG. 8). Knockdown of CRBN markedly abrogated drug-induced delay in cell cycle progression in H929 cells from 65 to 22% for the compound of Formula I.

Figure 9A:
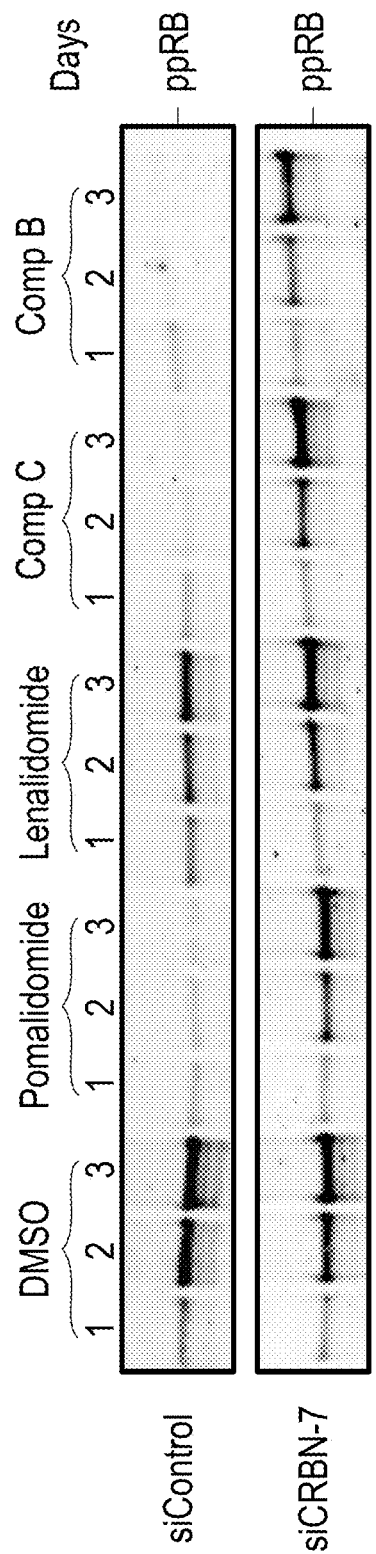
Figure 9B:
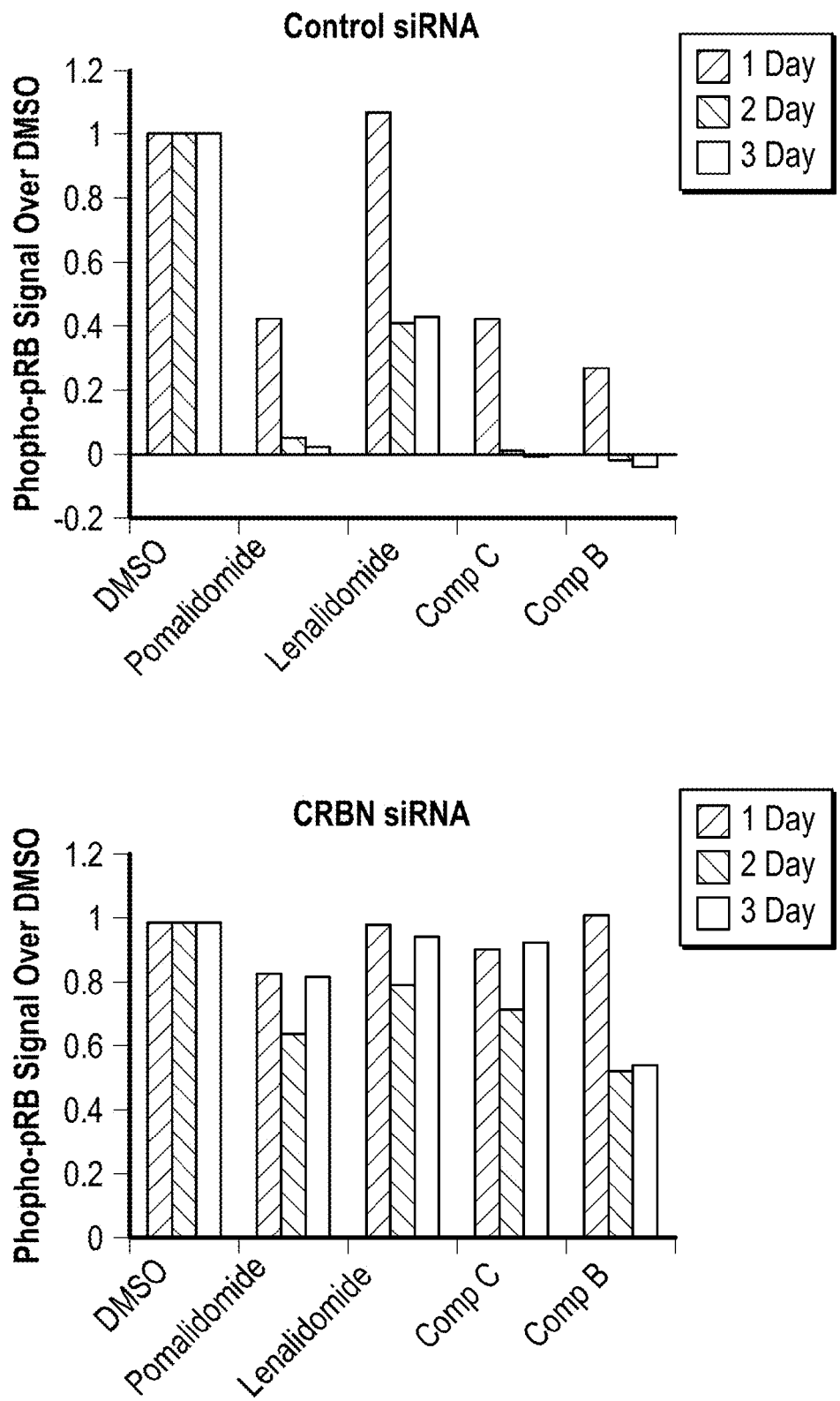
Figure 9C:
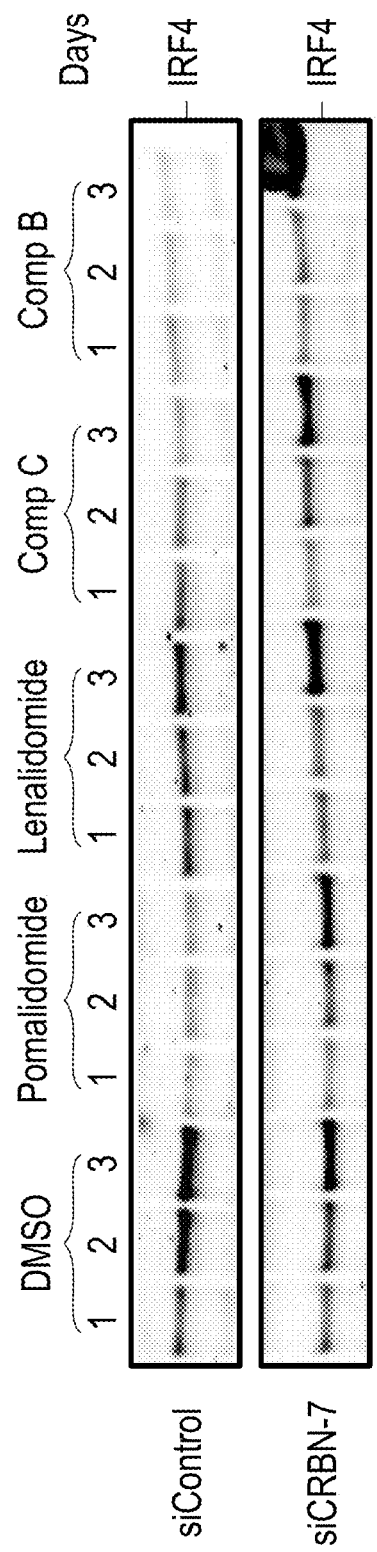
Figure 9D:
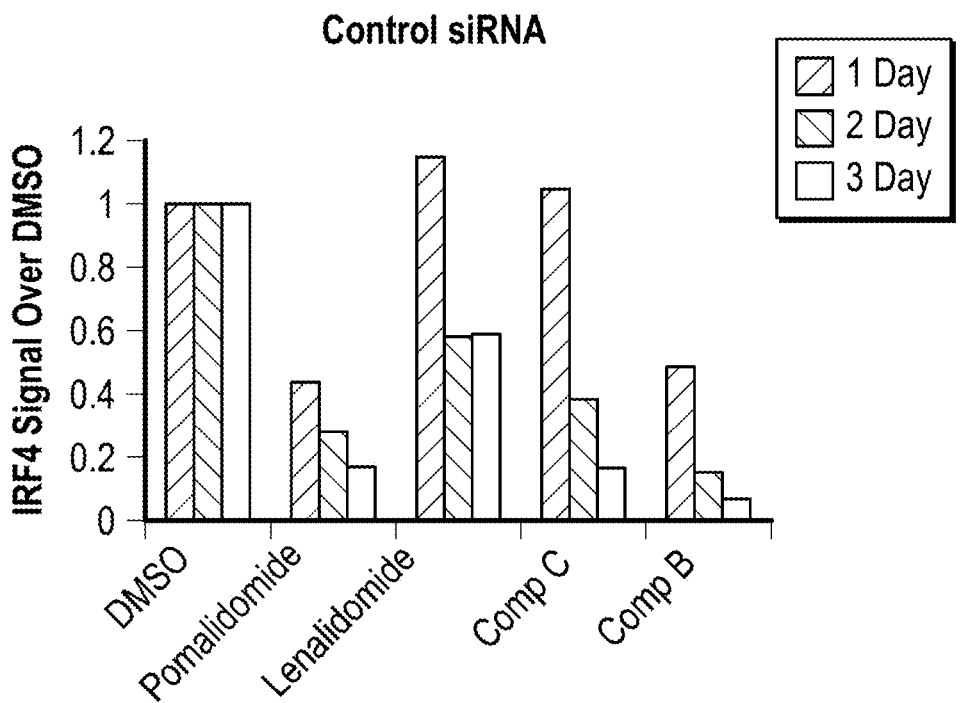
Figure 9D:
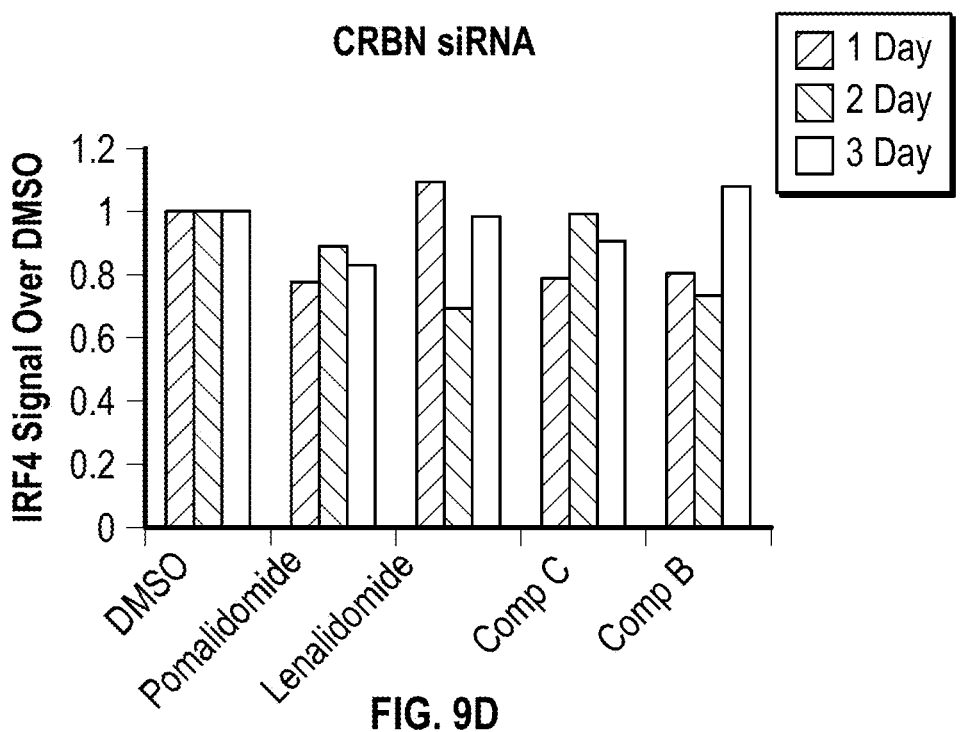

RT-PCR and Western blot analysis was used to measure the levels of key cell cycle and apoptotic regulators in order to further investigate the effects of CRBN on the cell cycle arrest induced by the compound of Formula I. In H929 cells, the cell cycle arrest in G1 phase by the compound of Formula I coincides with a reduction of tumor suppressor, pRb, phosphorylation and the oncogene and myeloma survival factor IRF4. Western blot analysis showed that the compound of Formula I decreased phosphorylation of pRB (FIGS. 9A & 9B) and total level of protein IRF4 (FIGS. 9C & 9D). The effect was reduced by knockdown of CRBN suggesting that inhibition of cell cycle progression by the drugs requires CRBN protein.

The compound of Formula I was found to inhibit the proliferation of CRBN-sensitive MM cell lines U266, 100-1 and 1K-2 (FIG. 10).

Colorectal Cell Model

The expression of cereblon also modulates the anti-invasive activity of the compound of Formula I in HCT-15 colorectal cancer cells (FIG. 11). The ability of the compound of Formula I to inhibit invasion of HCT-15 cells was reduced by siCRBN.

6.9 Solid Tumor Models

The compound of Formula I was evaluated for its effect on solid tumor cell lines from a variety of histologies (e.g., breast, ovarian, colorectal, HCC). The compound of Formula I inhibits hypoxia-induced HIF1-α expression in many such solid tumor cell lines (FIG. 12A-12I). In addition, the compound of Formula I inhibits the invasion of solid tumor cells to varying degrees (Table 10) and cell colony formation (Table 11). The inhibition of solid tumor cell colony formation was studied by a single high concentration treatment of the Compound of formula I (10 μM) on day 1, followed by monitoring of cell colony formation over the course of 10 to 20 days (Table 11, FIGS. 13A & 13B).

The compound of Formula I inhibits U87 glioiblastoma tumor cell growth at 3 and 30 mg/kg q.d. in a xenograft model (FIG. 14).

TABLE 10

Effects of the Compound of Formula I on Invasion of Solid Tumor Cells

| Tumor Cell Type | Cell Line (stimulation) | Invasion ($IC_{50}$) Compound of Formula I |
| --- | --- | --- |
| hepatocellular | HepG2 (VEGF) | <0.001 |
| | SK-HEP-1 (VEGF) | 0.0061 |
| glioblastoma | SNB-19 (PDGF) | 0.16 |
| | SF-539 (PDGF) | 0.025 |
| | U251 (PDGF) | 3.7 |
| | SF-295 (PDGF) | 0.24 |
| | U87 (PDGF) | 0.08 |
| colorectal | HCT15 (bFGF) | 0.0072 |

TABLE 11

Effects of the Compound of Formula I in Solid Tumor Cell Colony Formation

| Tumor Cell Type | Cell Line | % Inhibition of Colony Formation[a] |
| --- | --- | --- |
| hepatocellular | HCT15 | 3 |
| | HCT116 | 13** |
| | Colo-205 | 17** |
| ovarian | OVCAR-3 | 18* |
| HCC | SK-HEP-1 | 6 |
| | HEP-G2 | 6.9 |
| glioblastoma | SF268 | 0.6 |
| | SF295 | 12.9 |
| | U251 | −6 |
| | U87 | 2 |
| breast | MDA-MB-453 | −7 |
| | MCF-7 | 1.4 |
| | ZR-75-1 | 90** |
| prostate | PC-3 | 14.8 |

[a] 10 μM of Compound of Formula I.
*p < 0.5;
**p < 0.001 (versus DMSO).

6.10 PBMC Cytokine Profiling

The compound of Formula I was selected for activity profiling of eleven (11) cytokines and chemokines, i.e., interleukin (IL)-1β, IL-6, IL-8, granulocyte macrophage colony stimulating factor (GM-CSF), macrophage-derived chemokine (MDC), macrophage inflammatory protein-1 alpha (MIP-1α), macrophage inflammatory protein-1beta (MIP-1β), tumor necrosis factor-alpha (TNF-α), IL-10, monocyte chemotactic protein-1 (MCP-1), and RANTES (regulated upon activation normal T-cell expressed, and secreted) using lipopolysaccharide-stimulated human peripheral blood mononuclear cells (hPBMCs) obtained from 2-6 donors.

The compound of Formula I inhibited the production of (in order of potency) TNF-α ($IC_{50}$=0.034 μM), >IL-1β ($IC_{50}$=0.054 μM)>IL-6 ($IC_{50}$=0.060 μM)>MDC ($IC_{50}$=0.062 μM)>MIP-1α ($IC_{50}$=0.30 μM)>GM-CSF ($IC_{50}$=0.95 μM)>IL-8 ($IC_{50}$>10 μM)>MIP-1β ($IC_{50}$>10 μM) (Table 12). The compound of Formula I also enhanced IL-10, MCP-1, and RANTES production with mean percent of control values of 480%, 236%, and 131%, respectively at the 0.1 μM concentration.

TABLE 12

Summary of Cytokine Inhibitory Profile of the Compound of Formula I

|      | IL-6  | IL-8 | IL-1β | GM-CSF | MDC   | MIP-1α | MIP-1β | TNF-α |
|------|-------|------|-------|--------|-------|--------|--------|-------|
| $IC_{50}$ | 0.060 | >10  | 0.054 | 0.95   | 0.062 | 0.30   | >10    | 0.034 |

6.11 VEGF-, BFGF-, and HGF-Induced HUVEC Tube Formation, Migration, and Invasion The compound of formula I demonstrated potent inhibitory activity in an in vitro assay of human umbilical vascular endothelial cell (HUVEC) invasion. The compound of formula I strongly inhibited vascular endothelial growth factor (VEGF)-, basic fibroblast growth factor (bFGF)-, and hepatocyte growth factor (HGF)-induced invasion, weakly inhibited VEGF and bFGF-induced HUVEC tube formation and migration, and either enhanced or did not inhibit proliferation of growth factor-induced HUVEC proliferation. The $IC_{50}$ value for inhibition of VEGF-induced HUVEC invasion was 0.29 nM. The $IC_{50}$ value for inhibition of bFGF-induced HUVEC invasion was 5.5 nM. The $IC_{50}$ value for inhibition of HGF-induced HUVEC invasion was 110 nM. The compound of Formula I inhibited VEGF- and bFGF-induced migration 38% and 28%, respectively at a concentration of 1 µM.

6.12 Clinical Protocol

A Phase 1a/1b, clinical study to determine the safety, tolerability, pharmacokinetics and efficacy of the compound of Formula I when administered orally to subjects with advanced solid tumors, Non-Hodgkin's lymphoma, or multiple myeloma is provided. The non-tolerated dose (NTD), the maximum tolerated dose (MTD) and the recommended phase 2 dose (RP2D) are to be defined in the study. The effect of the compound on biomarkers of angiogenesis in pre- and during treatment tumor biopsies will be evaluated.

Study Design

The study is designed as a Phase 1a/1b study consisting of two parts: dose escalation (Part A), and dose expansion (Part B). In Part A, subjects will receive single and multiple ascending doses of the compound of Formula I to measure pharmacokinetics (PK) and identify the maximum tolerated dose (MTD) and the recommended phase 2 dose (RP2D). A standard dose (3+3) escalation design (Simon et al., 1997) will be used to identify initial toxicity. Initial cohorts of three subjects will be given the compound of Formula I (0.5 mg once daily) in dose increments of 100% until the first instance of grade 3 or higher toxicity suspected to be drug-related in the first cycle, at which point the particular cohort will be expanded to a total of six subjects. This standard escalation schedule will be initiated in order to establish the non-tolerated dose (NTD) and MTD. Smaller increments and additional subjects within a dose cohort may also be evaluated for safety. Approximately 20 to 40 subjects will be treated and evaluated in Part A; however, the total number of subjects in Part A depends on the number of dose cohorts needed to establish the MTD. A dose will be considered the NTD when 2 or more out of 6 evaluable subjects in a cohort experience drug-related dose limiting toxicity (DLT) during Cycle 1. When the NTD is established, dose escalation will stop. The MTD is defined as the last dose level below the NTD with 0 or 1 out of 6 evaluable subjects experiencing DLT during Cycle 1. An intermediate dose (i.e., one between the NTD and the last dose level before the NTD) or additional subjects within any dose cohort may be required to more precisely determine the MTD and RP2D.

In Part B, subjects may start dosing at the MTD and/or a lower dose level based on safety, PK and/or PD data from Part A. Approximately 100 subjects (up to 20 per cohort), stratified by tumor type, will be treated and evaluated for safety and antitumor activity after every two cycles of therapy. The dose, doses, or schedule appropriate will also be determined. During Part B, safety data will be reviewed regularly regarding the study continuation, as appropriate.

Study Population

Men and women, 18 years or older, with advanced Solid Tumors (ST), Non-Hodgkin's Lymphoma (NHL), Multiple Myeloma (MM), or advanced unresectable solid tumors, including subjects who have progressed on (or not been able to tolerate) standard therapy or for whom no standard anticancer therapy exists. Selected tumor types include metastatic breast cancer (mBC), glioblastoma multiforme (GBM), hepatocellular carcinoma (HCC), diffuse large B-cell lymphoma (DLBCL), and multiple myeloma (MM).

Dosing and Length of Study

During the first cycle, only in Part A, each subject will be administered a single daily dose of the compound of Formula I on Day 1 followed by a 48-hour observation and PK sampling period, followed on Day 1 by daily uninterrupted dosing for 28 days (Cycle 1=30 days). In subsequent Part A cycles, subjects are treated in 28-day cycles with continuous dosing from Day 1 to 28. The Compound of Formula I will be given once or twice a day at a dose of 0.1, 0.5, 1, 2, 4, 5, 7.5, 10, 20, 25, or 50 mg in an initial dose. The dose may be of 0.1, 0.5, 1, 2, 4, 5, 7.5, 10 mg given once a day. The dose may be 50, 25, or 10 mg given twice a day. The dose may be adjusted up, or down, from the starting dose during treatment. As described above, if needed, the drug may be given in a cyclical manner.

In Part B, subjects receive continuous dosing for 28 days from the beginning—there is no post initial, single dose 48-hour PK collection period.

Therapy will be discontinued if there is evidence of disease progression, unacceptable toxicity or subject/physician decision to stop. Subjects may continue to receive compound without interruption for as long as they derive benefit as judged by the Investigator.

Enrollment is expected to occur over approximately 24 months. Completion of active treatment and subject follow-up is expected to take an additional 3-6 months Study Treatments Celgene Corporation will supply the compound of Formula I (HCl) as 0.1 mg, 0.5 mg, 1 mg and 3 mg capsules for oral administration. The compound will be packaged in bottles inside boxes containing drug for 28 days.

In Part A (the dose escalation phase), the dose level will start at 0.5 mg once daily after the single PK dose. After the first dose is administered to the last subject in any cohort, subjects are observed for at least 30 days before the next higher, protocol-specified dose cohort can begin. Intra subject dose escalation is not permitted unless approved by the Safety Review Committee (SRC) which will consist of the principal investigator and Celgene's medical monitor.

In Part B, subjects may receive the compound of Formula I at the MTD and/or a lower dose level, based on safety, PK and PD evaluations from Part A. Approximately 100 subjects (preselected tumor types in groups of up to 20) will be evaluated for safety and antitumor effects.

Overview of Efficacy Assessments

Subjects will be evaluated for efficacy after every 2 cycles. The primary efficacy variable is response. Tumor response will be based on Response Evaluation Criteria in Solid Tumors (RECIST 1.1), International Workshop Criteria (IWC) for NHL, International Uniform Response Criteria for Multiple Myeloma (IURC) (Appendix A, Section 18.1), or Responses Assessment for Neuro-Oncology (RANO) Working Group for GBM.

Secondary/exploratory endpoints include biomarker measurements in blood and tumor, histopathologic response and correlations with pharmacogenomic findings. Supplementary efficacy variables (e.g., ECOG performance status, PET outcomes) will also be examined; in addition, hypovascularization changes will be measured by volume transfer constant (Ktrans) and initial AUC (IAUC) using DCE-MRIs.

Overview of Safety Assessments

The safety variables for this study are adverse events, clinical laboratory variables, 12-lead ECGs (centrally reviewed), LVEF assessments, physical examinations and vital signs.

Overview of Pharmacokinetic Assessments

The PK profiles of the compound of Formula I and its metabolites will be determined from serial blood and urine collections during the first treatment cycle. These will be correlated with pharmacodynamic (PD) outcomes where possible.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method of treating or managing non-Hodgkin's lymphoma, comprising administering to a patient in need of such treatment or management a therapeutically effective amount of 3-(5-amino-2-methyl-4-oxo-4H-quinazolin-3-yl)-piperidine-2,6-dione, which has the following structure:

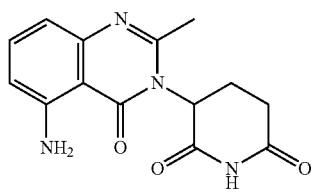 [SMILES: Cc1nc2cccc(N)c2c(=O)n1C1CCC(=O)NC1=O]

or an enantiomer or mixture of enantiomers thereof, or a pharmaceutically acceptable salt, solvate, hydrate, co-crystal, clathrate, or polymorph thereof;
wherein the non-Hodgkin's lymphoma is diffuse large B-cell lymphoma of the activated B-cell phenotype.

2. The method of claim 1, wherein the diffuse large B-cell lymphoma is characterized by the expression of one or more biomarkers overexpressed in RIVA, U2932, TMD8 or OCI-Ly10 cell lines.

3. The method of claim 1, wherein the non-Hodgkin's lymphoma is relapsed or refractory.

4. The method of claim 1, wherein the non-Hodgkin's lymphoma is drug-resistant.

5. A method for treating or managing non-Hodgkin's lymphoma, comprising:
    (i) identifying a patient having non-Hodgkin's lymphoma sensitive to treatment with 3-(5-amino-2-methyl-4-oxo-4H-quinazolin-3-yl)-piperidine-2,6-dione; and
    (ii) administering to the patient a therapeutically effective amount of 3-(5-amino-2-methyl-4-oxo-4H-quinazolin-3-yl)-piperidine-2,6-dione or a pharmaceutically acceptable salt, solvate or hydrate thereof;
    wherein the non-Hodgkin's lymphoma is diffuse large B-cell lymphoma of the activated B-cell phenotype.

6. The method of claim 5, wherein the diffuse large B-cell lymphoma is characterized by the expression of one or more biomarkers overexpressed in RIVA, U2932, TMD8 or OCI-Ly10 cell lines.

7. The method of claim 5, wherein identifying a patient having non-Hodgkin's lymphoma sensitive to treatment with 3-(5-amino-2-methyl-4-oxo-4H-quinazolin-3-yl)-piperidine-2,6-dione, or a salt, solvate or hydrate thereof, comprises characterization of the non-Hodgkin's lymphoma phenotype of the patient as an activated B-cell subtype.

8. The method of claim 7, wherein the non-Hodgkin's lymphoma phenotype is characterized as an activated B-cell subtype of diffuse large B-cell lymphoma.

9. The method of claim 7, wherein the non-Hodgkin's lymphoma phenotype is characterized by the expression of one or more biomarkers overexpressed in RIVA, U2932, TMD8 or OCI-Ly10 cell lines.

10. The method of claim 5, wherein identification of the non-Hodgkin's lymphoma phenotype comprises obtaining a biological sample from a patient having lymphoma.

11. The method of claim 10, wherein the biological sample is a lymph node biopsy, a bone marrow biopsy, or a sample of peripheral blood tumor cells.

12. The method of claim 5, wherein identifying a patient having non-Hodgkin's lymphoma sensitive to treatment with 3-(5-amino-2-methyl-4-oxo-4H-quinazolin-3-yl)-piperidine-2,6-dione, or a salt, solvate or hydrate thereof, comprises identification of a gene associated with the activated B-cell phenotype.

13. The method of claim 12, wherein the gene associated with the activated B-cell phenotype is selected from the group consisting of IRF4/MUM1, FOXP1, SPIB, CARD11 and BLIMP/PDRM1.

14. The method of claim 5, wherein identifying a patient having non-Hodgkin's lymphoma sensitive to treatment with 3-(5-amino-2-methyl-4-oxo-4H-quinazolin-3-yl)-piperidine-2,6-dione, or a salt, solvate or hydrate thereof, comprises measuring the level of NF-κB activity in a biological sample obtained from the patient.

15. The method of claim 14, wherein the biological sample is a lymph node biopsy, a bone marrow biopsy, or a sample of peripheral blood tumor cells.

16. The method of claim 7, wherein characterization of the non-Hodgkin's lymphoma phenotype of the patient as an activated B-cell subtype comprises measuring one or more of the following:
    (i) overexpression of SPIB, a hematopoietic-specific Ets family transcription factor required for survival of activated B-cell subtype cells;
    (ii) higher constitutive IRF4/MUM1 expression than GCB subtype cells;
    (iii) higher constitutive FOXP1 expression up-regulated by trisomy 3;
    (iv) higher constitutive Blimp1, i.e., PRDM1, expression;
    (v) higher constitutive CARD11 gene expression; and
    (vi) an increased level of NF-κB activity relative to non-activated B-cell subtype DLBCL cells.

17. The method of claim 1, wherein the compound is 3-(5-amino-2-methyl-4-oxo-4H-quinazolin-3-yl)-piperidine-2,6-dione hydrochloride, or a salt, solvate or hydrate thereof.

18. The method of claim 1, further comprising the administration of a therapeutically effective amount of one or more additional active agents.

19. The method of claim 18, wherein the additional active agent is selected from the group consisting of an alkylating agent, an adenosine analog, a glucocorticoid, a kinase inhibitor, a SYK inhibitor, a PDE3 inhibitor, a PDE7 inhibitor, doxorubicin, chlorambucil, vincristine, bendamustine, forskolin and rituximab.

20. The method of claim 19, wherein the additional active agent is rituximab.

21. The method of claim 1, wherein 3-(5-amino-2-methyl-4-oxo-4H-quinazolin-3-yl)-piperidine-2,6-dione, or a pharmaceutically acceptable salt, solvate or hydrate thereof is administered in an amount of from about 0.5 to about 50 mg per day.

22. The method of claim 21, wherein the compound is administered in an amount of about 0.5 to about 5 mg per day.

23. The method of claim 21, wherein the compound is administered in an amount of about 0.5, 1, 2, 4, 5, 10, 15, 20, 25 or 50 mg per day.

24. The method of claim 21, wherein the compound is orally administered.

25. The method of claim 21, wherein the compound is administered in a capsule or tablet.

26. The method of claim 25, wherein the compound is administered in 10 mg or 25 mg of a capsule.

27. The method of claim 1, wherein the compound is administered for 21 days followed by seven days rest in a 28 day cycle.

* * * * *